US010837022B1

(12) United States Patent
Jin et al.

(10) Patent No.: US 10,837,022 B1
(45) Date of Patent: Nov. 17, 2020

(54) RECOMBINANT MICROORGANISMS WITH MIXED SUGAR UTILIZATION

(71) Applicant: The Board of Trustees of the University of Illinois, Urbana, IL (US)

(72) Inventors: Yong-Su Jin, Champaign, IL (US); Stephan Thomas Lane, Bloomington, IL (US); Haiqing Xu, Ann Arbor, MI (US); Soo-Rin Kim, Daegu (KR)

(73) Assignee: BOARD OF TRUSTEES OF THE UNIVERSITY OF ILLINOIS, Ubana, IL (US)

( * ) Notice: Subject to any disclaimer, the term of this patent is extended or adjusted under 35 U.S.C. 154(b) by 0 days.

(21) Appl. No.: 15/708,262

(22) Filed: Sep. 19, 2017

Related U.S. Application Data

(60) Provisional application No. 62/396,488, filed on Sep. 19, 2016.

(51) Int. Cl.
| | |
|---|---|
| *C12N 15/81* | (2006.01) |
| *C12N 1/26* | (2006.01) |
| *C12N 9/12* | (2006.01) |
| *C12P 7/06* | (2006.01) |

(52) U.S. Cl.
CPC .............. *C12N 15/81* (2013.01); *C12N 1/26* (2013.01); *C12N 9/1258* (2013.01); *C12P 7/06* (2013.01)

(58) Field of Classification Search
None
See application file for complete search history.

(56) References Cited

U.S. PATENT DOCUMENTS

| | | | | |
|---|---|---|---|---|
| 8,647,855 | B2* | 2/2014 | Taron ........................ | C12P 7/06 435/161 |
| 2014/0057323 | A1* | 2/2014 | Doudna Cate ... | C12Y 204/0102 435/97 |

OTHER PUBLICATIONS

Jiang et al. Multigene editing in the *Escherichia coli* genome via the CRISPR-Cas9 system, Appl and Environ Microbiol 81(7): 2506-2514, 2015 (EPub Jan. 30, 2015).*
Rodriguez et al. The hexokinase 2 protein regulates the expression of the GLK1, HXK1 and HXK2 genes of *Saccharomyces cerevisiae*. Biochem J. (2001), 355: 625-631.*
Yin et al. FEMMS Microbiology Letters, 362, p. 1-7, internal, 2015, Epub Dec. 8, 2014.*
De Winde et al. Differential requirement of the yeast sugar kinases for sugar sensing in establishing the catabolite-repressed state. Eur. J. Biochem. 241, 633-643 (1996).*
Lin et al. Leveraging transcription factors to speed cellobiose fermentation by *Saccharomyces cerevisiae*. Biotechnology for Biofuels 2014, 7:126.*

Kim et al., "Simultaneous co-fermentation of mixed sugars: a promising strategy for producing cellulosic ethanol", Trends Biotechnol, 30(5):274-282 (2012).
Ha et al., "Engineered *Saccharomyces cerevisiae* capable of simultaneous cellobiose and xylose fermentation", Proc Natl Acad Sci USA, 108(2):504-509 (2011).
Farwick et al., "Engineering of yeast hexose transporters to transport D-xylose without inhibition by D-glucose", Proceedings of the National Academy of Sciences, 111(14):5159-5164 (2014).
Shin, et al. "An engineered cryptic Hxt11 sugar transporter facilitates glucose-xylose co-consumption in *Saccharomyces cerevisiae*", Biotechnology for biofuels, 8(1):1 (2015).
Wang et al., "Directed evolution of xylose specific transporters to facilitate glucose-xylose co-utilization", Biotechnology and bioengineering, vol. 113, p. 484-491 (2015).
Escalante-Chong et at. "Galactose metabolic genes in yeast respond to a ratio of galactose and glucose", Proceedings of the Nationat Academy of Sciences, 112(5):1636-1641 (2015).
Raamsdonk et al., "Co-consumption of sugars or ethanol and glucose in a *Saccharomyces cerevisiae* strain deleted in the HXK2 gene" Yeast, 18(11):1023-1033 (2001).
Ostergaard et al., "The impact of GAL6, GAL80, and MIG1 on glucose control of the GAL system in *Saccharomyces cerevisiae*", FEMS yeast research 1(1):47-55 (2001).
Katahira et al., "Ethanol fermentation from lignocellulosic hydrolysate by a recombinant xylose- and cellooligosaccharide-assimilating yeast strain", Appl Microbiol Biotechnol 72(6):1136-1143 (2006).
Ho et al., "Genetically engineered *Saccharomyces* yeast capable of effective cofermentation of glucose and xylose", Appl Environ Microbiol, 64(5):1852-1859 (1998).
Ahuatzi et al., "Hxk2 regulates the phosphorylation state of Mig1 and therefore its nucleocytoplasmic distribution", Journal of Biological Chemistry 282(7):4485-4493 (2007).
Bae et al., "Deletion of the HXK2 gene in *Saccharomyces cerevisiae* enables mixed sugar fermentation of glucose and galactose in oxygen-limited conditions", Process Biochemistry 49(4):547-553 (2014).
Nijland et al., "Engineering of an endogenous hexose transporter into a specific D-xylose transporter facilitates glucose-xylose co-consumption in *Saccharomyces cerevisiae*" Biotechnology for biofuels 7(1):168 (2014).
Cairey-Remonnay et al., "Glycolysis Controls Plasma Membrane Glucose Sensors to Promote Glucose Signaling in Yeasts", Molecular and cellular biology 35(4):747-757 (2015).

(Continued)

*Primary Examiner* — Iqbal H Chowdhury
(74) *Attorney, Agent, or Firm* — DLA Piper LLP

(57) ABSTRACT

The present disclosure provides recombinant microorganisms capable of sugar co-utilization, the recombinant microorganism comprising a genetically altered microorganism (e.g. *S. cerevisiae*) having a lack of, or reduced expression of, or expression of truncated or mutated forms of at least one polypeptide selected from Hxk1, Hxk2, and Glk1. Reduction of the expression or biological activity of Hxk1, Hxk2 and Glk1 leads to reduction in the glucose consumption pathway, allowing the microorganism to co-utilize multiple sugars (e.g. glucose, xylose, galactose) at an improved rate.

26 Claims, 28 Drawing Sheets
(28 of 28 Drawing Sheet(s) Filed in Color)
Specification includes a Sequence Listing.

(56) References Cited

OTHER PUBLICATIONS

Kasahara et al., "Three aromatic amino acid residues critical for galactose transport in yeast Gal2 transporter", Journal of Biological Chemistry 275(6):4422-4428 (2000).
Tan et al., "Controlling Central Carbon Metabolism for Improved Pathway Yields in *Saccharomyces cerevisiae*", ACS synthetic biology, vol. 5:116 (2016).
GenBank KZV10975.1, dated Jul. 26, 2016.
GenBank KZV11659.1, dated Jul. 26, 2016.
GenBank KZV12811.1, dated Jul. 26, 2016.
GenBank X55392.1, dated Apr. 18, 2005.
GenBank XM_001385144.1, dated Jun. 5, 2017.
GenBank XM_001387288.1, dated Jun. 5, 2017.

* cited by examiner

SEQUENCE LISTING

<160> NUMBER OF SEQ ID NOS: 80

<210> SEQ ID NO 1
<211> LENGTH: 1458
<212> TYPE: DNA
<213> ORGANISM: Saccharomyces cerevisiae

<400> SEQUENCE: 1

```
atggttcatt taggtccaaa gaaaccacag gctagaaagg gttccatggc tgatgtgccc        60
aaggaattga tggatgaaat tcatcagttg gaagatatgt ttacagttga cagcgagacc       120
ttgagaaagg ttgttaagca ctttatcgac gaattgaata aaggtttgac aaagaaggga       180
ggtaacattc caatgattcc cggttgggtc atggaattcc aacaggtaa agaatctggt        240 aactatttgg ccattgattt gggtggtact aacttaagag tcgtgttggt caagttgagc       300
ggtaaccata cctttgacac cactcaatcc aagtataaac taccacatga catgagaacc       360
actaagcacc aagaggagtt atggtccttt attgccgact ctttgaagga ctttatggtc       420
gagcaagaat tgctaaacac caaggacacc ttaccattag gtttcacctt ctcgtaccca       480
gcttcccaaa acaagattaa cgaaggtatt ttgcaaagat ggaccaaggg tttcgatatt       540
ccaaatgtcg aaggccacga tgtcgtccca ttgctacaaa acgaaatttc caagagagag       600
ttgcctattg aaattgtagc attgattaat gatactgttg gtactttaat tgcctcatac       660
tacactgacc cagagactaa gatgggtgtg attttcggta ctggtgtcaa cggtgctttc       720
tatgatgttg tttccgatat cgaaaagttg gagggcaaat tagcagacga tattccaagt       780
aactctccaa tggctatcaa ttgtgaatat ggttccttcg ataatgaaca tttggtcttg       840
ccaagaacca agtacgatgt tgctgtcgac gaacaatctc caagacctgg tcaacaagct       900
tttgaaaaga tgacctccgg ttactacttg ggtgaattgt tgcgtctagt gttacttgaa       960
ttaaacgaga agggcttgat gttgaaggat caagatctaa gcaagttgaa acaaccatac      1020
atcatggata cctcctaccc agcaagaatc gaggatgatc catttgaaaa cttggaagat      1080
actgatgaca tcttccaaaa ggactttggt gtcaagacca ctctgccaga acgtaagttg      1140
attagaagac tttgtgaatt gatcggtacc agagctgcta gattagctgt ttgtggtatt      1200
gccgctattt gccaaaagag aggttacaag actggtcaca ttgccgctga cggttctgtc      1260
tataacaaat acccaggttt caaggaagcc gccgctaagg gttgagagaa tatctatgga      1320
tggactggtg acgcaagcaa agatccaatt acgattgttc cagctgagga tggttcaggt      1380
```

```
gcaggtgctg ctgttattgc tgcattgtcc gaaaaaagaa ttgccgaagg taagtctctt    1440
ggtatcattg gcgcttaa                                                   1458

<210> SEQ ID NO 2
<211> LENGTH: 1458
<212> TYPE: DNA
<213> ORGANISM: Artificial Sequence
<220> FEATURE:
<223> OTHER INFORMATION: Mutant HXK1

<400> SEQUENCE: 2
atggttcatt taggtccaaa gaaaccacag gctagaaagg gttccatggc tgatgtgccc      60
aaggaattga tggatgaaat tcatcagttg gaagatatgt ttacagttga cagcgagacc    120
ttgagaaagg ttgttaagca ctttatcgac gaattgaata aaggtttgac aaagaaggga    180
ggtaacattc caatgattcc cggttgggtc atggaattcc caacaggtaa agaatctggt    240
aactatttgg ccattgattt gggtggtact aacttaagag tcgtgttggt caagttgagc    300
ggtaaccata cctttgacac cactcaatcc aagtataaac taccacatga catgagaacc    360
actaagcacc aagaggagtt atggtccttt attgccgact ctttgaagga ctttatggtc    420
gagcaagaat tgctaaacac caaggacacc ttaccattag gtttcaccttct cgtaccca      480 gcttcccaaa acaagattaa cgaaggtatt ttgcaaagat ggaccaaggg tttcgatatt    540
ccaaatgtcg aaggccacga tgtcgtccca ttgctacaaa acgaaatttc caagagagag    600
ttgcctattg aaattgtagc attgattaat gatactgttg gtactttaat tgcctcatac    660
tacactgacc cagagactaa gatgggtgtg atttttcggta ctggtgtcaa cggtgctttc    720
tatgatgttg tttccgatat cgaaaagttg gagggcaaat tagcagacga tattccaagt    780
aactctccaa tggctatcaa ttgtgaatat ggttccttcg ataatgaaca tttggtcttg    840
ccaagaacca agtacgatgt tgctgtcgac gaacaatctc caagacctgg tcaacaagct    900
tttgaaaaga tgacccccgg ttactacttg gtgaattgt tgcgtctagt gttacttgaa    960
ttaaacgaga agggcttgat gttgaaggat caagatctaa gcaagttgaa acaaccatac    1020
atcatggata cctcctaccc agcaagaatc gaggatgatc catttgaaaa cttggaagat    1080
actgatgaca tcttccaaaa ggactttggt gtcaagacca ctctgccaga acgtaagttg    1140
attagaagac tttgtgaatt gatcggtacc agagctgcta gattagctgt ttgtggtatt    1200
gccgctattt gccaaaagag aggttacaag actggtcaca ttgccgctga cggttctgtc    1260
tataacaaat acccaggttt caaggaagcc gccgctaagg gttgagaga tatctatgga    1320 tggactggtg acgcaagcaa agatccaatt acgattgttc agctgaggga tggttcaggt    1380
gcaggtgctg ctgttattgc tgcattgtcc gaaaaaagaa ttgccgaagg taagtctctt    1440
ggtatcattg gcgcttaa                                                   1458

<210> SEQ ID NO 3
<211> LENGTH: 1461
<212> TYPE: DNA
<213> ORGANISM: Saccharomyces cerevisiae

<400> SEQUENCE: 3
atggttcatt taggtccaaa aaaaccacaa gccagaaagg gttccatggc cgatgtgcca      60
aaggaattga tgcaacaaat tgagaatttt gaaaaaattt tcactgttcc aactgaaact    120
ttacaagccg ttaccaagca cttcatttcc gaattggaaa agggtttgtc caagaaggga    180
ggtaacattc caatgattcc aggttgggtt atggatttcc caactggtaa ggaatccggt    240
```

```
gatttcttgg ccattgattt gggtggtacc aacttgagag ttgtcttagt caagttgggc      300
ggtgaccgta cctttgacac cactcaatct aagtacagat taccagatgc tatgagaact      360
actcaaaatc cagacgaatt gtgggaattt attgccgact ctttgaaagc ttttattgat      420
gagcaattcc cacaaggtat ctctgagcca attccattgg gtttcacctt ttcttttccca     480 gcttctcaaa acaaaatcaa tgaaggtatc ttgcaaagat ggactaaagg ttttgatatt      540
ccaaacattg aaaaccacga tgttgttcca atgttgcaaa agcaaatcac taagaggaat      600
atcccaattg aagttgttgc tttgataaac gacactaccg gtactttggt tgcttcttac      660
tacactgacc cagaaactaa gatgggtgtt atcttcggta ctggtgtcaa tggtgcttac      720
tacgatgttt gttccgatat cgaaaagcta caaggaaaac tatctgatga cattccacca      780
tctgctccaa tggccatcaa ctgtgaatac ggttccttcg ataatgaaca tgtcgttttg      840
ccaagaacta aatacgatat caccattgat gaagaatctc caagaccagg ccaacaaacc      900
tttgaaaaaa tgtcttctgg ttactactta ggtgaaattt tgcgtttggc cttgatggac      960
atgtacaaac aaggtttcat cttcaagaac caagacttgt ctaagttcga caagcctttc     1020
gtcatggaca cttcttaccc agccagaatc gaggaagatc cattcgagaa cctagaagat     1080
accgatgact tgttccaaaa tgagttcggt atcaacacta ctgttcaaga cgtaaaattg     1140
atcagacgtt tatctgaatt gattggtgct agagctgcta gattgtccgt ttgtggtatt     1200
gctgctatct gtcaaaagag aggttacaag accggtcaca tcgctgcaga cggttccgtt     1260
tacaacagat acccaggttt caaagaaaag gctgccaatg ctttgaagga catttacggc     1320
tggactcaaa cctcactaga cgactaccca atcaagattg ttcctgctga agatggttcc     1380
ggtgctggtg ccgctgttat tgctgctttg gcccaaaaaa gaattgctga aggtaagtcc     1440
gttggtatca tcggtgctta a                                                1461

<210> SEQ ID NO 4
<211> LENGTH: 269
<212> TYPE: DNA
<213> ORGANISM: Artificial Sequence
<220> FEATURE:
<223> OTHER INFORMATION: Synthetic oligonucleotide

<400> SEQUENCE: 4
tctttgaaaa gataatgtat gattatgctt tcactcatat ttatacagaa acttgatgtt       60
ttctttcgag tatatacaag gtgattacat gtacgtttga agtacaactc tagattttgt      120
agtgccctct tgggctagcg gtaaaggtgc cattttttc acaccctaca atgttctgtt      180
caaaagattt tggtcaaacg ctgtagaagt gaaagttggt gcgcatgttt cggcgttcga      240
aacttctccg cagtgaaaga taaatgatc                                        269

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
ttcacccaag tagtaaccgg                                                   20

<210> SEQ ID NO 6
<211> LENGTH: 20
<212> TYPE: DNA
<213> ORGANISM: Artificial Sequence
```

```
<220> FEATURE:
<223> OTHER INFORMATION: Synthetic oligonucleotide

<400> SEQUENCE: 6
aacagaacat atacggaaat                                                   20

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
gttcctgctg aagatggttc                                                   20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
caaagccaat cgccgcatat                                                   20

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
tgatagagtt gtattagtgg                                                   20

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
tagtttatac ttggattgag                                                   20

<210> SEQ ID NO 11
<211> LENGTH: 79
<212> TYPE: DNA
<213> ORGANISM: Artificial Sequence
<220> FEATURE:
<223> OTHER INFORMATION: Synthetic oligonucleotide

<400> SEQUENCE: 11
gttttagagc tagaaatagc aagttaaaat aaggctagtc cgttatcaac ttgaaaaagt       60
ggcaccgagt cggtggtgc                                                    79

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide
```

<400> SEQUENCE: 12
tttttttgtt ttttatgtct                                        20

<210> SEQ ID NO 13
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 13
caaagccaat cgccgcatat gttttagagc tagaaatagc aagttaaa         48

<210> SEQ ID NO 14
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 14
acatatgcgg cgattggctt tggatcattt atctttcact gcgga            45

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
caaagccaat cgccgcatat                                        20

<210> SEQ ID NO 16
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 16
ggagcgcggt gttttactag ccgccgacct gggtggtgct aatttccgta tatgttctgt    60

<210> SEQ ID NO 17
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 17
catttgctcc atggagaaag tatgatctcc atgcaagtta acagaacata tacggaaatt    60

<210> SEQ ID NO 18
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 18
ggcggatcca tgtcattcga cgacttacac aa                          32

```
<210> SEQ ID NO 19
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 19
gacttacctt cagcaattct tttttgggcc aaagcagcaa taacagcggc accagcactg    60

<210> SEQ ID NO 20
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 20
ggcggatcct tagcactact gggacaagc                                      29

<210> SEQ ID NO 21
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 21
ggcgcggccg cgaggaagtg tagagagggt t                                   31

<210> SEQ ID NO 22
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 22
atctccaaga cctggtcaac aagcttttga aaagatgact ccaggttact acttgggtga    60

<210> SEQ ID NO 23
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 23
gcccttctcg tttaattcaa gtaacactag acgcaacaat tcacccaagt agtaacctgg    60

<210> SEQ ID NO 24
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 24
gccggatccc acctggtctt acctcgaac                                      29

<210> SEQ ID NO 25
<211> LENGTH: 31
<212> TYPE: DNA
<213> ORGANISM: Artificial Sequence
<220> FEATURE:
<223> OTHER INFORMATION: Synthetic oligonucleotide
```

<400> SEQUENCE: 25
gccgcggccg ccgactttct ccctctctcc a                           31

<210> SEQ ID NO 26
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 26
gttgacaggt cagttaaggc acag                                   24

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 27
gttgatcatc gagtcgctcg                                        20

<210> SEQ ID NO 28
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 28
tctcaattcc tcttatatta gattataaga acaacaaatt aaattacaaa aagacttata    60
aagcaacata cgagcgactc gatgatcaac                                    90

<210> SEQ ID NO 29
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 29
gaagatcatc tattaaagta ttagtagcca ttagccttaa aaaaatcagt gctagtttaa    60
gtataatctc gttgatcatc gagtcgctcg                                    90

<210> SEQ ID NO 30
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 30
aatagaatca caaacaaaat ttacatctga gttaaacaat ccagctgaag cttcgtacgc    60

<210> SEQ ID NO 31
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 31
aaatacacta ttattcagca ctacggttta gcgtgaaagc ataggccact agtggatctg    60

```
<210> SEQ ID NO 32
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 32
ggtttggttt tgaaacactt ttacaataaa atctgccaaa acagctgaag cttcgtacgc    60

<210> SEQ ID NO 33
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 33
attccttgaa ggaagtctat attatttaat taactgacgc ataggccact agtggatctg    60

<210> SEQ ID NO 34
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 34
aacatataaa aagagctcga gaaaagacat atggtttgta actatcttct tcttttttcc    60 aattttctg tcagctgaag cttcgtacgc                                       90

<210> SEQ ID NO 35
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 35
ttctgagaac aaatgatcaa aaacttgaaa attaaactgt attattttgt atatattaaa    60
aacgtattgc ataggccact agtggatctg                                      90

<210> SEQ ID NO 36
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 36
ggatgtatgg gctaaatg                                                   18

<210> SEQ ID NO 37
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 37
attcggttaa actctcgg                                                   18
```

```
<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 38
ttcatgaaaa attccagagt                                              20

<210> SEQ ID NO 39
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 39
gcgccaagac aaatgtttc                                               19

<210> SEQ ID NO 40
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 40
cccccccatc agtgcccaac tcagcttccg taaaccacaa caaaagcgcc agttcatttg   60

<210> SEQ ID NO 41
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 41
tctctcagtg gctttgtgta agtcgtcgaa tgacatgtgt gtatttgtgt ttgtgtg      57

<210> SEQ ID NO 42
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 42
cccatcagtg cccaactcag cttccgtaaa ccacaacaaa tgtttctact cctttttac    60

<210> SEQ ID NO 43
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 43
ctcagtggct ttgtgtaagt cgtcgaatga cattttgtaa ttaaaactta gattagattg   60

<210> SEQ ID NO 44
<211> LENGTH: 60
<212> TYPE: DNA
<213> ORGANISM: Artificial Sequence
<220> FEATURE:
<223> OTHER INFORMATION: Synthetic oligonucleotide
```

<400> SEQUENCE: 44
gcgtaacaaa atatatatat atatatatat atatatgtat gtcacgcaaa agaaaacctt    60

<210> SEQ ID NO 45
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 45
tctctcagtg gctttgtgta agtcgtcgaa tgacattatt gatatagtgt ttaagcgaat    60

<210> SEQ ID NO 46
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 46
tataagtggt gtgccgacg                                                 19

<210> SEQ ID NO 47
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 47
gatgaccgct ctctcagtgg                                                20

<210> SEQ ID NO 48
<211> LENGTH: 88
<212> TYPE: DNA
<213> ORGANISM: Artificial Sequence
<220> FEATURE:
<223> OTHER INFORMATION: Synthetic oligonucleotide

<400> SEQUENCE: 48
caattagaat tcttttcttt taatcaaact cacccaaaca actcaattag aatactgaaa    60
aaataagatg cgtacgctgc aggtcgac                                       88

<210> SEQ ID NO 49
<211> LENGTH: 89
<212> TYPE: DNA
<213> ORGANISM: Artificial Sequence
<220> FEATURE:
<223> OTHER INFORMATION: Synthetic oligonucleotide

<400> SEQUENCE: 49
atcactcata agaataataa tattaaggga gggaaaaaca catttatatt tcattacatt    60
tttttcatta atcgatgaat tcgagctcg                                      89

<210> SEQ ID NO 50
<211> LENGTH: 88
<212> TYPE: DNA
<213> ORGANISM: Artificial Sequence
<220> FEATURE:
<223> OTHER INFORMATION: Synthetic oligonucleotide

```
<400> SEQUENCE: 50
gcttttcctt tgaaaaggtt gtaggaatat aattctccac acataataag tacgctaatt    60
aaataaaatg cgtacgctgc aggtcgac                                       88

<210> SEQ ID NO 51
<211> LENGTH: 89
<212> TYPE: DNA
<213> ORGANISM: Artificial Sequence
<220> FEATURE:
<223> OTHER INFORMATION: Synthetic oligonucleotide

<400> SEQUENCE: 51
aaaacatgtt cacataagta gaaaagggc accttcttgt tgttcaaact taatttacaa    60
attaagttta atcgatgaat tcgagctcg                                      89

<210> SEQ ID NO 52
<211> LENGTH: 89
<212> TYPE: DNA
<213> ORGANISM: Artificial Sequence
<220> FEATURE:
<223> OTHER INFORMATION: Synthetic oligonucleotide

<400> SEQUENCE: 52
ccccatcagt gcccaactca gcttccgtaa accacaacac caccactaat acaactctat    60
catacacaag cagctgaagc ttcgtacgc                                      89

<210> SEQ ID NO 53
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 53
tatatataaa ggagagaaga tggtaagtac ggtgggatac gtacacaaac caaaaaatg    60 taaaagagc ataggccact agtggatctg                                      90

<210> SEQ ID NO 54
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 54
ccccatcagt gcccaactca gcttccgtaa accacaacac caccactaat acaactctat    60
catacacaag taaggcgagc tcataccgtc                                     90

<210> SEQ ID NO 55
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 55
tatatatata aaggagagaa gatggtaagt acggtgggat acgtacacaa accaaaaaaa    60
tgtaaaaaga gacggtatga gctcgcctta                                     90
```

```
<210> SEQ ID NO 56
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 56
taccaattag acatgctgct tgc                                             23

<210> SEQ ID NO 57
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 57
gacggtatga gctcgcctta                                                 20

<210> SEQ ID NO 58
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 58
actcaattag aattcttttc ttttaatcaa actcacccaa acaactcaat tagaatactg     60
aaaaaataag gtgtaactca gatgagctac                                      90

<210> SEQ ID NO 59
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 59
ggcatcactc ataagaataa taatattaag ggagggaaaa acacatttat atttcattac     60 attttttca gtagctcatc tgagttacac                                       90

<210> SEQ ID NO 60
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 60
gccagatctc agtatagcag                                                 20

<210> SEQ ID NO 61
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 61
gtagctcatc tgagttacac                                                 20
```

```
<210> SEQ ID NO 62
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 62
ggcgtcgact catgctacaa gcgcacaca                                    29

<210> SEQ ID NO 63
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 63
ttcgcttttt ctttgaaaag gttgtaggaa tataattctc cacacataat aagtacgcta    60
attaaataaa acgaccgacg tacgattcaa                                    90

<210> SEQ ID NO 64
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 64
tagaaaacat gttcacataa gtagaaaaag ggcaccttct tgttgttcaa acttaattta    60
caaattaagt ttgaatcgta cgtcggtcgt                                    90

<210> SEQ ID NO 65
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 65
gctccagagc tccacattg                                               19

<210> SEQ ID NO 66
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 66
ttgaatcgta cgtcggtcgt                                              20

<210> SEQ ID NO 67
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 67 aaatttttaga cgcggcgctt gcaccccgca ttataagtgg tgctcaagca aggttttcag   60
```

-continued

```
<210> SEQ ID NO 68
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 68
taccggtacc gaaaatacat ccgatgaccg gctccgagga attccactta atgtatcaac      60

<210> SEQ ID NO 69
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 69
gtgtcactag gtgcaattgc c                                               21

<210> SEQ ID NO 70
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 70
cgacagcact tcggatga                                                   18

<210> SEQ ID NO 71
<211> LENGTH: 1473
<212> TYPE: DNA
<213> ORGANISM: Artificial Sequence
<220> FEATURE:
<223> OTHER INFORMATION: Mutant HXK2

<400> SEQUENCE: 71
atggttcatt taggtccaaa aaaaccacaa gccagaaagg gttccatggc cgatgtgcca      60
aaggaattga tgcaacaaat tgagaatttt gaaaaatttt tcactgttcc aactgaaact    120
ttacaagccg ttaccaagca cttcattttcc gaattggaaa agggtttgtc caagaagggt    180
ggtaacattc caatgattcc aggttgggtt atggatttcc caactggtaa ggaatccggt    240
gatttcttgg ccattgattt gggtggtacc aacttgagag ttgtcttagt caagttgggc    300
ggtgaccgta cctttgacac cactcaatct aagtacagat taccagatgc tatgagaact    360
actcaaaatc cagacgaatt gtgggaattt attgccgact cttttgaaagc ttttattgat    420 gagcaattcc cacaaggtat ctctgagcca attccattgg gtttcacctt ttctttccca    480
gcttctcaaa acaaaatcaa tgaaggtatc ttgcaaagat ggactaaagg ttttgatatt    540
ccaaacattg aaaaccacga tgttgttcca atgttgcaaa agcaaatcac taagaggaat    600
atcccaattg aagttgttgc tttgataaac gacactaccg gtactttggt tgcttcttac    660
tacactgacc cagaaactaa gatgggtgtt atcttcggta ctggtgtcaa tggtgcttac    720
tacgatgttt gttccgatat cgaaaagcta caaggaaaac tatctgatga cattccacca    780
tctgctccaa tggccatcaa ctgtgaatac ggttccttcg ataatgaaca tgtcgttttg    840
ccaagaacta aatacgatat caccattgat gaagaatctc caagaccagg ccaacaaacc    900
tttgaaaaaa tgtcttctgg ttactactta ggtgaaattt tgcgtttggc cttgatggac    960
```

| | |
|---|---|
| atgtacaaac aaggtttcat cttcaagaac caagacttgt ctaagttcga caagcctttc | 1020 |
| gtcatggaca cttcttaccc agccagaatc gaggaagatc cattcgagaa cctagaagat | 1080 |
| accgatgact tgttccaaaa tgagttcggt atcaacacta ctgttcaaga acgtaaattg | 1140 |
| atcagacgtt tatctgaatt gattggtgct agagctgcta gattgtccgt ttgtggtatt | 1200 |
| gctgctatct gtcaaaagag aggttacaag accggtcaca tcgctgcaga cggttccgtt | 1260 |
| tacaacagat acccaggttt caagaaaaag gctgccaatg ctttgaagga catttacggc | 1320 |
| tggactcaaa cctcactaga cgactaccca atcaagattg ttctgctgaa gatggttccg | 1380 |
| gtgctggtgc cgctgttatt gctgctttgg cccaaaaaag aattgctgaa ggtaagtccg | 1440 |
| ttggtatcat cggtgcttaa acttaatttg taa | 1473 |

<210> SEQ ID NO 72
<211> LENGTH: 1503
<212> TYPE: DNA
<213> ORGANISM: Saccharomyces cerevisiae

<400> SEQUENCE: 72

| | |
|---|---|
| atgtcattcg acgacttaca caaagccact gagagagcgg tcatccaggc cgtggaccag | 60 |
| atctgcgacg atttcgaggt tacccccgag aagctggacg aattaactgc ttacttcatc | 120 |
| gaacaaatgg aaaaaggtct agctccacca aaggaaggcc acacattggc ctcggacaaa | 180 |
| ggtcttccta tgattccggc gttcgtcacc gggtcaccca acgggacgga gcgcggtgtt | 240 |
| ttactagccg ccgacctggg tggtaccaat ttccgtatat gttctgttaa cttgcatgga | 300 |
| gatcatactt tctccatgga gcaaatgaag tccaagattc ccgatgattt gctagacgat | 360 |
| gagaacgtca catctgacga cctgtttggg tttctagcac gtcgtacact ggcctttatg | 420 |
| aagaagtatc acccggacga gttggccaag ggtaaagacg ccaagcccat gaaactgggg | 480 |
| ttcactttct catacctgt agaccagacc tctctaaact ccgggacatt gatccgttgg | 540 |
| accaagggtt tccgcatcgc ggacaccgtc ggaaaggatg tcgtgcaatt gtaccaggag | 600 |
| caattaagcg ctcagggtat gcctatgatc aaggttgttg cattaaccaa cgacaccgtc | 660 |
| ggaacgtacc tatcgcattg ctacacgtcc gataacacgg actcaatgac gtccggagaa | 720 |
| atctcggagc cggtcatcgg atgtattttc ggtaccggta ccaatgggtg ctatatggag | 780 |
| gagatcaaca agatcacgaa gttgccacag gagttgcgtg acaagttgat aaaggagggt | 840 |
| aagacacaca tgatcatcaa tgtcgaatgg gggtccttcg ataatgagct caagcacttg | 900 |
| cctactacta gtatgacgt cgtaattgac cagaaactgt caacgaaccc gggatttcac | 960 |
| ttgtttgaaa acgtgtctc agggatgttc ttgggtgagg tgttgcgtaa cattttagtg | 1020 |
| gacttgcact cgcaaggctt gcttttgcaa cagtacaggt ccaaggaaca acttcctcgc | 1080 |
| cacttgacta caccttttcca gttgtcatcc gaagtgctgt cgcatattga aattgacgac | 1140 |
| tcgacaggtc tacgtgaaac agagttgtca ttattacaga gtctcagact gcccaccact | 1200 |
| ccaacagagc gtgttcaaat tcaaaaattg gtgcgcgcga tttctaggag atctgcgtat | 1260 |
| ttagccgccg tgccgcttgc cgcgatattg atcaagacaa atgctttgaa caagagatat | 1320 |
| catggtgaag tcgagatcgg ttgtgatggt tccgttgtgg aatactaccc cggtttcaga | 1380 |
| tctatgctga gacacgcctt agccttgtca cccttgggtg ccgagggtga gaggaaggtg | 1440 |
| cacttgaaga ttgccaagga tggttccgga gtgggtgccg ccttgtgtgc gcttgtagca | 1500 |
| tga | 1503 |

<210> SEQ ID NO 73
<211> LENGTH: 1503
<212> TYPE: DNA
<213> ORGANISM: Artificial Sequence
<220> FEATURE:
<223> OTHER INFORMATION: Mutant GLK1

<400> SEQUENCE: 73

```
atgtcattcg acgacttaca caaagccact gagagagcgg tcatccaggc cgtggaccag      60
atctgcgacg atttcgaggt taccccgag aagctggacg aattaactgc ttacttcatc     120
gaacaaatgg aaaaaggtct agctccacca aaggaaggcc acacattggc ctcggacaaa    180
ggtcttccta tgattccggc gttcgtcacc gggtcaccca acgggacgga gcgcggtgtt    240
ttactagccg ccgacctggg tggtgccaat tccgtatat gttctgttaa cttgcatgga    300
gatcatactt tctccatgga gcaaatgaag tccaagattc ccgatgattt gctagacgat    360
gagaacgtca catctgacga cctgtttggg tttctagcac gtcgtacact ggcctttatg    420
aagaagtatc acccggacga gttggccaag ggtaaagacg ccaagcccat gaaactgggg    480
ttcactttct catacctgt agaccagacc tctctaaact ccgggacatt gatccgttgg    540
accaaggggt tccgcatcgc ggacaccgtc ggaaaggatg tcgtgcaatt gtaccaggag    600
caattaagcg ctcagggtat gcctatgatc aaggttgttg cattaaccaa cgacaccgtc    660
ggaacgtacc tatcgcattg ctacacgtcc gataacacgg actcaatgac gtccggagaa    720
atctcggagc cggtcatcgg atgtattttc ggtaccggta ccaatgggtg ctatatggag    780
gagatcaaca agatcacgaa gttgccacag gagttgcgtg acaagttgat aaaggagggt    840
aagacacaca tgatcatcaa tgtcgaatgg gggtccttcg ataatgagct caagcacttg    900
cctactacta gtatgacgt cgtaattgac cagaaactgt caacgaaccc gggatttcac    960
ttgtttgaaa acgtgtctc agggatgttc ttgggtgagg tgttgcgtaa cattttagtg   1020
gacttgcact cgcaaggctt gcttttgcaa cagtacaggt ccaaggaaca acttcctcgc   1080
cacttgacta caccttcca gttgtcatcc gaagtgctgt cgcatattga aattgacgac   1140
tcgacaggtc tacgtgaaac agagttgtca ttattacaga gtctcagact gcccaccact   1200
ccaacagagc gtgttcaaat tcaaaaattg gtgcgcgcga tttctaggag atctgcgtat   1260
ttagccgccg tgccgcttgc cgcgatattg atcaagacaa atgctttgaa caagagatat   1320
catggtgaag tcgagatcgg ttgtgatggt tccgttgtgg aatactaccc cggtttcaga   1380
tctatgctga gacacgcctt agccttgtca cccttgggtg ccgagggtga gaggaaggtg   1440
cacttgaaga ttgccaagga tggttccgga gtgggtgccg ccttgtgtgc gcttgtagca   1500
tga                                                                  1503
```

<210> SEQ ID NO 74
<211> LENGTH: 485
<212> TYPE: PRT
<213> ORGANISM: Saccharomyces cerevisiae

<400> SEQUENCE: 74

```
Met Val His Leu Gly Pro Lys Lys Pro Gln Ala Arg Lys Gly Ser Met
1               5                   10                  15

Ala Asp Val Pro Lys Glu Leu Met Asp Glu Ile His Gln Leu Glu Asp
            20                  25                  30

Met Phe Thr Val Asp Ser Glu Thr Leu Arg Lys Val Val Lys His Phe
        35                  40                  45
```

```
Ile Asp Glu Leu Asn Lys Gly Leu Thr Lys Lys Gly Gly Asn Ile Pro
 50                  55                  60

Met Ile Pro Gly Trp Val Met Glu Phe Pro Thr Gly Lys Glu Ser Gly
 65                  70                  75                  80

Asn Tyr Leu Ala Ile Asp Leu Gly Gly Thr Asn Leu Arg Val Val Leu
                 85                  90                  95

Val Lys Leu Ser Gly Asn His Thr Phe Asp Thr Thr Gln Ser Lys Tyr
            100                 105                 110

Lys Leu Pro His Asp Met Arg Thr Lys His Gln Glu Glu Leu Trp
        115                 120                 125

Ser Phe Ile Ala Asp Ser Leu Lys Asp Phe Met Val Glu Gln Glu Leu
130                 135                 140

Leu Asn Thr Lys Asp Thr Leu Pro Leu Gly Phe Thr Phe Ser Tyr Pro
145                 150                 155                 160

Ala Ser Gln Asn Lys Ile Asn Glu Gly Ile Leu Gln Arg Trp Thr Lys
                165                 170                 175

Gly Phe Asp Ile Pro Asn Val Glu Gly His Asp Val Val Pro Leu Leu
            180                 185                 190

Gln Asn Glu Ile Ser Lys Arg Glu Leu Pro Ile Glu Ile Val Ala Leu
            195                 200                 205

Ile Asn Asp Thr Val Gly Thr Leu Ile Ala Ser Tyr Tyr Thr Asp Pro
210                 215                 220

Glu Thr Lys Met Gly Val Ile Phe Gly Thr Gly Val Asn Gly Ala Phe
225                 230                 235                 240

Tyr Asp Val Val Ser Asp Ile Glu Lys Leu Glu Gly Lys Leu Ala Asp
                245                 250                 255

Asp Ile Pro Ser Asn Ser Pro Met Ala Ile Asn Cys Glu Tyr Gly Ser
            260                 265                 270

Phe Asp Asn Glu His Leu Val Leu Pro Arg Thr Lys Tyr Asp Val Ala
        275                 280                 285

Val Asp Glu Gln Ser Pro Arg Pro Gly Gln Gln Ala Phe Glu Lys Met
290                 295                 300

Thr Ser Gly Tyr Tyr Leu Gly Glu Leu Leu Arg Leu Val Leu Leu Glu
305                 310                 315                 320

Leu Asn Glu Lys Gly Leu Met Leu Lys Asp Gln Asp Leu Ser Lys Leu
                325                 330                 335

Lys Gln Pro Tyr Ile Met Asp Thr Ser Tyr Pro Ala Arg Ile Glu Asp
            340                 345                 350

Asp Pro Phe Glu Asn Leu Glu Asp Thr Asp Asp Ile Phe Gln Lys Asp
        355                 360                 365

Phe Gly Val Lys Thr Thr Leu Pro Glu Arg Lys Leu Ile Arg Arg Leu
370                 375                 380

Cys Glu Leu Ile Gly Thr Arg Ala Ala Arg Leu Ala Val Cys Gly Ile
385                 390                 395                 400

Ala Ala Ile Cys Gln Lys Arg Gly Tyr Lys Thr Gly His Ile Ala Ala
                405                 410                 415

Asp Gly Ser Val Tyr Asn Lys Tyr Pro Gly Phe Lys Glu Ala Ala Ala
            420                 425                 430

Lys Gly Leu Arg Asp Ile Tyr Gly Trp Thr Gly Asp Ala Ser Lys Asp
        435                 440                 445

Pro Ile Thr Ile Val Pro Ala Glu Asp Gly Ser Gly Ala Gly Ala Ala
450                 455                 460
```

Val Ile Ala Ala Leu Ser Glu Lys Arg Ile Ala Glu Gly Lys Ser Leu
465                 470                 475                 480

Gly Ile Ile Gly Ala
            485

<210> SEQ ID NO 75
<211> LENGTH: 485
<212> TYPE: PRT
<213> ORGANISM: Artificial Sequence
<220> FEATURE:
<223> OTHER INFORMATION: Mutant HXK1 protein

<400> SEQUENCE: 75

Met Val His Leu Gly Pro Lys Lys Pro Gln Ala Arg Lys Gly Ser Met
1               5                   10                  15

Ala Asp Val Pro Lys Glu Leu Met Asp Glu Ile His Gln Leu Glu Asp
                20                  25                  30

Met Phe Thr Val Asp Ser Glu Thr Leu Arg Lys Val Val Lys His Phe
            35                  40                  45

Ile Asp Glu Leu Asn Lys Gly Leu Thr Lys Lys Gly Gly Asn Ile Pro
        50                  55                  60

Met Ile Pro Gly Trp Val Met Glu Phe Pro Thr Gly Lys Glu Ser Gly
65                  70                  75                  80

Asn Tyr Leu Ala Ile Asp Leu Gly Gly Thr Asn Leu Arg Val Val Leu
                85                  90                  95

Val Lys Leu Ser Gly Asn His Thr Phe Asp Thr Thr Gln Ser Lys Tyr
            100                 105                 110

Lys Leu Pro His Asp Met Arg Thr Thr Lys His Gln Glu Glu Leu Trp
        115                 120                 125

Ser Phe Ile Ala Asp Ser Leu Lys Asp Phe Met Val Glu Gln Glu Leu
130                 135                 140

Leu Asn Thr Lys Asp Thr Leu Pro Leu Gly Phe Thr Phe Ser Tyr Pro
145                 150                 155                 160

Ala Ser Gln Asn Lys Ile Asn Glu Gly Ile Leu Gln Arg Trp Thr Lys
                165                 170                 175

Gly Phe Asp Ile Pro Asn Val Glu Gly His Asp Val Val Pro Leu Leu
            180                 185                 190

Gln Asn Glu Ile Ser Lys Arg Glu Leu Pro Ile Glu Ile Val Ala Leu
        195                 200                 205

Ile Asn Asp Thr Val Gly Thr Leu Ile Ala Ser Tyr Tyr Thr Asp Pro
210                 215                 220

Glu Thr Lys Met Gly Val Ile Phe Gly Thr Gly Val Asn Gly Ala Phe
225                 230                 235                 240

Tyr Asp Val Val Ser Asp Ile Glu Lys Leu Glu Gly Lys Leu Ala Asp
                245                 250                 255

Asp Ile Pro Ser Asn Ser Pro Met Ala Ile Asn Cys Glu Tyr Gly Ser
            260                 265                 270

Phe Asp Asn Glu His Leu Val Leu Pro Arg Thr Lys Tyr Asp Val Ala
        275                 280                 285

Val Asp Glu Gln Ser Pro Arg Pro Gly Gln Gln Ala Phe Glu Lys Met
290                 295                 300

Thr Pro Gly Tyr Tyr Leu Gly Glu Leu Leu Arg Leu Val Leu Leu Glu
305                 310                 315                 320

Leu Asn Glu Lys Gly Leu Met Leu Lys Asp Gln Asp Leu Ser Lys Leu
                325                 330                 335

```
Lys Gln Pro Tyr Ile Met Asp Thr Ser Tyr Pro Ala Arg Ile Glu Asp
                340                 345                 350

Asp Pro Phe Glu Asn Leu Glu Asp Thr Asp Asp Ile Phe Gln Lys Asp
                355                 360                 365

Phe Gly Val Lys Thr Thr Leu Pro Glu Arg Lys Leu Ile Arg Arg Leu
            370                 375                 380

Cys Glu Leu Ile Gly Thr Arg Ala Ala Arg Leu Ala Val Cys Gly Ile
385                 390                 395                 400

Ala Ala Ile Cys Gln Lys Arg Gly Tyr Lys Thr Gly His Ile Ala Ala
                405                 410                 415

Asp Gly Ser Val Tyr Asn Lys Tyr Pro Gly Phe Lys Glu Ala Ala Ala
            420                 425                 430

Lys Gly Leu Arg Asp Ile Tyr Gly Trp Thr Gly Asp Ala Ser Lys Asp
            435                 440                 445

Pro Ile Thr Ile Val Pro Ala Glu Asp Gly Ser Gly Ala Gly Ala Ala
            450                 455                 460

Val Ile Ala Ala Leu Ser Glu Lys Arg Ile Ala Glu Gly Lys Ser Leu
465                 470                 475                 480

Gly Ile Ile Gly Ala
            485

<210> SEQ ID NO 76
<211> LENGTH: 486
<212> TYPE: PRT
<213> ORGANISM: Saccharomyces cerevisiae

<400> SEQUENCE: 76

Met Val His Leu Gly Pro Lys Lys Pro Gln Ala Arg Lys Gly Ser Met
1               5                   10                  15

Ala Asp Val Pro Lys Glu Leu Met Gln Gln Ile Glu Asn Phe Glu Lys
                20                  25                  30

Ile Phe Thr Val Pro Thr Glu Thr Leu Gln Ala Val Thr Lys His Phe
            35                  40                  45

Ile Ser Glu Leu Glu Lys Gly Leu Ser Lys Lys Gly Gly Asn Ile Pro
        50                  55                  60

Met Ile Pro Gly Trp Val Met Asp Phe Pro Thr Gly Lys Glu Ser Gly
65                  70                  75                  80

Asp Phe Leu Ala Ile Asp Leu Gly Gly Thr Asn Leu Arg Val Val Leu
                85                  90                  95

Val Lys Leu Gly Gly Asp Arg Thr Phe Asp Thr Thr Gln Ser Lys Tyr
            100                 105                 110

Arg Leu Pro Asp Ala Met Arg Thr Thr Gln Asn Pro Asp Glu Leu Trp
        115                 120                 125

Glu Phe Ile Ala Asp Ser Leu Lys Ala Phe Ile Asp Glu Gln Phe Pro
    130                 135                 140

Gln Gly Ile Ser Glu Pro Ile Pro Leu Gly Phe Thr Phe Ser Phe Pro
145                 150                 155                 160

Ala Ser Gln Asn Lys Ile Asn Glu Gly Ile Leu Gln Arg Trp Thr Lys
                165                 170                 175

Gly Phe Asp Ile Pro Asn Ile Glu Asn His Asp Val Val Pro Met Leu
            180                 185                 190

Gln Lys Gln Ile Thr Lys Arg Asn Ile Pro Ile Glu Val Val Ala Leu
        195                 200                 205

Ile Asn Asp Thr Thr Gly Thr Leu Val Ala Ser Tyr Tyr Thr Asp Pro
    210                 215                 220
```

-continued

Glu Thr Lys Met Gly Val Ile Phe Gly Thr Gly Val Asn Gly Ala Tyr
225                 230                 235                 240

Tyr Asp Val Cys Ser Asp Ile Glu Lys Leu Gln Gly Lys Leu Ser Asp
            245                 250                 255

Asp Ile Pro Pro Ser Ala Pro Met Ala Ile Asn Cys Glu Tyr Gly Ser
            260                 265                 270

Phe Asp Asn Glu His Val Val Leu Pro Arg Thr Lys Tyr Asp Ile Thr
            275                 280                 285

Ile Asp Glu Glu Ser Pro Arg Pro Gly Gln Gln Thr Phe Glu Lys Met
            290                 295                 300

Ser Ser Gly Tyr Tyr Leu Gly Glu Ile Leu Arg Leu Ala Leu Met Asp
305                 310                 315                 320

Met Tyr Lys Gln Gly Phe Ile Phe Lys Asn Gln Asp Leu Ser Lys Phe
                325                 330                 335

Asp Lys Pro Phe Val Met Asp Thr Ser Tyr Pro Ala Arg Ile Glu Glu
            340                 345                 350

Asp Pro Phe Glu Asn Leu Glu Asp Thr Asp Asp Leu Phe Gln Asn Glu
            355                 360                 365

Phe Gly Ile Asn Thr Thr Val Gln Glu Arg Lys Leu Ile Arg Arg Leu
370                 375                 380

Ser Glu Leu Ile Gly Ala Arg Ala Ala Arg Leu Ser Val Cys Gly Ile
385                 390                 395                 400

Ala Ala Ile Cys Gln Lys Arg Gly Tyr Lys Thr Gly His Ile Ala Ala
            405                 410                 415

Asp Gly Ser Val Tyr Asn Arg Tyr Pro Gly Phe Lys Glu Lys Ala Ala
            420                 425                 430

Asn Ala Leu Lys Asp Ile Tyr Gly Trp Thr Gln Thr Ser Leu Asp Asp
            435                 440                 445

Tyr Pro Ile Lys Ile Val Pro Ala Glu Asp Gly Ser Gly Ala Gly Ala
            450                 455                 460

Ala Val Ile Ala Ala Leu Ala Gln Lys Arg Ile Ala Glu Gly Lys Ser
465                 470                 475                 480

Val Gly Ile Ile Gly Ala
                485

<210> SEQ ID NO 77
<211> LENGTH: 490
<212> TYPE: PRT
<213> ORGANISM: Artificial Sequence
<220> FEATURE:
<223> OTHER INFORMATION: Mutant HXK2 protein

<400> SEQUENCE: 77

Met Val His Leu Gly Pro Lys Lys Pro Gln Ala Arg Lys Gly Ser Met
1               5                   10                  15

Ala Asp Val Pro Lys Glu Leu Met Gln Gln Ile Glu Asn Phe Glu Lys
            20                  25                  30

Ile Phe Thr Val Pro Thr Glu Thr Leu Gln Ala Val Thr Lys His Phe
            35                  40                  45

Ile Ser Glu Leu Glu Lys Gly Leu Ser Lys Lys Gly Gly Asn Ile Pro
        50                  55                  60

Met Ile Pro Gly Trp Val Met Asp Phe Pro Thr Gly Lys Glu Ser Gly
65                  70                  75                  80

```
Asp Phe Leu Ala Ile Asp Leu Gly Gly Thr Asn Leu Arg Val Val Leu
                85                  90                  95

Val Lys Leu Gly Gly Asp Arg Thr Phe Asp Thr Thr Gln Ser Lys Tyr
            100                 105                 110

Arg Leu Pro Asp Ala Met Arg Thr Thr Gln Asn Pro Asp Glu Leu Trp
        115                 120                 125

Glu Phe Ile Ala Asp Ser Leu Lys Ala Phe Ile Asp Glu Gln Phe Pro
    130                 135                 140

Gln Gly Ile Ser Glu Pro Ile Pro Leu Gly Phe Thr Phe Ser Phe Pro
145                 150                 155                 160

Ala Ser Gln Asn Lys Ile Asn Glu Gly Ile Leu Gln Arg Trp Thr Lys
                165                 170                 175

Gly Phe Asp Ile Pro Asn Ile Glu Asn His Asp Val Val Pro Met Leu
            180                 185                 190

Gln Lys Gln Ile Thr Lys Arg Asn Ile Pro Ile Glu Val Val Ala Leu
        195                 200                 205

Ile Asn Asp Thr Thr Gly Thr Leu Val Ala Ser Tyr Tyr Thr Asp Pro
    210                 215                 220

Glu Thr Lys Met Gly Val Ile Phe Gly Thr Gly Val Asn Gly Ala Tyr
225                 230                 235                 240

Tyr Asp Val Cys Ser Asp Ile Glu Lys Leu Gln Gly Lys Leu Ser Asp
                245                 250                 255

Asp Ile Pro Pro Ser Ala Pro Met Ala Ile Asn Cys Glu Tyr Gly Ser
            260                 265                 270

Phe Asp Asn Glu His Val Val Leu Pro Arg Thr Lys Tyr Asp Ile Thr
        275                 280                 285

Ile Asp Glu Glu Ser Pro Arg Pro Gly Gln Gln Thr Phe Glu Lys Met
    290                 295                 300

Ser Ser Gly Tyr Tyr Leu Gly Glu Ile Leu Arg Leu Ala Leu Met Asp
305                 310                 315                 320

Met Tyr Lys Gln Gly Phe Ile Phe Lys Asn Gln Asp Leu Ser Lys Phe
                325                 330                 335

Asp Lys Pro Phe Val Met Asp Thr Ser Tyr Pro Ala Arg Ile Glu Glu
            340                 345                 350

Asp Pro Phe Glu Asn Leu Glu Asp Thr Asp Leu Phe Gln Asn Glu
        355                 360                 365

Phe Gly Ile Asn Thr Thr Val Gln Glu Arg Lys Leu Ile Arg Arg Leu
    370                 375                 380

Ser Glu Leu Ile Gly Ala Arg Ala Ala Arg Leu Ser Val Cys Gly Ile
385                 390                 395                 400

Ala Ala Ile Cys Gln Lys Arg Gly Tyr Lys Thr Gly His Ile Ala Ala
                405                 410                 415

Asp Gly Ser Val Tyr Asn Arg Tyr Pro Gly Phe Lys Glu Lys Ala Ala
            420                 425                 430

Asn Ala Leu Lys Asp Ile Tyr Gly Trp Thr Gln Thr Ser Leu Asp Asp
        435                 440                 445

Tyr Pro Ile Lys Ile Val Leu Lys Met Val Pro Val Leu Val Pro
    450                 455                 460

Leu Leu Leu Leu Leu Trp Pro Lys Lys Glu Leu Leu Lys Val Ser Pro
465                 470                 475                 480

Leu Val Ser Ser Val Leu Lys Leu Asn Leu
                485                 490
```

```
<210> SEQ ID NO 78
<211> LENGTH: 500
<212> TYPE: PRT
<213> ORGANISM: Saccharomyces cerevisiae

<400> SEQUENCE: 78

Met Ser Phe Asp Asp Leu His Lys Ala Thr Glu Arg Ala Val Ile Gln
1               5                   10                  15

Ala Val Asp Gln Ile Cys Asp Asp Phe Glu Val Thr Pro Glu Lys Leu
            20                  25                  30

Asp Glu Leu Thr Ala Tyr Phe Ile Glu Gln Met Glu Lys Gly Leu Ala
        35                  40                  45

Pro Pro Lys Glu Gly His Thr Leu Ala Ser Asp Lys Gly Leu Pro Met
    50                  55                  60

Ile Pro Ala Phe Val Thr Gly Ser Pro Asn Gly Thr Glu Arg Gly Val
65                  70                  75                  80

Leu Leu Ala Ala Asp Leu Gly Gly Thr Asn Phe Arg Ile Cys Ser Val
                85                  90                  95

Asn Leu His Gly Asp His Thr Phe Ser Met Glu Gln Met Lys Ser Lys
            100                 105                 110

Ile Pro Asp Asp Leu Leu Asp Asp Glu Asn Val Thr Ser Asp Asp Leu
        115                 120                 125

Phe Gly Phe Leu Ala Arg Arg Thr Leu Ala Phe Met Lys Lys Tyr His
    130                 135                 140

Pro Asp Glu Leu Ala Lys Gly Lys Asp Ala Lys Pro Met Lys Leu Gly
145                 150                 155                 160

Phe Thr Phe Ser Tyr Pro Val Asp Gln Thr Ser Leu Asn Ser Gly Thr
                165                 170                 175

Leu Ile Arg Trp Thr Lys Gly Phe Arg Ile Ala Asp Thr Val Gly Lys
            180                 185                 190

Asp Val Val Gln Leu Tyr Gln Glu Gln Leu Ser Ala Gln Gly Met Pro
        195                 200                 205

Met Ile Lys Val Val Ala Leu Thr Asn Asp Thr Val Gly Thr Tyr Leu
    210                 215                 220

Ser His Cys Tyr Thr Ser Asp Asn Thr Asp Ser Met Thr Ser Gly Glu
225                 230                 235                 240

Ile Ser Glu Pro Val Ile Gly Cys Ile Phe Gly Thr Gly Thr Asn Gly
                245                 250                 255

Cys Tyr Met Glu Glu Ile Asn Lys Ile Thr Lys Leu Pro Gln Glu Leu
            260                 265                 270

Arg Asp Lys Leu Ile Lys Glu Gly Lys Thr His Met Ile Ile Asn Val
        275                 280                 285

Glu Trp Gly Ser Phe Asp Asn Glu Leu Lys His Leu Pro Thr Thr Lys
    290                 295                 300

Tyr Asp Val Val Ile Asp Gln Lys Leu Ser Thr Asn Pro Gly Phe His
305                 310                 315                 320

Leu Phe Glu Lys Arg Val Ser Gly Met Phe Leu Gly Glu Val Leu Arg
                325                 330                 335

Asn Ile Leu Val Asp Leu His Ser Gln Gly Leu Leu Leu Gln Gln Tyr
            340                 345                 350

Arg Ser Lys Glu Gln Leu Pro Arg His Leu Thr Thr Pro Phe Gln Leu
        355                 360                 365

Ser Ser Glu Val Leu Ser His Ile Glu Ile Asp Asp Ser Thr Gly Leu
    370                 375                 380
```

```
Arg Glu Thr Glu Leu Ser Leu Leu Gln Ser Leu Arg Leu Pro Thr Thr
385                 390                 395                 400

Pro Thr Glu Arg Val Gln Ile Gln Lys Leu Val Arg Ala Ile Ser Arg
                405                 410                 415

Arg Ser Ala Tyr Leu Ala Ala Val Pro Leu Ala Ala Ile Leu Ile Lys
            420                 425                 430

Thr Asn Ala Leu Asn Lys Arg Tyr His Gly Glu Val Glu Ile Gly Cys
        435                 440                 445

Asp Gly Ser Val Val Glu Tyr Tyr Pro Gly Phe Arg Ser Met Leu Arg
    450                 455                 460

His Ala Leu Ala Leu Ser Pro Leu Gly Ala Glu Gly Glu Arg Lys Val
465                 470                 475                 480

His Leu Lys Ile Ala Lys Asp Gly Ser Gly Val Gly Ala Ala Leu Cys
                485                 490                 495

Ala Leu Val Ala
            500

<210> SEQ ID NO 79
<211> LENGTH: 500
<212> TYPE: PRT
<213> ORGANISM: Artificial Sequence
<220> FEATURE:
<223> OTHER INFORMATION: Mutant GLK1 protein

<400> SEQUENCE: 79

Met Ser Phe Asp Asp Leu His Lys Ala Thr Glu Arg Ala Val Ile Gln
1               5                   10                  15

Ala Val Asp Gln Ile Cys Asp Asp Phe Glu Val Thr Pro Glu Lys Leu
                20                  25                  30

Asp Glu Leu Thr Ala Tyr Phe Ile Glu Gln Met Glu Lys Gly Leu Ala
            35                  40                  45

Pro Pro Lys Glu Gly His Thr Leu Ala Ser Asp Lys Gly Leu Pro Met
        50                  55                  60

Ile Pro Ala Phe Val Thr Gly Ser Pro Asn Gly Thr Glu Arg Gly Val
65                  70                  75                  80

Leu Leu Ala Ala Asp Leu Gly Gly Ala Asn Phe Arg Ile Cys Ser Val
                85                  90                  95

Asn Leu His Gly Asp His Thr Phe Ser Met Glu Gln Met Lys Ser Lys
                100                 105                 110

Ile Pro Asp Asp Leu Leu Asp Asp Glu Asn Val Thr Ser Asp Asp Leu
            115                 120                 125

Phe Gly Phe Leu Ala Arg Arg Thr Leu Ala Phe Met Lys Lys Tyr His
        130                 135                 140

Pro Asp Glu Leu Ala Lys Gly Lys Asp Ala Lys Pro Met Lys Leu Gly
145                 150                 155                 160

Phe Thr Phe Ser Tyr Pro Val Asp Gln Thr Ser Leu Asn Ser Gly Thr
                165                 170                 175

Leu Ile Arg Trp Thr Lys Gly Phe Arg Ile Ala Asp Thr Val Gly Lys
            180                 185                 190

Asp Val Val Gln Leu Tyr Gln Glu Gln Leu Ser Ala Gln Gly Met Pro
        195                 200                 205

Met Ile Lys Val Val Ala Leu Thr Asn Asp Thr Val Gly Thr Tyr Leu
    210                 215                 220

Ser His Cys Tyr Thr Ser Asp Asn Thr Asp Ser Met Thr Ser Gly Glu
225                 230                 235                 240
```

```
Ile Ser Glu Pro Val Ile Gly Cys Ile Phe Gly Thr Gly Thr Asn Gly
            245             250             255
Cys Tyr Met Glu Glu Ile Asn Lys Ile Thr Lys Leu Pro Gln Glu Leu
            260             265             270
Arg Asp Lys Leu Ile Lys Glu Gly Lys Thr His Met Ile Ile Asn Val
            275             280             285
Glu Trp Gly Ser Phe Asp Asn Glu Leu Lys His Leu Pro Thr Thr Lys
            290             295             300
Tyr Asp Val Val Ile Asp Gln Lys Leu Ser Thr Asn Pro Gly Phe His
305             310             315             320
Leu Phe Glu Lys Arg Val Ser Gly Met Phe Leu Gly Glu Val Leu Arg
            325             330             335
Asn Ile Leu Val Asp Leu His Ser Gln Gly Leu Leu Leu Gln Gln Tyr
            340             345             350
Arg Ser Lys Glu Gln Leu Pro Arg His Leu Thr Thr Pro Phe Gln Leu
            355             360             365
Ser Ser Glu Val Leu Ser His Ile Glu Ile Asp Ser Thr Gly Leu
            370             375             380
Arg Glu Thr Glu Leu Ser Leu Leu Gln Ser Leu Arg Leu Pro Thr Thr
385             390             395             400
Pro Thr Glu Arg Val Gln Ile Gln Lys Leu Val Arg Ala Ile Ser Arg
            405             410             415
Arg Ser Ala Tyr Leu Ala Ala Val Pro Leu Ala Ala Ile Leu Ile Lys
            420             425             430
Thr Asn Ala Leu Asn Lys Arg Tyr His Gly Glu Val Glu Ile Gly Cys
            435             440             445
Asp Gly Ser Val Val Glu Tyr Tyr Pro Gly Phe Arg Ser Met Leu Arg
450             455             460
His Ala Leu Ala Leu Ser Pro Leu Gly Ala Glu Gly Glu Arg Lys Val
465             470             475             480
His Leu Lys Ile Ala Lys Asp Gly Ser Gly Val Gly Ala Ala Leu Cys
            485             490             495
Ala Leu Val Ala
            500

<210> SEQ ID NO 80
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 80
gacgactacc caatcaagat tgttctgctg aagatggttc cagtgctggt gccgctgtta      60
```

US 10,837,022 B1

RECOMBINANT MICROORGANISMS WITH MIXED SUGAR UTILIZATION

PRIORITY

This application claims the benefit of U.S. Ser. No. 62/396,488, filed on Sep. 19, 2016, which is incorporated by reference herein in its entirety.

SEQUENCE LISTING

This document incorporates by reference herein an electronic sequence listing text file, which is filed in electronic format via EFS-Web. The text file is named "17-1186-US_SequenceListing_ST25.txt" is 53 KB, and was created on Sep. 18, 2017.

BACKGROUND

The threat of global climate change and environmental concerns from fossil fuel usage have motivated efforts into renewable microbial production of biofuels and chemicals (1). Among many potential microorganisms capable of industrial bioconversion, the brewer's yeast *Saccharomyces cerevisiae* has been widely used in these pursuits due to its established status as a model organism (2), multitude of available genetic tools (3-6), and capability for producing and tolerating high ethanol concentrations (7, 8).

Common feedstocks for renewable microbial bioconversion can be broadly divided into two categories: terrestrial (9) and marine (10). Terrestrial lignocellulosic biomass is primarily comprised of for example, glucose, xylose, and arabinose (11) whereas marine biomass, depending on the type, contains mixtures of either glucose and galactose or glucose, mannitol, and 4-deoxy-L-erythro-5-hexoseulose uronate (10, 12). Regardless of the variety, a common theme in all of these renewable carbon sources is the presence of mixed sugars. Thus, simultaneous consumption of mixed sugars is desirable for robust fermentations and enabling economic processes such as continuous fermentations (11, 13).

Attempts to enable efficient simultaneous sugar utilization have been ongoing for nearly two decades. Initial approaches for simultaneous glucose and xylose consumption involved co-cultures of *S. cerevisiae* with xylose-fermenting yeasts such as *Pichia stipitis* and *Candida shehatae* (14-17). The next notable development was the construction of a strain that hydrolyzed glucose oligomers intracellularly (18) and was able to simultaneously consume mixtures of cellobiose and xylose (19, 20). Meanwhile, xylose transport in the presence of glucose was predicted to be greatly reduced during fermentations of glucose and xylose mixtures (21) and later experimentally verified as an overall limiting factor in xylose utilization from mixed sugars (22). This determination of the molecular mechanism underlying glucose repression of xylose utilization has motivated significant recent work into engineered transporters with increased xylose specificity (23-28). While efficient consumption of xylose in the presence of glucose is now feasible, glucose is nonetheless consumed more rapidly.

Glucose repression on galactose metabolic genes occurs in response to a certain extracellular ratio of the two sugars (29). Modifying the glucose repression pathway through deletion of HXK2 (30) or double deletion of the transcription factors GAL80 and MIG1 (31) allows simultaneous consumption of the two sugars, however, in both these cases consumption of glucose outpaces galactose.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The features, objects and advantages other than those set forth above will become more readily apparent when consideration is given to the detailed description below. Such detailed description makes reference to the following drawings, wherein:

(FIG. 10A) Scheme for control over HXK2 expression using the external inducer doxycycline. The synthetic transactivator rtTA-S2 activates expression of hxk2 when bound to doxycycline. (FIG. 10B-H) Pure glucose fermentations of SR8Δhxk$^0$ with tunable HXK2 expression. SR8Δhxk$^0$ with inducible HXK2 (FIG. 10B-H) was cultured with various levels of doxycycline at (FIG. 10B) 0, (FIG. 10C) 2, (FIG. 10D) 4, (FIG. 10E) 6, (FIG. 10F) 8, (FIG. 10G) 10, and (FIG. 10H) 12 μg/mL. Fermentations were performed with 25 mL YP media in 125 mL flasks at an initial OD of 1. Data points are the result of duplicate experiments with standard deviations indicated by error bars. Data points are: OD (yellow circle), glucose (blue square), and ethanol (black downward triangle).

(FIG. 11A) Scheme for control over HXK2 expression using the external inducer doxycycline. The synthetic transactivator rtTA-S2 activates expression of hxk2 when bound to doxycycline. (FIG. 11B-H) SR8 with tunable HXK2 cultured in a mixture of glucose and xylose. SR8Δhxk$^0$ with inducible HXK2 (FIG. 11B-H) was cultured with various levels of doxycycline at (FIG. 11B) 0, (FIG. 11C) 2, (FIG. 11D) 4, (FIG. 11E) 6, (FIG. 11F) 8, (FIG. 11G) 10, and (FIG. 11H) 12 μg/mL. Fermentations were performed with 25 mL YP media in 125 mL flasks at an initial OD of 1. Data points are the result of duplicate experiments with standard deviations indicated by error bars. Data points are: OD (yellow circle), glucose (blue square), xylose (red triangle), and ethanol (black downward triangle).

(FIG. 12A-H) Measurements of sugar consumption rates across different sugar ratios when hexokinases are induced with 4 μg/mL doxycycline. Glucose and xylose consumption rates are indicated by blue squares and red triangles, respectively. (FIG. 12A) Pure xylose and (FIG. 12E) pure glucose conditions are pictured along with (FIG. 12B-D) constant glucose concentrations with varied xylose and (FIG. 12F-H) constant xylose concentration with varied glucose.

SUMMARY

Figure 1:
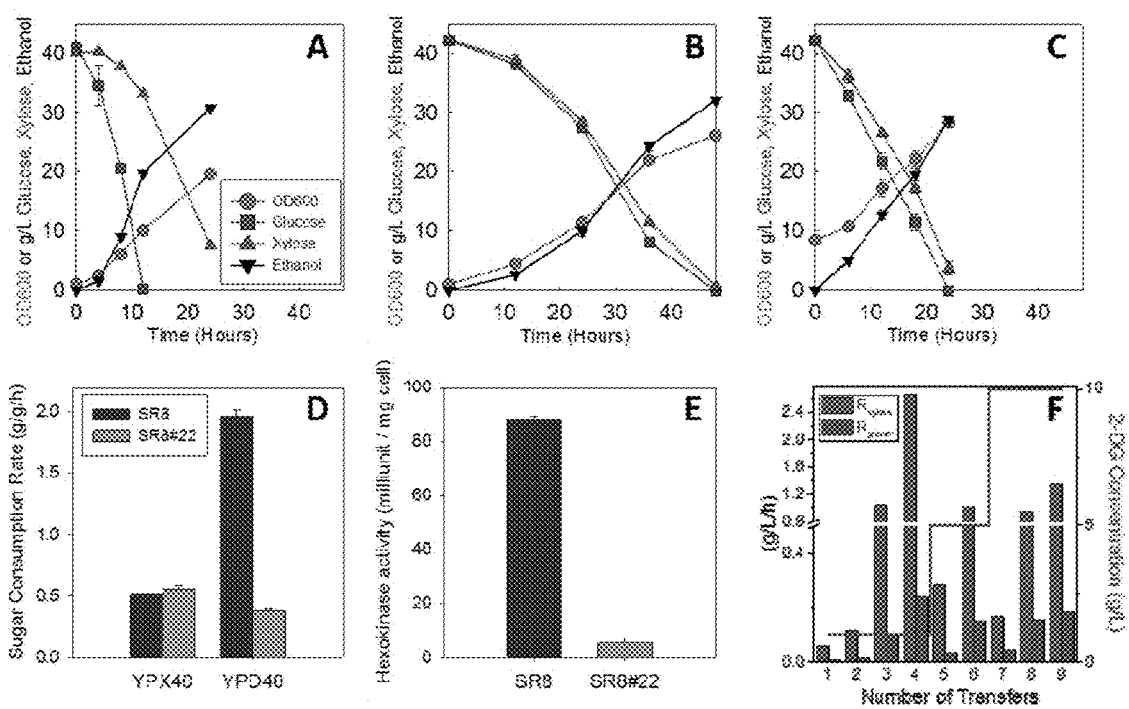
FIG. 1 panels A-F. Evolution on xylose with the glucose analogue 2-deoxyglucose leads to isolation of a simultaneous co-fermenting mutant. Fermentation profile of (A) SR8 and (B) SR8#22 with initial OD 1 and (C) SR8#22 with initial OD 10 in complex medium containing 40 g/L xylose and 40 g/L glucose under oxygen-limited conditions. (D) Specific sugar consumption rate of SR8 and SR8#22 when cultured in YP medium with pure glucose or xylose as a sole carbon source. The fermentation results are the means of duplicate experiments; the error bars indicate standard deviations. (E) Hexokinase activity assay of SR8 and SR8#22. (F) Evolution leading to the isolation of SR8#22 from the original parent SR8. The strain was evolved in YP medium with xylose as a carbon source while the 2-deoxyglucose concentration was increased periodically.

An embodiment provides a genetically engineered yeast having attenuated expression of a polynucleotide encoding a Hxk1 polypeptide, a Hxk2 polypeptide, a Glk1 polypeptide, or combination thereof. The Hxk1 polypeptide can have at least 90% identity to SEQ ID NO:74, the Hxk2 polypeptide can have at least 90% identity to SEQ ID NO:76, and the Glk1 polypeptide can have at least 90% identity to SEQ ID NO:78. The attenuated expression can be caused by at least one gene disruption of a Hxk1 gene, a Hxk2 gene, a Glk1 gene, or combinations thereof which results in attenuated expression of the Hxk1 gene, the Hxk2 gene, the Glk1 gene or combinations thereof.

Another embodiment provides a genetically engineered yeast having an ability to co-utilize sugars, wherein the biological activity of an endogenous protein having at least 90% sequence identity to an amino acid sequence set forth in SEQ ID NO:74, SEQ ID NO:76, SEQ ID NO: 78, or combinations thereof is reduced or eliminated as compared to a control yeast.

A yeast can express a Hxk1 polypeptide, a Hxk2 polypeptide, a Glk1 polypeptide or combinations thereof at a level of about 10%, 20%, 30%, 40%, 50%, 60%, 70%, 80%, 90% or 95% less than a control yeast. The yeast can have improved sugar co-utilization of two or more sugars as compared to a control yeast. The two or more sugars can be selected from, for example, glucose, galactose, lactose, arabinose, mannose, sucrose, fructose, xylobiose, cellobiose, xylose, rhamnose, 4-deoxy-L-erythro-5-hexoseulose urinate, maltose, and cellodextrins.

The yeast can be selected from *Saccharomyces cerevisiae, Saccharomyces cerevisiae* S8 strain, *Saccharomyces fermentati, Saccharomyces paradoxus, Saccharomyces uvarum* and *Saccharomyces bay anus, Schizosaccharomyces pombe, Schizosaccharomyces japonicus, Schizosaccharomyces octosporus, Schizosaccharomyces cryophilus, Torulaspora delbrueckii, Kluyveromyces marxianus, Pichia stipitis, Pichia pastoris, Pichia angusta, Zygosaccharomyces bailii, Brettanomyces inter medius, Brettanomyces bruxellensis, Brettanomyces anomalus, Brettanomyces custersianus, Brettanomyces naardenensis, Brettanomyces nanus, Dekkera bruxellensis, Dekkera anomala, Issatchenkia orientalis, Kloeckera apiculata*; and *Aureobasidium pullulans*.

The yeast can additionally comprise a recombinant polynucleotide encoding a XYL1 polypeptide, a XYL2 polypeptide, a XYL3 polypeptide, or a combination thereof. The yeast can further have attenuated expression of a polynucleotide encoding a Ald6 polypeptide, attenuated expression of a polynucleotide encoding a Ura3 polypeptide, or combinations thereof.

The polynucleotides encoding a Hxk1 polypeptide, a Hxk2 polypeptide, or a Glk1 polypeptide can be deleted or mutated using a genetic manipulation technique selected from TALEN, Zinc Finger Nucleases, and CRSPR-Cas9.

In an embodiment, one or more regulatory elements controlling expression of the polynucleotides encoding a Hxk1 polypeptide, a Hxk2 polypeptide, a Glk1 polypeptide, or combinations thereof can be mutated to prevent or attenuate expression of the Hxk1 polypeptide, the Hxk2 polypeptide, the Glk1 polypeptide, or combinations thereof as compared to a control yeast. The regulatory elements controlling expression of the polynucleotides encoding Hxk1, Hxk2, and Glk1 polypeptides can be replaced with recombinant regulatory elements that prevent or attenuate the expression of the Hxk1 polypeptide, the Hxk2 polypeptide, the Glk1 polypeptide, or combinations thereof as compared to wild-type yeast or a control yeast.

In another embodiment, the genetically engineered yeast can comprise a Hxk1 polypeptide having a T89A mutation, a Hxk2 polypeptide having a P455F mutation, a Glk1 polypeptide having a S306P mutation, or combinations thereof.

Even another embodiment provides a genetically engineered yeast comprising a polynucleotide encoding at least one mutant polypeptide selected from Hxk1 T89A, Hxk2 P455F, and Glk1 S306P.

A genetically engineered yeast can have a reduced glucose consumption rate as compared to a control yeast. A genetically engineered yeast can have a glucose consumption rate that is about 25% of a control yeast.

Yet another embodiment provides a method of making a genetically engineered yeast having improved co-utilization of glucose and a second sugar. The method can comprise deleting or mutating a polynucleotide encoding at least one polypeptide selected from a Hxk1 polypeptide, a Hxk2 polypeptide, and a Glk1 polypeptide, such that the Hxk1 polypeptide, the Hxk2 polypeptide, the Glk1 polypeptide or combinations thereof are expressed an attenuated rate as compared to a control yeast. The second sugar can be galactose, xylose, lactose, sucrose, arabinose, maltose, or cellodextrins.

Another embodiment provides a method for co-utilization of two or more sugars in a fermentation reaction comprising contacting a genetically modified yeast described herein with the two or more sugars under fermentation conditions such that the two of more sugars are co-utilized at an improved rate as compared to a control yeast. The two or more sugars can be, for example, glucose, galactose, lactose, arabinose, mannose, sucrose, fructose, xylobiose, cellobiose, xylose, rhamnose, 4-deoxy-L-erythro-5-hexoseulose urinate, maltose, and cellodextrins. The first sugar can be glucose and the second sugar can be, for example, galactose, lactose, arabinose, mannose, sucrose, fructose, xylobiose, cellobiose, xylose, rhamnose, 4-deoxy-L-erythro-5-hexoseulose urinate, maltose, and cellodextrins. The consumption of glucose can be reduced as compared to a control yeast and the consumption of a second sugar can be increased such that the two of more sugars are co-utilized at an improved rate as compared to a control yeast Even another embodiment provides a method of fermenting mixtures of sugars comprising contacting a genetically modified yeast described herein with the mixture of sugars under fermentation conditions such that the mixture of sugars are co-fermented at an improved rate as compared to a control yeast.

Still another embodiment provides a method of producing ethanol comprising contacting a genetically modified yeast described herein with two or more sugars under fermentation conditions such that the two of more sugars are co-utilized and ethanol is produced.

DETAILED DESCRIPTION

The compositions and methods are more particularly described below and the Examples set forth herein are intended as illustrative only, as numerous modifications and variations therein will be apparent to those skilled in the art. As used in the description herein and throughout the claims that follow, the meaning of "a", "an", and "the" includes plural reference unless the context clearly dictates otherwise. The term "about" in association with a numerical value means that the value varies up or down by 5%. For example, for a value of about 100, means 95 to 105 (or any value between 95 and 105).

The terms used in the specification generally have their ordinary meanings in the art, within the context of the compositions and methods described herein, and in the specific context where each term is used. Some terms have been more specifically defined below to provide additional guidance to the practitioner regarding the description of the compositions and methods.

Overview

The present disclosure provides a metabolic design enabling simultaneous mixed sugar utilization (i.e., co-utilization; co-fermentation) in microorganism (e.g. *Saccharomyces cerevisiae*.) Through adaptive evolution under a mixture of the glucose analog 2-deoxyglucose and xylose, a mutant strain capable of simultaneously consuming glucose and xylose was isolated. Genome sequencing of the evolved mutant followed by Cas9-based reverse engineering revealed that mutations in the glucose phosphorylating enzymes (Hxk1 T89A, Hxk2 P455F, Glk1 S306P) were sufficient to confer simultaneous glucose and xylose utilization. To understand the role of hexokinase activity on mixed sugar utilization, we varied hexokinase expression with an inducible promoter. Slowing glucose consumption through altered hexokinase expression led to simultaneous utilization of glucose and xylose. Interestingly, no mutations in sugar transporters occurred during the evolution and no specific transporter played an indispensable role in simultaneous sugar utilization. Additionally, slowing glucose consumption also enables simultaneous utilization of glucose and galactose. These results suggest that the combined effects of metabolic flux and transport inhibition constitute the outermost layer of glucose repression. Ultimately, we present a general design principle for transgenic microorganisms, enabling simultaneous sugar utilization across a range of metabolic pathways.

Genetically Engineered Microorganisms

Genetically engineered microorganisms of the disclosure comprise one or more gene disruptions of one or more polynucleotides encoding Hxk1, Hxk2, Glk1, Ald6, Ura3, or any combination thereof. In an embodiment the polynucleotides encoding Hxk1, Hxk2, Glk1, Ald6, Ura3, can be endogenous and one or more gene disruptions can be genetically engineered into the Hxk1, Hxk2, Glk1, Ald6, and Ura3, polynucleotides. In another embodiment polynucleotides encoding Hxk1, Hxk2, Glk1, Ald6, or Ura3, polypeptides and having one or more gene disruptions can be genetically engineered into microorganisms that do not endogenously produce Hxk1, Hxk2, Glk1, Ald6 or Ura3. In an embodiment a genetically engineered microorganism comprises one or more gene disruptions of polynucleotides encoding Hxk1, Hxk2, Glk1, Ald6 and Ura3.

A heterologous or exogenous polypeptide or polynucleotide refers to any polynucleotide or polypeptide that does not naturally occur or that is not present in the starting target microorganism. For example, a polynucleotide from a bacteria that is transformed into a yeast cell that does naturally or otherwise comprise the bacterial polynucleotide, is a heterologous or exogenous polynucleotide. A heterologous or exogenous polypeptide or polynucleotide can be a wild-type, synthetic, or mutated polypeptide or polynucleotide. In an embodiment, a heterologous or exogenous polypeptide or polynucleotide is not naturally present in a starting target microorganism and is from a different genus or species than the starting target microorganism.

A homologous or endogenous polypeptide or polynucleotide refers to any polynucleotide or polypeptide that naturally occurs or that is otherwise present in a starting target microorganism. For example, a polynucleotide that is naturally present in a yeast cell is a homologous or endogenous polynucleotide. In an embodiment, a homologous or endogenous polypeptide or polynucleotide is naturally present in a starting target microorganism.

Sugar Utilization

Improved sugar utilization, increased sugar utilization, improved sugar utilization rate, and increased sugar utilization rate refers to increasing the amount of one or more sugars (e.g., glucose, xylose, galactose, and other sugars) fermented or consumed over a specific period of time and/or increasing the rate at which one or more sugars are consumed in a specified amount of time. In some embodiments, a microorganism that has been modified as described herein has improved sugar utilization if the amount of sugar fermented or consumed by the microorganism over a specified period of time (e.g., over about 1, 2, 5, 10, 15, 20, 24, 25, 30, 36, 48, or more or hours is at least about 10%, 15%, 20%, 25%, 30%, 40%, 50%, 60%, 70%, or 80% more than the amount of sugar consumed over the same specified period of time for a wild-type or control microorganism (e.g., an otherwise identical strain that has not been recombinantly modified as described herein). In some embodiments, a genetically engineered microorganism that has been modified as described herein has improved sugar utilization if the amount of sugar (e.g., glucose, xylose, galactose, or other sugars) consumed or fermented by the microorganism over a specified period of time (e.g., over about 1, 2, 5, 10, 15, 20, 24, 25, 30, 36, 48 or more hours) is at least about 10%, 15%, 20%, 25%, 30%, 40%, 50%, 60%, 70, or 80% more than the amount of sugar fermented or consumed over the same specified period of time for a control or wild-type microorganism (e.g., an otherwise identical yeast strain that has not been recombinantly modified as described herein).

In some embodiments, a microorganism that has been recombinantly modified as described herein has improved sugar utilization if the rate at which the cell consumes a specified amount of sugar (e.g., glucose, xylose, galactose, or other sugars) is at least about 10%, 15%, 20%, 25%, 30%, 40%, 50%, 60%, 70%, or 80% greater than the rate for a control or wild-type microorganism under the same culture conditions. In some embodiments, a microorganism that has been modified as described herein has improved sugar utilization if the rate at which the microorganism consumes a specified amount of sugar (e.g., glucose, xylose, galactose or other sugars) is at least about 10%, 15%, 20%, 25%, 30%, 40%, 50%, 60%, 70%, 80%, or 90% greater than the rate for a control or wild-type microorganism under the same culture conditions.

Decreased Glucose Consumption

In an embodiment decreased glucose utilization, decreased glucose consumption, decreased glucose utilization rate, and decreased glucose consumption rate refers to decreasing the amount of glucose fermented or consumed over a specific period of time and/or decreasing the rate at which glucose is consumed in a specified amount of time. This reduction in glucose fermentation or consumption can be advantageous in that it allows for improved sugar co-utilization. In some embodiments, a microorganism that has been modified as described herein has decreased glucose utilization or consumption if the amount of glucose fermented or consumed by the microorganism over a specified period of time (e.g., over about 1, 2, 5, 10, 15, 20, 24, 25, 30, 36, 48, or more or hours) is at least about 10%, 15%, 20%, 25%, 30%, 40%, 50%, 60%, 70%, 80%, or 90% less than the amount of glucose consumed over the same specified period of time for a wild-type or control microorganism (e.g., an otherwise identical yeast strain that has not been recombinantly modified as described herein). In some embodiments, a genetically engineered microorganism that has been modified as described herein has decreased glucose utilization if the amount of glucose consumed or fermented by the microorganism over a specified period of time (e.g., over about 1, 2, 5, 10, 15, 20, 24, 25, 30, 36, 48 or more hours) is at least about 10%, 15%, 20%, 25%, 30%, 40%, 50%, 60%, 70%, 80%, or 90% less than the amount of glucose fermented or consumed over the same specified period of time for a control or wild-type microorganism (e.g., an otherwise identical strain that has not been recombinantly modified as described herein).

In some embodiments, a microorganism that has been recombinantly modified as described herein has decreased glucose utilization if the rate at which the cell consumes a specified amount of glucose is at least about 10%, 15%, 20%, 25%, 30%, 40%, 50%, 60%, 70%, 80% or 90% less than the rate for a control or wild-type microorganism under the same culture conditions. In some embodiments, a microorganism that has been modified as described herein has decreased glucose utilization if the rate at which the microorganism consumes a specified amount of glucose is at least about 10%, 15%, 20%, 25%, 30%, 40%, 50%, 60%, 70%, 80%, or 90% less than the rate for a control or wild-type microorganism under the same culture conditions.

Improved Sugar Co-Utilization

A microorganism that co-utilizes, co-ferments, or co-consumes (or exhibits co-utilization, co-fermentation, or co-consumption) of two or more sugars (e.g., xylose, glucose, galactose) is a microorganism that when grown in medium containing two or more sugars (in equal ratios or in different ratios) consumes (ferments) the sugars simultaneously rather than, in contrast, consuming (fermenting) the sugars sequentially (e.g., consuming (fermenting) glucose before consuming (fermenting) the xylose or other sugar).

Improved co-utilization or increased co-utilization, means co-utilization of two or more sugars (e.g., glucose, xylose, galactose, or other sugars), by increasing the consumption of one or more sugars (e.g., 1, 2, 3, 4, or more sugars) by a microorganism at the same time over a specific period of time (e.g., about 1, 2, 5, 10, 15, 20, 24, 25, 30, 36, 48 or more hours) and/or increasing the rate at which a specified amount of one or more sugars are consumed by the microorganism over a specified period of time (e.g., about 1, 2, 5, 10, 15, 20, 24, 25, 30, 36, 48 or more hours). In some embodiments, a microorganism that has been modified as described herein has improved sugar co-utilization if the amount of total sugars (e.g., glucose, xylose, galactose, etc.) consumed by a microorganism over a specified period of time (e.g., about 1, 2, 5, 10, 15, 20, 24, 25, 30, 36, 40, 48, or more hours) is at least about 10%, 15%, 20%, 25%, 30%, 40%, 50%, 60%, 70%, 80%, or 90% greater than the amount of total sugars (e.g., glucose, xylose, galactose, etc.) consumed over the same specific period of time for a control or wild-type cell (e.g., an otherwise identical strain in that has not been recombinantly modified as described herein). In some embodiments, a host cell that has been modified as described herein has improved sugar co-utilization if the amount of total sugars (e.g., glucose, xylose, galactose, etc.) consumed by the cell over a specified period of time (e.g., about 1, 2, 5, 10, 15, 20, 24, 25, 30, 36, 40, or 48 hours) is at least 10%, 15%, 20%, 25%, 30%, 40%, 50%, 60%, 70%, 80%, or 90% more than the amount of total sugars (e.g., glucose, xylose, galactose) consumed over the same specific period of time for a control or wild-type microorganism (e.g., an otherwise identical strain in that has not been recombinantly modified as described herein).

In some embodiments, a microorganism that has been modified as described herein has improved sugar co-utilization if the rate at which a specified amount of total sugars (e.g., glucose, xylose, galactose, etc.) is consumed by the microorganism in a specified amount of time (e.g., about 1, 2, 5, 10, 15, 20, 24, 25, 30, 36, 40, 48 or more hours) is at least about 10%, 15%, 20%, 25%, 30%, 40%, 50%, 60%, 70%, 80%, or 90% faster than the rate at which the same specified amount of total sugars is consumed in the same specified amount of time by a control or wild-type microorganism (e.g., an unmodified host cell of the same type). In some embodiments, a host cell that has been modified as described herein has improved sugar co-utilization if the rate at which a specified amount of total sugars (e.g., glucose plus xylose) is consumed by the host cell in a specified amount of time (e.g., about 1, 2, 5, 10, 15, 20, 24, 25, 30, 35, 40, or 48 hours) is at least about 10%, 15%, 20%, 25%, 30%, 40%, 50%, 60%, 70%, 80%, or 90% faster than the rate at which the same specified amount of total sugars is consumed in the same specified amount of time by a control or wild-type microorganism (e.g., an unmodified microorganism of the same type).

In some embodiments, improved sugar co-utilization can occur when the rate of glucose consumption is reduced as compared to a control microorganism, but the rate of consumption of one or more other sugars is increased as compared to a control microorganism. This is considered improved sugar co-utilization, because, inter alia, the sugars are fermented simultaneously rather than sequentially. While the rate of glucose consumption can be reduced, the amount of total sugars consumed or fermented over a specific time period is increased resulting in improved sugar co-utilization.

When co-utilizing sugars, a microorganism can consume at least about 1%, 2.5%, 5%, 7.5%, or 10% of the initial amount of a first sugar (e.g., xylose) in the medium during the time the microorganism consumes about 10% of the initial amount of a second sugar (e.g., glucose) in the medium; at least about 5%, 10%, 15%, or 20% of the initial amount of a first sugar (e.g., xylose) in the medium during the time the microorganism consumes about 20% of the initial amount of a second sugar (e.g. glucose) in the medium; at least about 10%, 15%, 20%, 25%, or 30% of the initial amount of a first sugar (e.g. xylose) in the medium during the time the microorganism consumes about 30% of the initial amount of a second sugar (e.g. glucose) in the medium; at least about 10%, 20%, 25%, 30%, 35%, or 40% of the initial amount of a first sugar (e.g. xylose) in the medium during the time the microorganism consumes about 40% of the initial amount of a second sugar (e.g. glucose) in the medium; at least about 10%, 20%, 30%, 35%, 40%, 45%, or 50% of the initial amount of a first sugar (e.g. xylose) in the medium during the time the microorganism consumes about 50% of the initial amount of a second sugar (e.g. glucose) in the medium; at least about 20%, 40%, 45%, 50%, 55%, or 60% of the initial amount of a first sugar (e.g. xylose) in the medium during the time the microorganism consumes about 60% of the initial amount of a second sugar (e.g. glucose) in the medium; at least about 40%, 50%, 55%, 60%, 65%, or 70% of the initial amount of a first sugar (e.g. xylose) in the medium during the time the microorganism consumes about 70% of the initial amount of a second sugar (e.g. glucose) in the medium; at least about 50%, 60%, 65%, 70%, 75%, or 80% of the initial amount of a first sugar (e.g. xylose) in the medium during the time the microorganism consumes about 80% of the initial amount of a second sugar (e.g. glucose) in the medium; or at least about 50%, 60%, 70%, 75%, 80%, 85%, or 90% of the initial amount of a first sugar (e.g. xylose) in the medium during the time the microorganism consumes about 90% of the initial amount of a second sugar (e.g. glucose) in the medium.

When co-utilizing sugars, a microorganism can consume at least about 1%, 2.5%, 5%, 7.5%, or 10% of the initial amount of a first sugar and a second sugar (e.g., xylose and galactose) in the medium during the time the microorganism consumes about 10% of the initial amount of a third sugar (e.g., glucose) in the medium; at least about 5%, 10%, 15%, or 20% of the initial amount of a first sugar and a second sugar (e.g., xylose and galactose) in the medium during the time the microorganism consumes about 20% of the initial amount of a third sugar (e.g. glucose) in the medium; at least about 10%, 15%, 20%, 25%, or 30% of the initial amount of a first sugar and a second sugar (e.g., xylose and galactose) in the medium during the time the microorganism consumes about 30% of the initial amount of a third sugar (e.g. glucose) in the medium; at least about 10%, 20%, 25%, 30%, 35%, or 40% of the initial amount of a first sugar and a second sugar (e.g., xylose and galactose) in the medium during the time the microorganism consumes about 40% of the initial amount of a third sugar (e.g. glucose) in the medium; at least about 10%, 20%, 30%, 35%, 40%, 45%, or 50% of the initial amount of a first sugar and a second sugar (e.g., xylose and galactose) in the medium during the time the microorganism consumes about 50% of the initial amount of a third sugar (e.g. glucose) in the medium; at least about 20%, 40%, 45%, 50%, 55%, or 60% of the initial amount of a first sugar and a second sugar (e.g., xylose and galactose) in the medium during the time the microorganism consumes about 60% of the initial amount of a third sugar (e.g. glucose) in the medium; at least about 40%, 50%, 55%, 60%, 65%, or 70% of the initial amount of a first sugar and a second sugar (e.g., xylose and galactose) in the medium during the time the microorganism consumes about 70% of the initial amount of a third sugar (e.g. glucose) in the medium; at least about 50%, 60%, 65%, 70%, 75%, or 80% of the initial amount of a first sugar and a second sugar (e.g., xylose and galactose) in the medium during the time the microorganism consumes about 80% of the initial amount of a third sugar (e.g. glucose) in the medium; or at least about 50%, 60%, 70%, 75%, 80%, 85%, or 90% of the initial amount of a first sugar and a second sugar (e.g., xylose and galactose) in the medium during the time the microorganism consumes about 90% of the initial amount of a third sugar (e.g. glucose) in the medium.

In an embodiment, sugars are co-utilized when about 10%, 15%, 20%, 25%, 30%, 40%, 50%, 60%, 70%, 80%, or 90% of both a first and second sugar are consumed in about 1, 2, 5, 10, 15, 20, 24, 25, 30, 35, 40, or 48 hours. In an embodiment, sugars are co-utilized when about 30%, 40%, or 50% of both a first and second sugar are consumed in about 15, 20, 24, 25, 30, 35, 40, or 48 hours. In an embodiment, sugars are co-utilized when about 50%, 60%, or 70% of both a first and second sugar are consumed in about 20, 24, 25, 30, 35, 40, or 48 hours. In an embodiment, sugars are co-utilized when about 60%, 70%, or 80% of both a first and second sugar are consumed in about 24, 25, 30, 35, 40, or 48 hours.

Recombinant Microorganisms

A recombinant, transgenic, or genetically engineered microorganism is a microorganism, e.g., bacteria, fungus, or yeast that has been genetically modified from its native state. Thus, a "recombinant yeast" or "recombinant yeast cell" refers to a yeast cell (i.e., Ascomycota and Basidiomycota) that has been genetically modified from the native state. A recombinant yeast cell can have, for example, nucleotide insertions, nucleotide deletions, nucleotide rearrangements, gene disruptions, recombinant polynucleotides, heterologous polynucleotides, deleted polynucleotides, nucleotide modifications, or combinations thereof introduced into its DNA. These genetic modifications can be present in the chromosome of the yeast or yeast cell, or on a plasmid in the yeast or yeast cell. Recombinant cells disclosed herein can comprise exogenous nucleotide sequences on plasmids. Alternatively, recombinant cells can comprise exogenous nucleotide sequences stably incorporated into their chromosome.

A recombinant microorganism can comprise one or more polynucleotides not present in a corresponding wild-type cell, wherein the polynucleotides have been introduced into that microorganism using recombinant DNA techniques, or which polynucleotides are not present in a wild-type microorganism and is the result of one or more mutations.

A genetically modified or recombinant microorganism can be yeast (i.e., (i.e., Ascomycota and Basidiomycota). Examples include: Saccharomyceraceae, such as *Saccharomyces cerevisiae*, *Saccharomyces cerevisiae* strain S8, *Saccharomyces pastorianus*, *Saccharomyces beticus*, *Saccharomyces fermentati*, *Saccharomyces paradoxus*, *Saccharomyces uvarum* and *Saccharomyces bayanus*; Schizosaccharomyces such as *Schizosaccharomyces pombe*, *Schizosaccharomyces japonicus*, *Schizosaccharomyces octosporus* and *Schizosaccharomyces cryophilus*; Torulaspora such as *Torulaspora delbrueckii*; Kluyveromyces such as *Kluyveromyces marxianus*; Pichia such as *Pichia stipitis*, *Pichia pastoris* or *pichia angusta*, Zygosaccharomyces such as *Zygosaccharomyces bailii*; Brettanomyces such as *Brettanomyces inter medius*, *Brettanomyces bruxellensis*, *Brettanomyces anomalus*, *Brettanomyces custersianus*, *Brettanomyces naardenensis*, *Brettanomyces nanus*, *Dekkera bruxellensis* and *Dekkera anomala*; Metschmkowia, Issatchenkia, such as *Issatchenkia orientalis*, Kloeckera such as *Kloeckera apiculata*; Aureobasidium such as *Aureobasidium pullulans*.

In an embodiment, a genetically engineered or recombinant microorganism has attenuated expression of a polynucleotide encoding a Hxk1 polypeptide, a Hxk2 polypeptide, a Glk1 polypeptide, a Ald6 polypeptide, a Ura3 polypeptide, or combinations thereof. Attenuated means reduced in amount, degree, intensity, or strength. Attenuated gene or polynucleotide expression can refer to a reduced amount and/or rate of transcription of the gene or polynucleotide in question. As nonlimiting examples, an attenuated gene or polynucleotide can be a mutated or disrupted gene or polynucleotide (e.g., a gene or polynucleotide disrupted by partial or total deletion, truncation, frameshifting, or insertional mutation) or that has decreased expression due to alteration or disruption of gene regulatory elements. An attenuated gene may also be a gene targeted by a construct that reduces expression of the gene or polynucleotide, such as, for example, an antisense RNA, microRNA, RNAi molecule, or ribozyme.

Attenuate also means to weaken, reduce, or diminish the biological activity of a gene product or the amount of a gene product expressed (e.g., Hxk1, Hxk2, Glk1, Ald6, Ura3 proteins) via, for example a decrease in translation, folding, or assembly of the protein. In an embodiment attenuation of a gene product (a Hxk1, Hxk2, Glk1, Ald6, or Ura3 protein) means that the gene product is expressed at a rate or amount about 5, 10, 20, 30, 40, 50, 60, 70, 80, 90, 95, or 99% less (or any range between about 5 and 99% less; about 5 and 95% less; about 20 and 50% less, about 10 and 40% less, or about 10 and 90% less) than occurs in a wild-type or control organism. In an embodiment, attenuation of a gene product (e.g., Hxk1, Hxk2, Glk1, Ald6 or Ura3) means that the biological activity of the gene product is about 5, 10, 20, 30, 40, 50, 60, 70, 80, 90, 95, or 99% less (or any range between about 5 and 99% less; about 5 and 95% less, about 10 and 90% less) than occurs in a wild-type or control organism. Hxk1 is hexokinase isoenzyme 1 and its biological activity that it catalyzes phosphorylation of glucose during glucose metabolism, Hxk2 is hexokinase isoenzyme 1 and it phosphorylates glucose in the cytosol. Glk1 is glucokinase and it catalyzes the phosphorylation of glucose at C6 in the first step of glucose metabolism. Ald6 is an aldehyde dehydrogenase and is required for conversion of acetaldehyde to acetate. Ura3 is orotidine-5'-phosphate (OMP) decarboxylase and it catalyzes the sixth enzymatic step in the de novo biosynthesis of pyrimidines. Ura 3 can convert OMP into uridine monophosphate (UMP) and can convert 5-FOA into 5-fluorouracil.

In an embodiment a genetically engineered or recombinant microorganism expresses a polynucleotide encoding a Hxk1 polypeptide, a Hxk2 polypeptide, a Glk1 polypeptide, a Ald6 polypeptide, a Ura3 polypeptide, or combinations thereof at an attenuated rate or amount (e.g., amount and/or rate of transcription of the gene or polynucleotide). An attenuated rate or amount is about 5, 10, 20, 30, 40, 50, 60, 70, 80, 90, 95, 99% less than the rate of a wild-type or control microorganism. The result of attenuated expression of polynucleotide encoding a Hxk1 polypeptide, a Hxk2 polypeptide, a Glk1 polypeptide, a Ald6 polypeptide, a Ura3 polypeptide or combinations thereof is attenuated expression of a Hxk1 polypeptide, a Hxk2 polypeptide, a Glk1 polypeptide, a Ald6 polypeptide, or a Ura3 polypeptide.

Attenuated expression requires at least some expression of a biologically active wild-type or mutated Hxk1 polypeptide, wild-type or mutated Hxk2 polypeptide, wild-type or mutated Glk1 polypeptide, wild-type or mutated Ald6 polypeptide, wild-type or mutated Ura3 polypeptide or combinations thereof.

Deleted or null gene or polynucleotide expression can be gene or polynucleotide expression that is eliminated, for example, reduced to an amount that is insignificant or undetectable. Deleted or null gene or polynucleotide expression can also be gene or polynucleotide expression that results in an RNA or protein that is nonfunctional, for example, deleted gene or polynucleotide expression can be gene or polynucleotide expression that results in a truncated RNA and/or polypeptide that has substantially no biological activity.

In an embodiment, a genetically engineered or recombinant microorganism has no expression of a polynucleotide encoding a Hxk1 polypeptide, a Hxk2 polypeptide, a Glk1 polypeptide, a Ald6 polypeptide, a Ura3 polypeptide, or combination thereof. The result is that substantially no Hxk1 polypeptides, Hxk2 polypeptides, Glk1 polypeptides, Ald6 polypeptides, Ura3 polypeptides or combinations are present in the cell.

The lack of expression can be caused by at least one gene disruption or mutation of a Hxk1 gene, a Hxk2 gene, a Glk1 gene, a Ald6 gene, a Ura3 gene, or combinations thereof which results in no expression of the Hxk1 gene, the Hxk2 gene, the Glk1 gene, the Ald6 gene, the Ura3 gene, or combinations thereof. For example, the lack of expression can be caused by a gene disruption in a Hxk1 gene, a Hxk2 gene, a Glk1 gene, a Ald6 gene, or a Ura3 gene which results in attenuated expression of the Hxk1 gene, the Hxk2 gene, the Glk1 gene, the Ald6 gene, or the Ura3 gene. Alternatively, a Hxk1 gene, a Hxk2 gene, a Glk1 gene, a Ald6 gene, a Ura3 gene, or combinations thereof can be transcribed but not translated, or the genes can be transcribed and translated, but the resulting Hxk1 polypeptide, Hxk2 polypeptide, Glk1 polypeptide, Ald6 polypeptide, Ura3 polypeptide, or combinations thereof have substantially no biological activity.

In an embodiment, a recombinant microorganism is mutated or otherwise genetically altered such that there is substantially no expression of Hxk1 and/or Glk1 polypeptides in the cell. In an embodiment, a recombinant microorganism is mutated or otherwise genetically altered such that there is substantially no expression of Hxk1, Hxk2, Glk1 polypeptides, Ald6 polypeptides, Ura3 polypeptides, or combinations thereof in the cell.

In an embodiment a genetically engineered yeast expresses a Hxk1 polypeptide that has at least 90% identity to SEQ ID NO:74, a Hxk2 polypeptide that has at least 90% identity to SEQ ID NO: 76, a Glk1 polypeptide that has 90% identity to SEQ ID NO: 78, or combinations thereof.

In an embodiment a genetically engineered yeast has an ability to co-utilize sugars, wherein the biological activity of an endogenous protein having at least 90% sequence identity to an amino acid sequence set forth in SEQ ID NO:74, SEQ ID NO: 76, SEQ ID NO: 78, or combinations thereof is reduced or eliminated as compared to a control yeast.

A genetically engineered or recombinant microorganism can have improved sugar utilization or sugar co-utilization of two or more sugars as compared to a control or wild-type microorganism.

A genetically engineered or recombinant microorganism can additionally comprise a recombinant polynucleotide encoding a XYL1 polypeptide, a XYL2 polypeptide, a XYL3 polypeptide, or a combination thereof.

In an embodiment a genetically engineered or recombinant microorganism comprises one or more heterologous or exogenous polynucleotides, optionally operably linked to one or more heterologous, exogenous, or endogenous regulatory elements such that one or more heterologous or exogenous biologically active polypeptides are expressed by the microorganism. A genetically engineered microorganism can comprise one or more heterologous polynucleotides encoding a XYL1 polypeptide having xylose reductase activity, a XYL1 polypeptide having D-xylulose reductase activity, a XYL3 polypeptide having D-Xylulokinase activity.

XYL1 polypeptides include, for example GenBank XM_001385144.1, XYL2 polypeptides include, for example, GenBankX55392.1, XYL3 polypeptides, include, for example, GenBank XM_001387288.1, The polynucleotides encoding a Hxk1 polypeptide, a Hxk2 polypeptide, a Glk1 polypeptide, a Ald6 polypeptide, a Ura3 polypeptide can be deleted or mutated using a genetic manipulation technique selected from, for example, TALEN, Zinc Finger Nucleases, and CRSPR-Cas9.

One or more regulatory elements controlling expression of the polynucleotides encoding a Hxk1 polypeptide, a Hxk2 polypeptide, a Glk1 polypeptide, a Ald6 polypeptide, a Ura3 polypeptide, or combinations thereof can be mutated or replaced to prevent or attenuate expression of a Hxk1 polypeptide, a Hxk2 polypeptide, a Glk1 polypeptide, a Ald6 polypeptide, a Ura3 polypeptide or combinations thereof as compared to a control or wild-type microorganism. For example, a promoter can mutated or replaced such that the gene expression or polypeptide expression is attenuated or such that the Hxk1, Hxk2, Glk1, Ald6, or Ura3 polynucleotides are not transcribed. In one embodiment, one or more promoters for Hxk1, Hxk2, Glk1, Ald6, Ura3, or combinations thereof are replaced with a promoter that has weaker activity (e.g., TEF1p, CYC1p, ADH1p, ACT1p, HXT7p, PGI1p, TDH2p, PGK1p) than the wild-type promoter. A promoter with weaker activity transcribes the polynucleotide at a rate about 5, 10, 20, 30, 40, 50, 60, 70, 80, or 90% less than the wild-type promoter for that polynucleotide. In another embodiment, one or more promoters for Hxk1, Hxk2, Glk1, Ald6, Ura3, or combinations thereof are replaced with a inducible promoter (e.g., TetO promoters such as TetO3, TetO7, and CUP1p) that can be controlled to attenuate expression of Hxk1, Hxk2, Glk1, Ald6, Ura3 or combinations thereof.

The genetically engineered or recombinant microorganism can have reduced glucose consumption rate as compared to a control or wild-type microorganism.

The genetically engineered or recombinant microorganism can co-utilize two or more sugars are selected from glucose, sucrose, lactose, galactose, arabinose, mannose, fructose, xylobiose, cellobiose, xylose, rhamnose, maltose, cellodextrins, or 4-deoxy-L-erythro-5-hexoseulose uronate. In one embodiment, glucose is co-utilized with one of galactose, lactose, arabinose, mannose, fructose, xylobiose, cellobiose, xylose, rhamnose, maltose, cellodextrins, or 4-deoxy-L-erythro-5-hexoseulose uronate.

The present disclosure provides genetically engineered microorganisms lacking expression or having attenuated or reduced expression of Hxk1, Hxk2, Glk1, Ald6, Ura3 polypeptides or combinations thereof, or expression of mutant Hxk1, Hxk2, Glk1, Ald6, Ura3 polypeptides or combinations thereof that have reduced activity. A genetically engineered or recombinant microorganism can comprise a Hxk1 polypeptide that has a T89A mutation, a Hxk2 polypeptide that has a P455F mutation, a Glk1 polypeptide that has a S306P mutation, or combinations thereof. For example, in the case of Hxk1 a T89A mutation means that the T at position of the Hxk1 polypeptide is substituted with an A. An example of an Ald6 polynucleotide is GenBank CP020138.1. In an embodiment, the Ald6 gene is deleted. An example of an Ura3 polynucleotide is GenBank CP020127.1. In one embodiment, a recombinant microorganism has a Ura3-52 mutant allele, which results in a non-functional Ura3 polypeptide.

A genetically engineered or recombinant microorganism can comprise a polynucleotide encoding at least one mutant polypeptide selected from Hxk1 T89A, Hxk2 P455F, and Glk1 S306P.

The reduced expression, non-expression, or expression of mutated, inactive, or reduced activity polypeptides can be affected by deletion of the polynucleotide or gene encoding Hxk1, Hxk2 Glk1, Ald6, and Ura3 replacement of the wild-type polynucleotide or gene with mutated forms, deletion of a portion of a Hxk1, Hxk2, Glk1, Ald6, or Ura3 polynucleotide or gene or combinations thereof to cause expression of an inactive form of the polypeptides, or manipulation of the regulatory elements (e.g. promoter) to prevent or reduce expression of wild-type Hxk1, Hxk2, Glk1, Ald6, or Ura3 polypeptides. The promoter could also be replaced with a weaker promoter or an inducible promoter that leads to reduced expression of the polypeptides. Any method of genetic manipulation that leads to a lack of, or reduced expression and/or activity of Hxk1, Hxk2, Glk1, Ald6, or Ura3 polypeptides and can be used in the present methods, including expression of inhibitor RNAs (e.g. shRNA, siRNA, and the like).

Wild-type refers to a microorganism that is naturally occurring or which has not been recombinantly modified to increase or decrease transport or utilization of specific sugars. A control microorganism is a microorganism (e.g. yeast) that lacks genetic modifications of a test microorganism (e.g., yeast) and that can be used to test altered biological activity of genetically modified microorganisms (e.g., yeast).

Gene Disruptions and Mutations

A genetic mutation comprises a change or changes in a nucleotide sequence of a gene or related regulatory region or polynucleotide that alters the nucleotide sequence as compared to its native or wild-type sequence. Mutations include, for example, substitutions, additions, and deletions, in whole or in part, within the wild-type sequence. Such substitutions, additions, or deletions can be single nucleotide changes (e.g., one or more point mutations), or can be 2, 3, 4, 5, 6, 7, 8, 9, 10, or more nucleotide changes. Mutations can occur within the coding region of the gene or polynucleotide as well as within the non-coding and regulatory elements of a gene. A genetic mutation can also include silent and conservative mutations within a coding region as well as changes which alter the amino acid sequence of the polypeptide encoded by the gene or polynucleotide. A genetic mutation can, for example, increase, decrease, or otherwise alter the activity (e.g., biological activity) of the polypeptide product. A genetic mutation in a regulatory element can increase, decrease, or otherwise alter the expression of sequences operably linked to the altered regulatory element.

A gene disruption is a genetic alteration in a polynucleotide or gene that renders an encoded gene product (e.g., Hxk1, Hxk2, Glk1, Ald6, or Ura3) inactive or attenuated (e.g., produced at a lower amount or having lower biological activity). A gene disruption can include a disruption in a polynucleotide or gene that results in no expression of an encoded gene product, reduced expression of an encoded gene product, or expression of a gene product with reduced or attenuated biological activity. The genetic alteration can be, for example, deletion of the entire gene or polynucleotide, deletion of a regulatory element required for transcription or translation of the polynucleotide or gene, deletion of a regulatory element required for transcription or translation or the polynucleotide or gene, addition of a different regulatory element required for transcription or translation or the gene or polynucleotide, deletion of a portion (e.g. 1, 2, 3, 6, 9, 21, 30, 60, 90, 120 or more nucleic acids) of the gene or polynucleotide, which results in an inactive or partially active gene product, replacement of a gene's promoter with a weaker promoter, replacement or insertion of one or more amino acids of the encoded protein to reduce its activity, stability, or concentration, or inactivation of a gene's transactivating factor such as a regulatory protein. A gene disruption can include a null mutation, which is a mutation within a gene or a region containing a gene that results in the gene not being transcribed into RNA and/or translated into a functional gene product. An inactive gene product has no biological activity.

Zinc-finger nucleases (ZFNs), Talens, and CRSPR-Cas9 allow double strand DNA cleavage at specific sites in yeast chromosomes such that targeted gene insertion or deletion can be performed (Shukla et al., 2009, Nature 459:437-441; Townsend et al., 2009, Nature 459:442-445). This approach can be used to modify the promoter of endogenous genes or the endogenous genes themselves to modify expression of Hxk1, Hxk2, Glk1, Ald6, or Ura3 which can be present in the genome of yeast of interest. ZFNs, Talens or CRSPR/Cas9 can be used to change the sequences regulating the expression of the polypeptides to increase or decrease the expression or alter the timing of expression beyond that found in a non-engineered or wild-type yeast, or to delete the wild-type polynucleotide, or replace it with a deleted or mutated form to alter the expression and/or activity of Hxk1, Hxk2, Glk1, Ald6 and Ura3.

Polynucleotides and Genes

Polynucleotides contain less than an entire microbial genome and can be single- or double-stranded nucleic acids. A polynucleotide can be RNA, DNA, cDNA, genomic DNA, chemically synthesized RNA or DNA or combinations thereof. A polynucleotide can comprise, for example, a gene, open reading frame, non-coding region, or regulatory element.

A gene is any polynucleotide molecule that encodes a polypeptide, protein, or fragments thereof, optionally including one or more regulatory elements preceding (5' non-coding sequences) and following (3' non-coding sequences) the coding sequence. In one embodiment, a gene does not include regulatory elements preceding and following the coding sequence. A native or wild-type gene refers to a gene as found in nature, optionally with its own regulatory elements preceding and following the coding sequence. A chimeric or recombinant gene refers to any gene that is not a native or wild-type gene, optionally comprising regulatory elements preceding and following the coding sequence, wherein the coding sequences and/or the regulatory elements, in whole or in part, are not found together in nature. Thus, a chimeric gene or recombinant gene comprise regulatory elements and coding sequences that are derived from different sources, or regulatory elements and coding sequences that are derived from the same source, but arranged differently than is found in nature. A gene can encompass full-length gene sequences (e.g., as found in nature and/or a gene sequence encoding a full-length polypeptide or protein) and can also encompass partial gene sequences (e.g., a fragment of the gene sequence found in nature and/or a gene sequence encoding a protein or fragment of a polypeptide or protein). A gene can include modified gene sequences (e.g., modified as compared to the sequence found in nature). Thus, a gene is not limited to the natural or full-length gene sequence found in nature.

Polynucleotides can be purified free of other components, such as proteins, lipids and other polynucleotides. For example, the polynucleotide can be 50%, 75%, 90%, 95%, 96%, 97%, 98%, 99%, or 100% purified. A polynucleotide existing among hundreds to millions of other polynucleotide molecules within, for example, cDNA or genomic libraries, or gel slices containing a genomic DNA restriction digest are not to be considered a purified polynucleotide. Polynucleotides can encode the polypeptides described herein (e.g., Hxk1, Hxk2, Glk1, Ald6, Ura3, Xyl1, Xyl1, Xyl3, and mutants or variants thereof).

Polynucleotides can comprise additional heterologous nucleotides that do not naturally occur contiguously with the polynucleotides. As used herein the term "heterologous" refers to a combination of elements that are not naturally occurring or that are obtained from different sources.

Polynucleotides can comprise other nucleotide sequences, such as sequences coding for linkers, signal sequences, TMR stop transfer sequences, transmembrane domains, or ligands useful in protein purification such as glutathione-S-transferase, histidine tag, and Staphylococcal protein A.

Polynucleotides can be isolated. An isolated polynucleotide is a naturally-occurring polynucleotide that is not immediately contiguous with one or both of the 5' and 3' flanking genomic sequences that it is naturally associated with. An isolated polynucleotide can be, for example, a recombinant DNA molecule of any length, provided that the nucleic acid sequences naturally found immediately flanking the recombinant DNA molecule in a naturally-occurring genome is removed or absent. Isolated polynucleotides also include non-naturally occurring nucleic acid molecules. Polynucleotides can encode full-length polypeptides, polypeptide fragments, and variant or fusion polypeptides.

Degenerate polynucleotide sequences encoding polypeptides described herein, as well as homologous nucleotide sequences that are at least about 80, or about 85, 90, 91, 92, 93, 94, 95, 96, 97, 98, or 99% identical to polynucleotides described herein and the complements thereof are also polynucleotides. Degenerate nucleotide sequences are polynucleotides that encode a polypeptide described herein or fragments thereof, but differ in nucleic acid sequence from the wild-type polynucleotide sequence, due to the degeneracy of the genetic code. Complementary DNA (cDNA) molecules, species homologs, and variants of polynucleotides that encode biologically functional polypeptides also are polynucleotides.

Polynucleotides can be obtained from nucleic acid sequences present in, for example, a microorganism such as a yeast or bacterium. Polynucleotides can also be synthesized in the laboratory, for example, using an automatic synthesizer. An amplification method such as PCR can be used to amplify polynucleotides from either genomic DNA or cDNA encoding the polypeptides.

Polynucleotides can comprise coding sequences for naturally occurring polypeptides or can encode altered sequences that do not occur in nature.

Unless otherwise indicated, the term polynucleotide or gene includes reference to the specified sequence as well as the complementary sequence thereof.

The expression products of genes or polynucleotides are often proteins, or polypeptides, but in non-protein coding genes such as rRNA genes or tRNA genes, the product is a functional RNA. The process of gene expression is used by all known life forms, i.e., eukaryotes (including multicellular organisms), prokaryotes (bacteria and archaea), and viruses, to generate the macromolecular machinery for life. Several steps in the gene expression process can be modulated, including the transcription, upregulation, RNA splicing, translation, and post-translational modification of a protein. Any process that deletes, reduces, or attenuates the expression of Hxk1, Hxk2, and Glk1 protein expression can be used to make a microorganism capable of sugar co-utilization.

Polypeptides

A polypeptide is a polymer of two or more amino acids covalently linked by amide bonds. A polypeptide can be post-translationally modified. A purified polypeptide is a polypeptide preparation that is substantially free of cellular material, other types of polypeptides, chemical precursors, chemicals used in synthesis of the polypeptide, or combinations thereof. A polypeptide preparation that is substantially free of cellular material, culture medium, chemical precursors, chemicals used in synthesis of the polypeptide, etc., has less than about 30%, 20%, 10%, 5%, 1% or more of other polypeptides, culture medium, chemical precursors, and/or other chemicals used in synthesis. Therefore, a purified polypeptide is about 70%, 80%, 90%, 95%, 99% or more pure. A purified polypeptide does not include unpurified or semi-purified cell extracts or mixtures of polypeptides that are less than 70% pure.

The term "polypeptides" can refer to one or more of one type of polypeptide (a set of polypeptides). "Polypeptides" can also refer to mixtures of two or more different types of polypeptides (a mixture of polypeptides). The terms "polypeptides" or "polypeptide" can each also mean "one or more polypeptides."

As used herein, the term "polypeptide of interest" or "polypeptides of interest", "protein of interest", "proteins of interest" includes any or a plurality of any of the Hxk1, Hxk2, Glk1, Ald6, Ura3, Xyl1, Xyl2, Xyl3 polypeptides or other polypeptides described herein.

A mutated protein or polypeptide comprises at least one deleted, inserted, and/or substituted amino acid, which can be accomplished via mutagenesis of polynucleotides encoding these amino acids. Mutagenesis includes well-known methods in the art, and includes, for example, site-directed mutagenesis by means of PCR or via oligonucleotide-mediated mutagenesis as described in Sambrook et al., Molecular Cloning-A Laboratory Manual, 2nd ed., Vol. 1-3 (1989).

As used herein, the term "sufficiently similar" means a first amino acid sequence that contains a sufficient or minimum number of identical or equivalent amino acid residues relative to a second amino acid sequence such that the first and second amino acid sequences have a common structural domain and/or common functional activity. For example, amino acid sequences that comprise a common structural domain that is at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100%, identical are defined herein as sufficiently similar Variants will be sufficiently similar to the amino acid sequence of the polypeptides described herein. Such variants generally retain the functional activity of the polypeptides described herein. Variants include peptides that differ in amino acid sequence from the native and wild-type peptide, respectively, by way of one or more amino acid deletion(s), addition(s), and/or substitution(s). These may be naturally occurring variants as well as artificially designed ones.

As used herein, the term "percent (%) sequence identity" or "percent (%) identity," also including "homology," is defined as the percentage of amino acid residues or nucleotides in a candidate sequence that are identical with the amino acid residues or nucleotides in the reference sequences after aligning the sequences and introducing gaps, if necessary, to achieve the maximum percent sequence identity, and not considering any conservative substitutions as part of the sequence identity. Optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl. Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

Polypeptides and polynucleotides that are sufficiently similar to polypeptides and polynucleotides described herein (e.g., Hxk1, Hxk2, Glk1, and Ald6, Ura3, Xyl1, Xyl2, Xyl3) can be used herein. Polypeptides and polynucleotides that about 85, 90, 95, 96, 97, 98, 99% or more homology or identity to polypeptides and polynucleotides described herein (e.g., Hxk1, Hxk2, Glk1, Ald6, Ura3, Xyl1, Xyl2, Xyl3) can also be used herein.

Constructs and Cassettes

A recombinant construct is a polynucleotide having heterologous polynucleotide elements. Recombinant constructs include expression cassettes or expression constructs, which refer to an assembly that is capable of directing the expression of a polynucleotide or gene of interest. An expression cassette generally includes regulatory elements such as a promoter that is operably linked to (so as to direct transcription of) a polynucleotide and often includes a polyadenylation sequence as well.

An "expression cassette" refers to a fragment of DNA comprising a coding sequence of a selected gene (e.g. Hxk1, Hxk2, Glk1, Ald6, Ura3, Xyl1, Xyl2, Xyl3) and regulatory elements preceding (5' non-coding sequences) and following (3' non-coding sequences) the coding sequence that are required for expression of the selected gene product. Thus, an expression cassette is typically composed of: 1) a promoter sequence; 2) a coding sequence ["ORF"]; and, 3) a 3' untranslated region (i.e., a terminator) that, in eukaryotes, usually contains a polyadenylation site. The expression cassette is usually included within a vector, to facilitate cloning and transformation. Different expression cassettes can be transformed into different organisms including bacteria, yeast, plants and mammalian cells, as long as the correct regulatory elements are used for each host.

A recombinant construct or expression cassette can be contained within a vector. In addition to the components of the recombinant construct, the vector can include, one or more selectable markers, a signal which allows the vector to exist as single-stranded DNA (e.g., a M13 origin of replication), at least one multiple cloning site, and a origin of replication (e.g., a SV40 or adenovirus origin of replication).

Generally, a polynucleotide or gene that is introduced into a genetically engineered organism is part of a recombinant construct. A polynucleotide can comprise a gene of interest, e.g., a coding sequence for a protein, or can be a sequence that is capable of regulating expression of a gene, such as a regulatory element, an antisense sequence, a sense suppression sequence, or a miRNA sequence. A recombinant construct can include, for example, regulatory elements operably linked 5' or 3' to a polynucleotide encoding one or more polypeptides of interest. For example, a promoter can be operably linked with a polynucleotide encoding one or more polypeptides of interest when it is capable of affecting the expression of the polynucleotide (i.e., the polynucleotide is under the transcriptional control of the promoter). Polynucleotides can be operably linked to regulatory elements in sense or antisense orientation. The expression cassettes or recombinant constructs can additionally contain a 5' leader polynucleotide. A leader polynucleotide can contain a promoter as well as an upstream region of a gene. The regulatory elements (i.e., promoters, enhancers, transcriptional regulatory regions, translational regulatory regions, and translational termination regions) and/or the polynucleotide encoding a signal anchor can be native/endogenous to the host cell or to each other. Alternatively, the regulatory elements can be heterologous to the host cell or to each other. See, U.S. Pat. No. 7,205,453 and U.S. Patent Application Publication Nos. 2006/0218670 and 2006/0248616. The expression cassette or recombinant construct can additionally contain one or more selectable marker genes.

Methods for preparing polynucleotides operably linked to a regulatory elements and expressing polypeptides in a host cell are well-known in the art. See, e.g., U.S. Pat. No. 4,366,246. A polynucleotide can be operably linked when it is positioned adjacent to or close to one or more regulatory elements, which direct transcription and/or translation of the polynucleotide.

A promoter is a nucleotide sequence that is capable of controlling the expression of a coding sequence or gene. Promoters are generally located 5' of the sequence that they regulate. Promoters may be derived in their entirety from a native gene, or be composed of different elements derived from promoters found in nature, and/or comprise synthetic nucleotide segments. Those skilled in the art will readily ascertain that different promoters may regulate expression of a coding sequence or gene in response to a particular stimulus, e.g., in a cell- or tissue-specific manner, in response to different environmental or physiological conditions, or in response to specific compounds. Promoters are typically classified into two classes: inducible and constitutive. A constitutive promoter refers to a promoter that allows for continual transcription of the coding sequence or gene under its control.

An inducible promoter refers to a promoter that initiates increased levels of transcription of the coding sequence or gene under its control in response to a stimulus or an exogenous environmental condition. If inducible, there are inducer polynucleotides present therein that mediate regulation of expression so that the associated polynucleotide is transcribed only when an inducer molecule is present. A directly inducible promoter refers to a regulatory region, wherein the regulatory region is operably linked to a gene encoding a protein or polypeptide, where, in the presence of an inducer of said regulatory region, the protein or polypeptide is expressed. An indirectly inducible promoter refers to a regulatory system comprising two or more regulatory regions, for example, a first regulatory region that is operably linked to a first gene encoding a first protein, polypeptide, or factor, e.g., a transcriptional regulator, which is capable of regulating a second regulatory region that is operably linked to a second gene, the second regulatory region may be activated or repressed, thereby activating or repressing expression of the second gene. Both a directly inducible promoter and an indirectly inducible promoter are encompassed by inducible promoter.

A promoter can be any polynucleotide that shows transcriptional activity in the chosen host microorganism. A promoter can be naturally-occurring, can be composed of portions of various naturally-occurring promoters, or may be partially or totally synthetic. Guidance for the design of promoters is derived from studies of promoter structure, such as that of Harley and Reynolds, *Nucleic Acids Res.*, 15, 2343-61 (1987). In addition, the location of the promoter relative to the transcription start can be optimized. Many suitable promoters for use in microorganisms and yeast are well known in the art, as are polynucleotides that enhance expression of an associated expressible polynucleotide.

A selectable marker can provide a means to identify microorganisms that express a desired product. Selectable markers include, but are not limited to, ampicillin resistance for prokaryotes such as *E. coli*, neomycin phosphotransferase, which confers resistance to the aminoglycosides neomycin, kanamycin and paromycin (Herrera-Estrella, *EMBO J.* 2:987-995, (1983)); dihydrofolate reductase, which confers resistance to methotrexate (Reiss, *Plant Physiol.* (*Life Sci.* Adv.) 13:143-149, (1994)); trpB, which allows cells to utilize indole in place of tryptophan; hisD, which allows cells to utilize histinol in place of histidine (Hartman, *Proc. Natl. Acad. Sci., USA* 85:8047, (1988)); mannose-6-phosphate isomerase which allows cells to utilize mannose (WO 94/20627); hygro, which confers resistance to hygromycin (Marsh, *Gene* 32:481-485, (1984)); ornithine decarboxylase, which confers resistance to the ornithine decarboxylase inhibitor, 2-(difluoromethyl)-DL-ornithine (DFMO; McConlogue, In: *Current Communications in Molecular Biology*, Cold Spring Harbor Laboratory ed., (1987)); deaminase from *Aspergillus terreus*, which confers resistance to Blasticidin S (Tamura, *Biosci. Biotechnol. Biochem.* 59:2336-2338, (1995)); phosphinothricin acetyltransferase gene, which confers resistance to phosphinothricin (White et al., *Nucl. Acids Res.* 18:1062, (1990); Spencer et al., *Theor. Appl. Genet.* 79:625-633, (1990)); a mutant acetolactate synthase, which confers imidazolione or sulfonylurea resistance (Lee et al., *EMBO J.* 7:1241-1248, (1988)), a mutant EPSPV-synthase, which confers glyphosate resistance (Hinchee et al., *BioTechnology* 91:915-922, (1998)); a mutant psbA, which confers resistance to atrazine (Smeda et al., *Plant Physiol.* 103:911-917, (1993)), a mutant protoporphyrinogen oxidase (see U.S. Pat. No. 5,767,373), or other markers conferring resistance to an herbicide such as glufosinate.

A transcription termination region of a recombinant construct or expression cassette is a downstream regulatory region including a stop codon and a transcription terminator sequence. Transcription termination regions that can be used can be homologous to the transcriptional initiation region, can be homologous to the polynucleotide encoding a polypeptide of interest, or can be heterologous (i.e., derived from another source). A transcription termination region or can be naturally occurring, or wholly or partially synthetic. 3' non-coding sequences encoding transcription termination regions may be provided in a recombinant construct or expression construct and may be from the 3' region of the gene from which the initiation region was obtained or from a different gene. A large number of termination regions are known and function satisfactorily in a variety of hosts when utilized in both the same and different genera and species from which they were derived. Termination regions may also be derived from various genes native to the preferred hosts. The termination region is usually selected more for convenience rather than for any particular property.

The procedures described herein employ, unless otherwise indicated, conventional techniques of chemistry, molecular biology, microbiology, recombinant DNA, genetics, immunology, cell biology, cell culture and transgenic biology, which are within the skill of the art. (See, e.g., Maniatis, et al., *Molecular Cloning*, Cold Spring Harbor Laboratory Press, Cold Spring Harbor, N.Y. (1982); Sambrook, et al., (1989); Sambrook and Russell, *Molecular Cloning*, 3rd Ed., Cold Spring Harbor Laboratory Press, Cold Spring Harbor, N.Y. (2001); Ausubel, et al., *Current Protocols in Molecular Biology*, John Wiley & Sons (including periodic updates) (1992); *Glover, DNA Cloning*, IRL Press, Oxford (1985); Russell, *Molecular biology of plants: a laboratory course manual*, Cold Spring Harbor Laboratory Press, Cold Spring Harbor, N.Y. (1984); Anand, *Techniques for the Analysis of Complex Genomes*, Academic Press, N Y (1992); Guthrie and Fink, *Guide to Yeast Genetics and Molecular Biology*, Academic Press, N Y (1991); Harlow and Lane, *Antibodies*, Cold Spring Harbor Laboratory Press, Cold Spring Harbor, N.Y. (1988); *Nucleic Acid Hybridization*, B. D. Hames & S. J. Higgins eds. (1984); *Transcription And Translation*, B. D. Hames & S. J. Higgins eds. (1984); *Culture Of Animal Cells*, R. I. Freshney, A. R. Liss, Inc.

(1987); *Immobilized Cells And Enzymes*, IRL Press (1986); B. Perbal, *A Practical Guide To Molecular Cloning* (1984); the treatise, *Methods In Enzymology*, Academic Press, Inc., NY); *Methods In Enzymology*, Vols. 154 and 155, Wu, et al., eds.; *Immunochemical Methods In Cell And Molecular Biology*, Mayer and Walker, eds., Academic Press, London (1987); *Handbook Of Experimental Immunology*, Volumes I-IV, D. M. Weir and C. C. Blackwell, eds. (1986); Riott, *Essential Immunology*, 6th Edition, Blackwell Scientific Publications, Oxford (1988); Fire, et al., *RNA Interference Technology From Basic Science to Drug Development*, Cambridge University Press, Cambridge (2005); Schepers, *RNA Interference in Practice*, Wiley-VCH (2005); Engelke, *RNA Interference (RNAi): The Nuts & Bolts of siRNA Technology*, DNA Press (2003); Gott, *RNA Interference, Editing, and Modification: Methods and Protocols* (*Methods in Molecular Biology*), Human Press, Totowa, N.J. (2004); and Sohail, *Gene Silencing by RNA Interference: Technology and Application*, CRC (2004)).

Vectors

Vectors for stable transformation of microorganisms and yeast are well known in the art and can be obtained from commercial vendors or constructed from publicly available sequence information. Expression vectors can be engineered to produce heterologous and/or homologous protein(s) of interest (e.g., Hxk1, Hxk2, Glk1, Ald6, Ura3, Xyl1, Xyl2, Xyl3.). Such vectors are useful for recombinantly producing a protein of interest and for modifying the natural phenotype of host cells.

If desired, polynucleotides can be cloned into an expression vector comprising expression control elements, including for example, origins of replication, promoters, enhancers, or other regulatory elements that drive expression of the polynucleotides in host cells. An expression vector can be, for example, a plasmid, such as pBR322, pUC, or ColE1, or an adenovirus vector, such as an adenovirus Type 2 vector or Type 5 vector. Optionally, other vectors can be used, including but not limited to Sindbis virus, simian virus 40, alphavirus vectors, poxvirus vectors, and cytomegalovirus and retroviral vectors, such as murine sarcoma virus, mouse mammary tumor virus, Moloney murine leukemia virus, and Rous sarcoma virus. Minichromosomes such as MC and MC1, bacteriophages, phagemids, yeast artificial chromosomes, bacterial artificial chromosomes, virus particles, virus-like particles, cosmids (plasmids into which phage lambda cos sites have been inserted) and replicons (genetic elements that are capable of replication under their own control in a cell) can also be used.

To confirm the presence of recombinant polynucleotides or recombinant genes in transgenic cells, a polymerase chain reaction (PCR) amplification or Southern blot analysis can be performed using methods known to those skilled in the art. Expression products of the recombinant polynucleotides or recombinant genes can be detected in any of a variety of ways, and include for example, western blot and enzyme assay. Once recombinant organisms have been obtained, they may be grown in cell culture.

Methods of Use

Embodiments provide methods of co-utilizing or co-fermenting two or more sugars with genetically modified microorganisms described herein. A genetically modified organism is contacted with the two or more sugars under fermentation conditions such that the two of more sugars are co-utilized or co-fermented.

Two or more sugars can be present in, for example, feedstocks such as terrestrial biomass feedstock (e.g., lignocellulosic biomass feedstock) or marine biomass feedstock. Feedstocks are substance used as a raw material for the growth of an organism, including an industrial growth process. A feedstock can be the raw material used to supply a carbon or other energy source for a recombinant microorganism.

In co-utilization or co-fermentation processes a genetically modified microorganism is cultivated in a fermentation medium that includes two or more sugars. A batch or continuous fermentation process can be used. The sugars can be, for example, pentose or hexose sugars, the sugars can be, for example, glucose, galactose, lactose, sucrose, arabinose, mannose, fructose, xylobiose, cellobiose, xylose, rhamnose, maltose, cellodextrins, or 4-deoxy-L-erythro-5-hexoseulose uronate. In an embodiment, two of more of the sugars are co-utilized or co-fermented. The fermentation medium can contain nutrients as required by the particular microorganism, including a source of nitrogen (such as amino acids proteins, inorganic nitrogen sources such as ammonia or ammonium salts, and the like), and various vitamins, minerals and the like.

Fermentation conditions, such as temperature, cell density, selection of substrate(s), selection of nutrients, and can be determined by those of skill in the art. Temperatures of the medium during each of the growth phase and the production phase can range from above about 1° C. to about 50° C. The optimal temperature can depend on the particular microorganism used. In an embodiment, the temperature is about 30, 35, 40, 45, 50° C.

During the production phase, the concentration of cells in the fermentation medium can be in the range of about 1 to about 150, about 3 to about 10, or about 3 to about 6 g dry cells/liter of fermentation medium.

A fermentation can be conducted aerobically, microaerobically or anaerobically. Fermentation medium can be buffered during the fermentation so that the pH is maintained in a range of about 5.0 to about 9.0, or about 5.5 to about 7.0. Suitable buffering agents include, for example, calcium hydroxide, calcium carbonate, sodium hydroxide, potassium hydroxide, potassium carbonate, sodium carbonate, ammonium carbonate, ammonia, ammonium hydroxide and the like.

The fermentation methods can be conducted continuously, batch-wise, or some combination thereof.

A fermentation reaction can be conducted over about 1, 2, 5, 10, 15, 20, 24, 25, 30, 36, 48, or more or hours. Co-utilization determinations of two or more sugars can be conducted after about 1, 2, 5, 10, 15, 20, 24, 25, 30, 36, 48, or more or hours of fermentation by recombinant microorganisms.

Methods of producing ethanol are provided herein. Genetically engineered microorganisms described herein can be or more sugars under fermentation conditions such that the two of more sugars are co-utilized or co-fermented such that ethanol is produced. A fermentation reaction can be conducted over about 1, 2, 5, 10, 15, 20, 24, 25, 30, 36, 48, or more or hours. Other products can be made using the microorganisms described herein, including, for example, isobutanol, 1,3-butanediol, xylitol, glycerol, isoprene, 2-fucosyllactose, amorphadiene, artemisinin, squalene, beta-carotene, retinol poly[(R)-3-hydroxybutyrate], naringenin, pinocembrin, glucosamine, myo-inositol, scyllo-inositol, lactic acid, cinnamic acid, and L-ascorbic acid.

Genetically modified microorganisms can be engineered to also include expression or deletion/inhibition of additional polypeptides that may increase efficiency of particular sugar utilization pathways. For example, a microorganism can be engineered to have increased xylose utilization, such as by including one or more polynucleotides capable of expression of XYL1, XYL2, or XYL3.

Sequences

```
Wild-type HXK1                              SEQ ID NO: 1
ATGGTTCATTTAGGTCCAAAGAAACCACAGGCTAGAAAGGGTTCCATGGC
TGATGTGCCCAAGGAATTGATGGATGAAATTCATCAGTTGGAAGATATGT
TTACAGTTGACAGCGAGACCTTGAGAAAGGTTGTTAAGCACTTTATCGAC
GAATTGAATAAAGGTTTGACAAAGAAGGGAGGTAACATTCCAATGATTCC
CGGTTGGGTCATGGAATTCCCAACAGGTAAAGAATCTGGTAACTATTTGG
CCATTGATTTGGGTGGTACTAACTTAAGAGTCGTGTTGGTCAAGTTGAGC
GGTAACCATACCTTTGACACCACTCAATCCAAGTATAAACATACCACATGA
CATGAGAACCACTAAGCACCAAGAGGAGTTATGGTCCTTTATTGCCGACT
CTTTGAAGGACTTTATGGTCGAGCAAGAATTGCTAAACACCAAGGACACC
TTACCATTAGGTTTCACCTTCTCGTACCCAGCTTCCCAAAACAAGATTAA
CGAAGGTATTTTGCAAAGATGGACCAAGGGTTTCGATATTCCAAATGTCG
AAGGCCACGATGTCGTCCCATTGCTACAAAACGAAATTTCCAAGAGAGAG
TTGCCTATTGAAATTGTAGCATTGATTAATGATACTGTTGGTACTTTAAT
TGCCTCATACTACACTGACCCAGAGACTAAGATGGGTGTGATTTTCGGTA
CTGGTGTCAACGGTGCTTTCTATGATGTTGTTTCCGATATCGAAAAGTTG
GAGGGCAAATTAGCAGACGATATTCCAAGTAACTCTCCAATGGCTATCAA
TTGTGAATATGGTTCCTTCGATAATGAACATTTGGTCTTGCCAAGAACCA
AGTACGATGTTGCTGTCGACGAACAATCTCCAAGACCTGGTCAACAAGCT
TTTGAAAAGATGACCCCCGGTTACTACTTGGGTGAATTGTTGCGTCTAGT
GTTACTTGAATTAAACGAGAAGGGCTTGATGTTGAAGGATCAAGATCTAA
GCAAGTTGAAACAACCATACATCATGGATACCTCCTACCCAGCAAGAATC
GAGGATGATCCATTTGAAAACTTGGAAGATACTGATGACATCTTCCAAAA
GGACTTTGGTGTCAAGACCACTCTGCCAGAACGTAAGTTGATTAGAAGAC
TTTGTGAATTGATCGGTACCAGAGCTGCTAGATTAGCTGTTTGTGGTATT
GCCGCTATTTGCCAAAAGAGAGGTTACAAGACTGGTCACATTGCCGCTGA
CGGTTCTGTCTATAACAAATACCCAGGTTTCAAGGAAGCCGCCGCTAAGG
GTTTGAGAGATATCTATGGATGGACTGGTGACGCAAGCAAAGATCCAATT
ACGATTGTTCCAGCTGAGGATGGTTCAGGTGCAGGTGCTGCTGTTATTGC
TGCATTGTCCGAAAAAAGAATTGCCGAAGGTAAGTCTCTTGGTATCATTG
GCGCTTAA Mutant HXK1                                 SEQ ID NO: 2
ATGGTTCATTTAGGTCCAAAGAAACCACAGGCTAGAAAGGGTTCCATGGC
TGATGTGCCCAAGGAATTGATGGATGAAATTCATCAGTTGGAAGATATGT
TTACAGTTGACAGCGAGACCTTGAGAAAGGTTGTTAAGCACTTTATCGAC
GAATTGAATAAAGGTTTGACAAAGAAGGGAGGTAACATTCCAATGATTCC
CGGTTGGGTCATGGAATTCCCAACAGGTAAAGAATCTGGTAACTATTTGG
CCATTGATTTGGGTGGTACTAACTTAAGAGTCGTGTTGGTCAAGTTGAGC
GGTAACCATACCTTTGACACCACTCAATCCAAGTATAAACATACCACATGA
CATGAGAACCACTAAGCACCAAGAGGAGTTATGGTCCTTTATTGCCGACT
CTTTGAAGGACTTTATGGTCGAGCAAGAATTGCTAAACACCAAGGACACC
TTACCATTAGGTTTCACCTTCTCGTACCCAGCTTCCCAAAACAAGATTAA
CGAAGGTATTTTGCAAAGATGGACCAAGGGTTTCGATATTCCAAATGTCG
AAGGCCACGATGTCGTCCCATTGCTACAAAACGAAATTTCCAAGAGAGAG
TTGCCTATTGAAATTGTAGCATTGATTAATGATACTGTTGGTACTTTAAT
TGCCTCATACTACACTGACCCAGAGACTAAGATGGGTGTGATTTTCGGTA
CTGGTGTCAACGGTGCTTTCTATGATGTTGTTTCCGATATCGAAAAGTTG
GAGGGCAAATTAGCAGACGATATTCCAAGTAACTCTCCAATGGCTATCAA
TTGTGAATATGGTTCCTTCGATAATGAACATTTGGTCTTGCCAAGAACCA
AGTACGATGTTGCTGTCGACGAACAATCTCCAAGACCTGGTCAACAAGCT
TTTGAAAAGATGACCCCCGGTTACTACTTGGGTGAATTGTTGCGTCTAGT
GTTACTTGAATTAAACGAGAAGGGCTTGATGTTGAAGGATCAAGATCTAA
GCAAGTTGAAACAACCATACATCATGGATACCTCCTACCCAGCAAGAATC
GAGGATGATCCATTTGAAAACTTGGAAGATACTGATGACATCTTCCAAAA
GGACTTTGGTGTCAAGACCACTCTGCCAGAACGTAAGTTGATTAGAAGAC
TTTGTGAATTGATCGGTACCAGAGCTGCTAGATTAGCTGTTTGTGGTATT
GCCGCTATTTGCCAAAAGAGAGGTTACAAGACTGGTCACATTGCCGCTGA
CGGTTCTGTCTATAACAAATACCCAGGTTTCAAGGAAGCCGCCGCTAAGG
GTTTGAGAGATATCTATGGATGGACTGGTGACGCAAGCAAAGATCCAATT
ACGATTGTTCCAGCTGAGGATGGTTCAGGTGCAGGTGCTGCTGTTATTGC
TGCATTGTCCGAAAAAAGAATTGCCGAAGGTAAGTCTCTTGGTATCATTG
GCGCTTAA Wild-type HXK2                              SEQ ID NO: 3
ATGGTTCATTTAGGTCCAAAAAAACCACAAGCCAGAAAGGGTTCCATGGCC
GATGTGCCAAAGGAATTGATGCAACAAATTGAGAATTTTGAAAAAATTT
TCACTGTTCCAACTGAAACTTTACAAGCCGTTACCAAGCACTTCATTTCC
GAATTGGAAAAGGGTTTGTCCAAGAAGGGTGGTAACATTCCAATGATTCC
AGGTTGGGTTATGGATTTCCCAACTGGTAAGGAATCCGGTGATTTCTTGG
CCATTGATTTGGGTGGTACCAACTTGAGAGTTGTCTTAGTCAAGTTGGGC
GGTGACCGTACCTTTGACACCACTCAATCAAGTACAGATTACCAGATGC
TATGAGAACTACTCAAAATCCAGACGAATTGTGGGAATTTATTGCCGACT
CTTTGAAAGCTTTTATTGATGAGCAATTCCCACAAGGTATCTCTGAGCCA
ATTCCATTGGGTTTCACCTTTTCTTTCCCAGCTTCTCAAAACAAAATCAA
```

-continued

Sequences

```
TGAAGGTATCTTGCAAAGATGGACTAAAGGTTTTGATATTCCAAACATTG
AAAACCACGATGTTGTTCCAATGTTGCAAAAGCAAATCACTAAGAGGAAT
ATCCCAATTGAAGTTGTTGCTTTGATAAACGACACTACCGGTACTTTGGT
TGCTTCTTACTACACTGACCCAGAAACTAAGATGGGTGTTATCTTCGGTA
CTGGTGTCAATGGTGCTTACTACGATGTTTGTTCCGATATCGAAAAGCTA
CAAGGAAAACTATCTGATGACATTCCACCATCTGCTCCAATGGCCATCAA
CTGTGAATACGGTTCCTTCGATAATGAACATGTCGTTTTGCCAAGAACTA
AATACGATATCACCATTGATGAAGAATCTCCAAGACCAGGCCAACAAACC
TTTGAAAAATGTCTTCTGGTTACTACTTAGGTGAAATTTTGCGTTTGGC
CTTGATGGACATGTACAAACAAGGTTTCATCTTCAAGAACCAAGACTTGT
CTAAGTTCGACAAGCCTTTCGTCATGGACACTTCTTACCCAGCCAGAATC
GAGGAAGATCCATTCGAGAACCTAGAAGATACCGATGACTTGTTCCAAAA
TGAGTTCGGTATCAACACTACTGTTCAAGAACGTAAATTGATCAGACGTT
TATCTGAATTGATTGGTGCTAGAGCTGCTAGATTGTCCGTTTGTGGTATT
GCTGCTATCTGTCAAAAGAGAGGTTACAAGACCGGTCACATCGCTGCAGA
CGGTTCCGTTTACAACAGATACCCAGGTTTCAAAGAAAAGGCTGCCAATG
CTTTGAAGGACATTTACGGCTGGACTCAAAACCTCACTAGACGACTACCCA
ATCAAGATTGTTCCTGCTGAAGATGGTTCCGGTGCTGGTGCCGCTGTTAT
TGCTGCTTTGGCCCAAAAAAGAATTGCTGAAGGTAAGTCCGTTGGTATCA
TCGGTGCTTAA

Mutant HXK2                                 SEQ ID NO: 71
ATGGTTCATTTAGGTCCAAAAAAACCACAAGCCAGAAAGGTTCCATGGCC
GATGTGCCAAAGGAATTGATGCAACAAATTGAGAATTTTGAAAAAATTTT
CACTGTTCCAACTGAAACTTTACAAGCCGTTACCAAGCACTTCATTTCCG
AATTGGAAAAGGGTTTGTCCAAGAAGGGTGGTAACATTCCAATGATTCCA
GGTTGGGTTATGGATTTCCCAACTGGTAAGGAATCCGGTGATTTCTTGGC
CATTGATTTGGGTGGTACCAACTTGAGAGTTGTCTTAGTCAAGTTGGGCG
GTGACCGTACCTTTGACACCACTCAATCTAAGTACAGATTACCAGATGCT
ATGAGAACTACTCAAAATCCAGACGAATTGTGGGAATTTATTGCCGACTC
TTTGAAAGCTTTTATTGATGAGCAATTCCCACAAGGTATCTCTGAGCCAA
TTCCATTGGGTTTCACCTTTTCTTTCCCAGCTTCTCAAAACAAAATCAAT
GAAGGTATCTTGCAAAGATGGACTAAAGGTTTTGATATTCCAAACATTGA
AAACCACGATGTTGTTCCAATGTTGCAAAAGCAAATCACTAAGAGGAATA
TCCCAATTGAAGTTGTTGCTTTGATAAACGACACTACCGGTACTTTGGTT
GCTTCTTACTACACTGACCCAGAAACTAAGATGGGTGTTATCTTCGGTAC
TGGTGTCAATGGTGCTTACTACGATGTTTGTTCCGATATCGAAAAGCTAC
AAGGAAAACTATCTGATGACATTCCACCATCTGCTCCAATGGCCATCAAC
TGTGAATACGGTTCCTTCGATAATGAACATGTCGTTTTGCCAAGAACTAA
ATACGATATCACCATTGATGAAGAATCTCCAAGACCAGGCCAACAAACCT
TTGAAAAATGTCTTCTGGTTACTACTTAGGTGAAATTTTGCGTTTGGCC
TTGATGGACATGTACAAACAAGGTTTCATCTTCAAGAACCAAGACTTGTC
TAAGTTCGACAAGCCTTTCGTCATGGACACTTCTTACCCAGCCAGAATCG
AGGAAGATCCATTCGAGAACCTAGAAGATACCGATGACTTGTTCCAAAAT
GAGTTCGGTATCAACACTACTGTTCAAGAACGTAAATTGATCAGACGTTTA
TCTGAATTGATTGGTGCTAGAGCTGCTAGATTGTCCGTTTGTGGTATTGC
TGCTATCTGTCAAAAGAGAGGTTACAAGACCGGTCACATCGCTGCAGACG
GTTCCGTTTACAACAGATACCCAGGTTTCAAAGAAAAGGCTGCCAATGCT
TTGAAGGACATTTACGGCTGGACTCAAACCTCACTAGACGACTACCCAA
CAAGATTGTTCTGCTGAAGATGGTTCCGGTGCTGGTGCCGCTGTTATTGC
TGCTTTGGCCCAAAAAAGAATTGCTGAAGGTAAGTCCGTTGGTATCATCG
GTGCTTAAACTTAATTTGTAA Wild-type GLK1                              SEQ ID NO: 72
ATGTCATTCGACGACTTACACAAAGCCACTGAGAGAGCGGTCATCCAGGC
CGTGGACCAGATCTGCGACGATTTCGAGGTTACCCCCGAGAAGCTGGACG
AATTAACTGCTTACTTCATCGAACAAATGGAAAAAGGTCTAGCTCCACCA
AAGGAAGGCCACACATTGGCCTCGGACAAAGGTCTTCCTATGATTCCGGC
GTTCGTCACCGGGTCACCCAACGGGACGGAGCGCGGTGTTTTACTAGCCG
CCGACCTGGGTGGTACCAATTTCCGTATATGTTCTGTTAACTTGCATGGA
GATCATACTTTCTCCATGGAGCAAATGAAGTCCAAGATTCCCGATGATTT
GCTAGACGATGAGAACGTCACATCTGACGACTGTTTGGGTTTCTAG AC
GTCGTACACTGGCCTTTATGAAGAAGTATCACCCGGACGAGTTGGCCAAG
GGTAAAGACGCCAAGCCCATGAAACTGGGGTTCACTTTCTCATACCCTGT
AGACCAGACCTCTCTAAACTCCGGACATTGATCCGTTGGACCAAGGGTT
TCCGCATCGCGGACACCGTCGGAAAGGATGTCGTGCAATTGTACCAGGAG
CAATTAAGCGCTCAGGGTATGCCTATGATCAAGGTTGTTGCATTAACCAA
CGACACCGTCGGAACGTACCTATCGCATTGCTACACGTCCGATAACACGG
ACTCAATGACGTCCGGAGAAATCTCGGACCGGTCATCGGATGTATTTTTC
GGTACCGGTACCAATGGGTGCTATATGGAGGAGATCAACAAGATCACGAA
GTTGCCACAGGAGTTGCGTGACAAGTTGATAAAGGAGGGTAAGACACACAA
TGATCATCAATGTCGAATGGGGGTCCTTCGATAATGAGCTCAAGCACTTG
CCTACTACTAAGTATGACGTCGTAATTGACCAGAAACTGTCAACGAACCC
GGGATTTCACTTGTTTGAAAAACGTGTCTCAGGGATGTTCTTGGGTGAGG
TGTTGCGTAACATTTTAGTGGACTTGCACTCGCAAGGCTTGCTTTTGCAA
CAGTACAGGTCCAAGGAACAACTTCCTGCCACTTGACTACACCTTTCCA
GTTGTCATCCGAAGTGCTGTCGCATATTGAAATTGACGACTCGACAGGTC
```

| Sequences |
|---|
| TACGTGAAACAGAGTTGTCATTATTACAGAGTCTCAGACTGCCCACCACT<br>CCAACAGAGCGTGTTCAAATTCAAAAATTGGTGCGCGCGATTTCTAGGAG<br>ATCTGCGTATTTAGCCGCCGTGCCGCTTGCCGCGATATTGATCAAGACAA<br>ATGCTTTGAACAAGAGATATCATGGTGAAGTCGAGATCGGTTGTGATGGT<br>TCCGTTGTGGAATACTACCCCGGTTTCAGATCTATGCTGAGACACGCCTT<br>AGCCTTGTCACCCTTGGGTGCCGAGGGTGAGAGGAAGGTGCACTTGAAGA<br>TTGCCAAGGATGGTTCCGGAGTGGGTGCCGCCTTGTGTGCGCTTGTAGCA<br>TGA |

Mutant GLK1                                    SEQ ID NO: 73
ATGTCATTCGACGACTTACACAAAGCCACTGAGAGAGCGGTCATCCAGGC
CGTGGACCAGATCTGCGACGATTTCGAGGTTACCCCCGAGAAGCTGGACG
AATTAACTGCTTACTTCATCGAACAAATGGAAAAAGGTCTAGCTCCACCA
AAGGAAGGCCACACATTGGCCTCGGACAAAGGTCTTCCTATGATTCCGGC
GTTCGTCACCGGGTCACCCAACGGGACGGAGCGCGGTGTTTTACTAGCCG
CCGACCTGGGTGGTGCCAATTTCCGTATATGTTCTGTTAACTTGCATGGA
GATCATACTTTCTCCATGGAGCAAATGAAGTCCAAGATTCCCGATGATTT
GCTAGACGATGAGAACGTCACATCTGACGACCTGTTTGGGTTTCTAGCAC
GTCGTACACTGGCCTTTATGAAGAAGTATCACCCGGACGAGTTGGCCAAG
GGTAAAGACGCCAAGCCCATGAAACTGGGGTTCACTTTCTCATACCCTGT
AGACCAGACCTCTCTAAACTCCGGGACATTGATCCGTTGGACCAAGGGTT
TCCGCATCGCGGACACCGTCGGAAGGATGTCGTGCAATTGTACCAGGAG
CAATTAAGCGCTCAGGGTATGCCTATGATCAAGGTTGTTGCATTAACCAA
CGACACCGTCGGAACGTACCTATCGCATTGCTACACGTCCGATAACACGG
ACTCAATGACGTCCGGAGAAATCTCGGAGCCGGTCATCGGATGTATTTTC
GGTACCGGTACCAATGGGTGCTATATGGAGGAGATCAACAAGATCACGAA
GTTGCCACAGGAGTTGCGTGACAAGTTGATAAAGGAGGGTAAGACACACA
TGATCATCAATGTCGAATGGGGGTCCTTCGATAATGAGCTCAAGCACTTG
CCTACTACTAAGTATGACGTCGTAATTGACCAGAAACTGTCAACGAACCC
GGGATTTCACTTGTTTGAAAAACGTGTCTCAGGGATGTTCTTGGGTGAGG
TGTTGCGTAACATTTTAGTGGACTTGCACTCGCAAGGCTTGCTTTTGCAA
CAGTACAGGTCCAAGGAACAACTTCCTCGCCACTTGACTACACCTTTCA
GTTGTCATCCGAAGTGCTGTCGCATATTGAAATTGACGACTCGACAGGTC
TACGTGAAACAGAGTTGTCATTATTACAGAGTCTCAGACTGCCCACCACT
CCAACAGAGCGTGTTCAAATTCAAAAATTGGTGCGCGCGATTTCTAGGAG
ATCTGCGTATTTAGCCGCCGTGCCGCTTGCCGCGATATTGATCAAGACAA
ATGCTTTGAACAAGAGATATCATGGTGAAGTCGAGATCGGTTGTGATGGT
TCCGTTGTGGAATACTACCCCGGTTTCAGATCTATGCTGAGACACGCCTT
AGCCTTGTCACCCTTGGGTGCCGAGGGTGAGAGGAAGGTGCACTTGAAGA
TTGCCAAGGATGGTTCCGGAGTGGGTGCCGCCTTGTGTGCGCTTGTAGCA
TGA Wild-type HXK1                                 SEQ ID NO: 74
MVHLGPKKPQARKGSMADVPKELMDEIHQLEDMFTVDSETLRKVVKHFID
ELNKGLTKKGGNIPMIPGVVVMEFPTGKESGNYLAIDLGGTNLRVVLVKL
SGNHTFDTTQSKYKLPHDMRTTKHQEELWSFIADSLKDFMVEQELLNTKD
TLPLGFTFSYPASQNKINEGILQRVVTKGFDIPNVEGHDVVPLLQNEISK
RELPIEIVALINDTVGTLIASYYTDPETKMGVIFGTGVNGAFYDVVSDIE
KLEGKLADDIPSNSPMAINCEYGSFDNEHLVLPRTKYDVAVDEQSPRPGQ
QAFEKMTSGYYLGELLRLVLLELNEKGLMLKDQDLSKLKQPYIMDTSYPA
RIEDDPFENLEDTDDIFQKDFGVKTTLPERKLIRRLCELIGTRAARLAVC
GIAAICQKRGYKTGHIAADGSVYNKYPGFKEAAAKGLRDIYGVVTGDASK
DPITIVPAEDGSGAGAAVIAALSEKRIAEGKSLGIIGA Mutant HXK1                                    SEQ ID NO: 75
MVHLGPKKPQARKGSMADVPKELMDEIHQLEDMFTVDSETLRKVVKHFID
ELNKGLTKKGGNIPMIPGVVVMEFPTGKESGNYLAIDLGGTNLRVVLVKL
SGNHTFDTTQSKYKLPHDMRTTKHQEELWSFIADSLKDFMVEQELLNTKD
TLPLGFTFSYPASQNKINEGILQRVVTKGFDIPNVEGHDVVPLLQNEISK
RELPIEIVALINDTVGTLIASYYTDPETKMGVIFGTGVNGAFYDVVSDIE
KLEGKLADDIPSNSPMAINCEYGSFDNEHLVLPRTKYDVAVDEQSPRPGQ
QAFEKMTPGYYLGELLRLVLLELNEKGLMLKDQDLSKLKQPYIMDTSYPA
RIEDDPFENLEDTDDIFQKDFGVKTTLPERKLIRRLCELIGTRAARLAVC
GIAAICQKRGYKTGHIAADGSVYNKYPGFKEAAAKGLRDIYGVVTGDASK
DPITIVPAEDGSGAGAAVIAALSEKRIAEGKSLGIIGA Wild-type HXK2                                 SEQ ID NO: 76
MVHLGPKKPQARKGSMADVPKELMQQIENFEKIFTVPTETLQAVTKHFIS
ELEKGLSKKGGNIPMIPGVVVMDFPTGKESGDFLAIDLGGTNLRVVLVKL
GGDRTFDTTQSKYRLPDAMRTTQNPDELWEFIADSLKAFIDEQFPQGISE
PIPLGFTFSFPASQNKINEGILQRVVTKGFDIPNIENHDVVPMLQKQITK
RNIPIEVVALINDTTGTLVASYYTDPETKMGVIFGTGVNGAYYDVCSDIE
KLQGKLSDDIPPSAPMAINCEYGSFDNEHVVLPRTKYDITIDEESPRPGQ
QTFEKMSSGYYLGEILRLALMDMYKQGFIFKNQDLSKFDKPFVMDTSYPA
RIEEDPFENLEDTDDLFQNEFGINTTVQERKLIRRLSELIGARAARLSVC
GIAAICQKRGYKTGHIAADGSVYNRYPGFKEKAANALKDIYGVVTQTSLD
DYPIKIVPAEDGSGAGAAVIAALAQKRIAEGKSVGIIGA Mutant HXK2                                    SEQ ID NO: 77
MVHLGPKKPQARKGSMADVPKELMQQIENFEKIFTVPTETLQAVTKHFIS
ELEKGLSKKGGNIPMIPGVVVMDFPTGKESGDFLAIDLGGTNLRVVLVKL
GGDRTFDTTQSKYRLPDAMRTTQNPDELWEFIADSLKAFIDEQFPQGISE
PIPLGFTFSFPASQNKINEGILQRVVTKGFDIPNIENHDVVPMLQKQITK
RNIPIEVVALINDTTGTLVASYYTDPETKMGVIFGTGVNGAYYDVCSDIE
KLQGKLSDDIPPSAPMAINCEYGSFDNEHVVLPRTKYDITIDEESPRPGQ
QTFEKMSSGYYLGEILRLALMDMYKQGFIFKNQDLSKFDKPFVMDTSYPA
RIEEDPFENLEDTDDLFQNEFGINTTVQERKLIRRLSELIGARAARLSVC
GIAAICQKRGYKTGHIAADGSVYNRYPGFKEKAANALKDIYGVVTQTSLD
DYPIKIVLLKMVPVLVPLLLLLWPKKELLKVSPLVSSVLKLNL Wild-type GLK1                                 SEQ ID NO: 78
MSFDDLHKATERAVIQAVDQICDDFEVTPEKLDELTAYFIEQMEKGLAPP
KEGHTLASDKGLPMIPAFVTGSPNGTERGVLLAADLGGTNFRICSVNLHG
DHTFSMEQMKSKIPDDLLDDENVTSDDLFGFLARRTLAFMKKYHPDELAK
GKDAKPMKLGFTFSYPVDQTSLNSGTLIRVVTKGFRIADTVGKDVVQLYQ
EQLSAQGMPMIKVVALTNDTVGTYLSHCYTSDNTDSMTSGEISEPVIGCI
FGTGTGNGCYMEEINKITKLPQELRDKLIKEGKTHMIINVEWGSFDNELKH
LPTTKYDVVIDQKLSTNPGFHLFEKRVSGMFLGEVLRNILVDLHSQGLLL
QQYRSKEQLPRHLTTPFQLSSEVLSHIEIDDSTGLRETELSLLQSLRLPT
TPTERVQIQKLVRAISRRSAYLAAVPLAAILIKTNALNKRYHGEVEIGCD
GSVVEYYPGFRSMLRHALALSPLGAEGERKVHLKIAKDGSGVGAALCALV
A Mutant GLK1                                    SEQ ID NO: 79
MSFDDLHKATERAVIQAVDQICDDFEVTPEKLDELTAYFIEQMEKGLAPP
KEGHTLASDKGLPMIPAFVTGSPNGTERGVLLAADLGGANFRICSVNLHG
DHTFSMEQMKSKIPDDLLDDENVTSDDLFGFLARRTLAFMKKYHPDELAK
GKDAKPMKLGFTFSYPVDQTSLNSGTLIRWTKGFRIADTVGKDVVQLYQE
QLSAQGMPMIKVVALTNDTVGTYLSHCYTSDNTDSMTSGEISEPVIGCIF
GTGTNGCYMEEINKITKLPQELRDKLIKEGKTHMIINVEWGSFDNELKH
PTTKYDVVIDQKLSTNPGFHLFEKRVSGMFLGEVLRNILVDLHSQGLLLQ
QYRSKEQLPRHLTTPFQLSSEVLSHIEIDDSTGLRETELSLLQSLRLPTT
PTERVQIQKLVRAISRRSAYLAAVPLAAILIKTNALNKRYHGEVEIGCDG
SVVEYYPGFRSMLRHALALSPLGAEGERKVHLKIAKDGSGVGAALCALVA The embodiments illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the embodiments claimed. Thus, it should be understood that although the present description has been specifically disclosed by embodiments, optional features, modification and variation of the concepts herein disclosed may be resorted to by those skilled in the art, and that such modifications and variations are considered to be within the scope of these embodiments as defined by the description and the appended claims.

Embodiments of the methods comprising the above-mentioned features are intended to fall within the scope of the disclosure.

While the present embodiments are susceptible to various modifications and alternative forms, exemplary embodiments thereof are shown by way of example in the drawings and are herein described in detail. It should be understood, however, that the description of exemplary embodiments is not intended to limit the examples to the particular forms disclosed, but on the contrary, the intention is to cover all modifications, equivalents and alternatives as defined by the embodiments above and the claims below.

The transgenic microorganisms will be described more fully hereinafter with reference to the accompanying drawings, in which some, but not all embodiments are shown. Indeed, the methods and compositions may be embodied in many different forms and should not be construed as limited to the embodiments set forth herein; rather, these embodiments are provided so that this disclosure will satisfy applicable legal requirements.

Likewise, many modifications and other embodiments of the transgenic microorganisms and methods described herein will come to mind to one of skill in the art to which the methods and compositions pertain having the benefit of the teachings presented in the foregoing descriptions and the associated drawings. Therefore, it is to be understood that the methods and compositions described herein are not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the methods and compositions pertain.

EXAMPLES

Example 1. Evolution and Characterization of a Glucose and Xylose Co-Fermenting Mutant Various strategies have been developed to engineer *S. cerevisiae* capable of simultaneously co-fermenting glucose and xylose (11, 19, 32). However, in all cases the rate of co-fermentation was limited by the consumption rate of xylose (32-34). As such, the introduction of a robust and efficient xylose fermentation pathway is an essential prerequisite for simultaneous co-fermentation of glucose and xylose. To this end, we started with a rapid engineered xylose-fermenting *S. cerevisiae* strain, SR8 (35). Although the xylose consumption rate of the SR8 strain was nearly 25% of the glucose consumption rate when cultured with a single sugar (FIG. 1D), culturing in a mixture of the two sugars resulted in a severely inhibited xylose fermentation rate (FIG. 1A).

In an attempt to bypass glucose repression, we evolved the SR8 strain on xylose under the presence of the glucose analogue 2-deoxyglucose (2-DG) (FIG. 1F). Because 2-DG cannot be utilized as a carbon source, this evolution selects for cells able to consume xylose in the presence of 2-DG. Initially, the cells grew poorly in a mixture of 1 g/L 2-DG and 80 g/L xylose. However, after serial sub-cultures, the evolving cultures exhibited improved growth and xylose consumption rates. Through gradually increasing the 2-DG concentration to 5 g/L and eventually 10 g/L, we increased the selection pressure which allowed the accumulation of mutants capable of growing on xylose with toxic levels of 2-DG. As a result we isolated a mutant (SR8#22) that consumed glucose and xylose simultaneously (FIG. 1B). Despite the reduced rate of simultaneous sugar utilization as compared to sequential utilization of glucose and xylose, a mixture of 40 g/L xylose and 40 g/L glucose could be simultaneously consumed within 24 hours (FIG. 1C).

Figure 5:
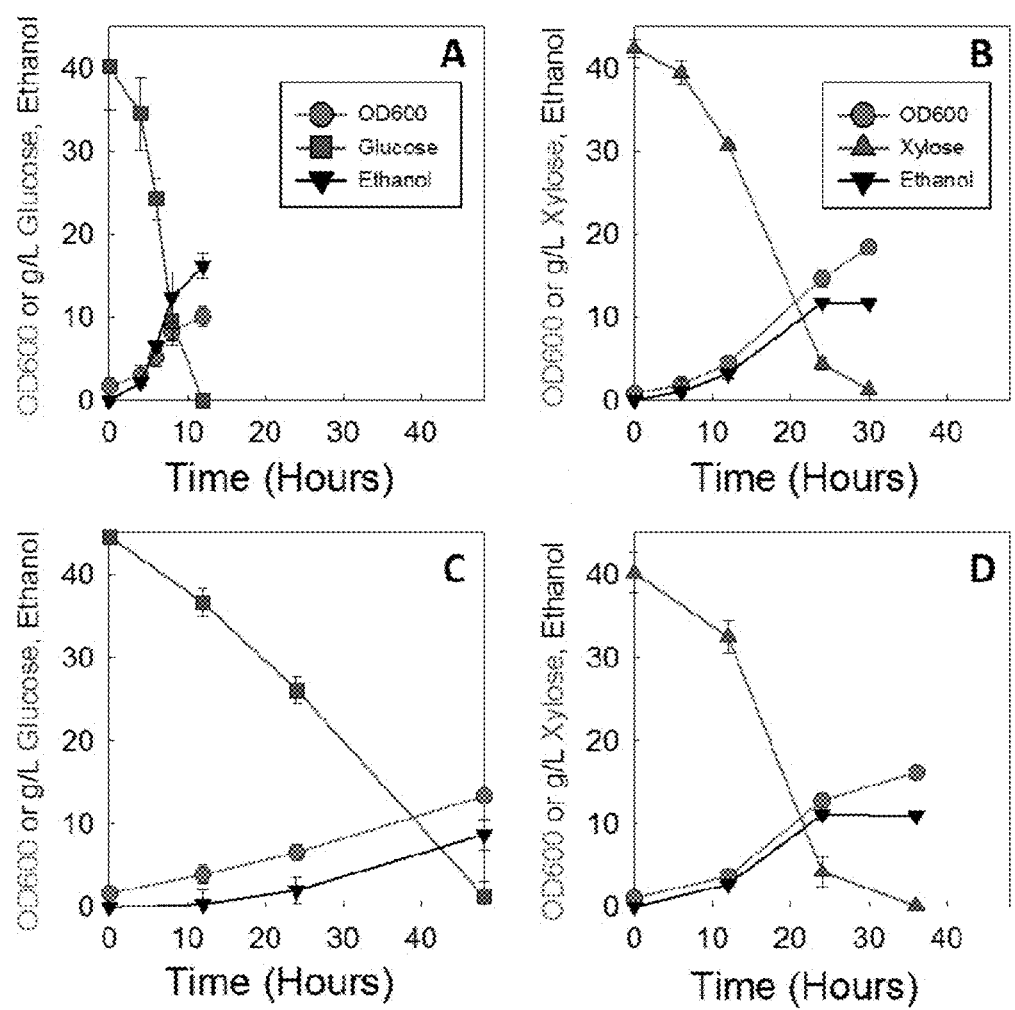
FIG. 5 panels A-D. Fermentation profiles of parent and evolved strains in pure sugars. Fermentation profiles of SR8 (A, B) and SR8#22 (C, D) cultured in YP medium with 40 g/L of pure glucose (A, C) and pure xylose (B, D). Results are the mean of duplicate experiments with standard deviations indicated by error bars. Data points are: OD (yellow circle), glucose (blue square), xylose (red triangle), and ethanol (black downward triangle).
Figure 6:
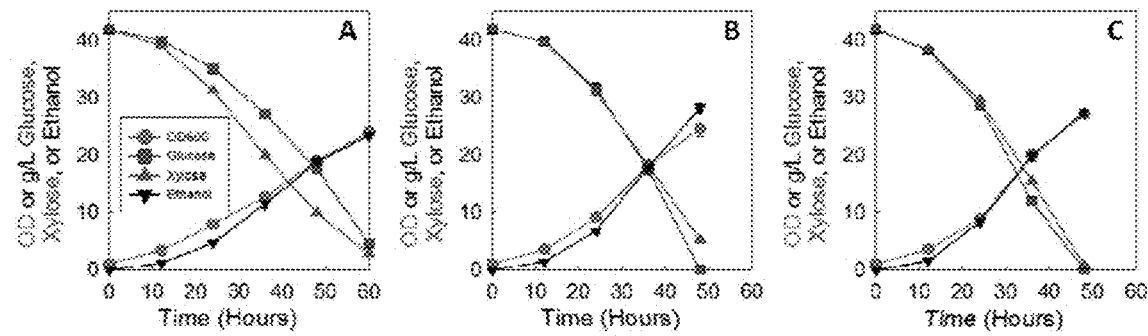
FIG. 6 panels A-C. Fermentation profiles of SR8#22 with different hexokinase/glucokinase deletions. Fermentation profile of (A) SR8#22Δmglk1, (B) SR8#22Δmhxk2 and (C) SR8#22Δmhxk1 in complex medium containing 40 g/L xylose and 40 g/L glucose under oxygen-limited conditions with initial OD 1. Results are the mean of duplicate experiments with standard deviations indicated by error bars. Data points are: OD (yellow circle), glucose (blue square), xylose (red triangle), and ethanol (black downward triangle).

To investigate the mechanisms underlying the simultaneous co-fermentation of the evolved mutant, the SR8#22 strain was cultured in glucose or xylose as a single carbon source. Interestingly, the xylose consumption rate of the SR8#22 strain was similar to the parental SR8 strain while the glucose consumption rate reduced significantly (FIGS. 1D and 5). Furthermore, genome sequencing of the SR8#22 strain revealed mutations in the three endogenous hexokinases GLK1, HXK1 and HXK2 (Table 3). Subsequent enzymatic activity assays indicated that these mutations contributed to the reduced hexokinase activity in the SR8#22 strain (FIG. 1E), which could account for the reduced glucose consumption rate of the SR8#22 strain. Therefore, we hypothesized that the three hexokinase mutations in the evolved SR8#22 strain might be responsible for the simultaneous co-fermentation phenotype.

Figure 2:
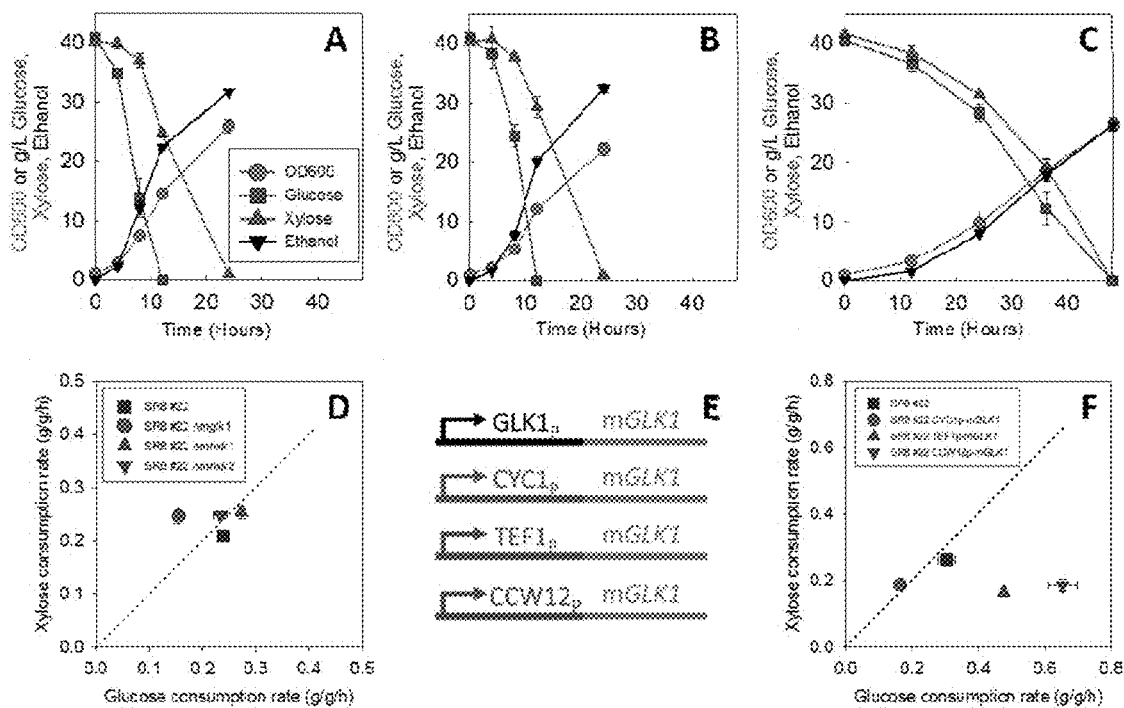
FIG. 2 panels A-F. Transferring hexokinase mutations from SR8#22 to the unevolved parent strain enables simultaneous co-fermentation. Fermentation profiles of (A) SR8mGLK1, (B) SR8mGLK1mHXK2, and (C) Re #22 (SR8mGLK1mHXK2mHXK1) in complex medium containing 40 g/L xylose and 40 g/L glucose under oxygen-limited condition with initial OD 1. (D) Specific xylose and glucose consumption rates in hexokinase or glucokinase deletion mutants of SR8#22 measured after 12 hours of growth in a mixture of glucose and xylose. (E) Diagram of promoter substation strains. Different promoters were integrated upstream of the mGLK1 gene using CRISPR genome editing. (F) Specific xylose and glucose consumption rates of mutant SR8#22 strains with modulated mGLK1 expression level measured after 12 hours of growth in a mixture of glucose and xylose.

Example 2. Reverse Engineering of the SR8#22 Strain and Determination of the Mechanism of Simultaneous Co-Fermentation To determine the necessity of all three mutations for simultaneous co-utilization of glucose and xylose, we sequentially introduced the three mutations in the GLK1, HXK1 and HXK2 genes into the parental strain SR8 using CRISPR/Cas9 genome editing (Table 3). Similar to the phenotype of the parental strain SR8, intermediate strains SR8mGLK1 and SR8mGLK1mHXK2 utilized glucose and xylose sequentially (FIGS. 2A and B). However, the full recreation of the three hexokinase mutations (the strain Re #22) led to the identical phenotype—simultaneous consumption of glucose and xylose (FIG. 2C)—of the evolved mutant SR8#22 strain (FIG. 1B). These results confirmed that the co-fermentation phenotype of the SR8#22 strain was dependent upon all three mutations.

Figure 7:
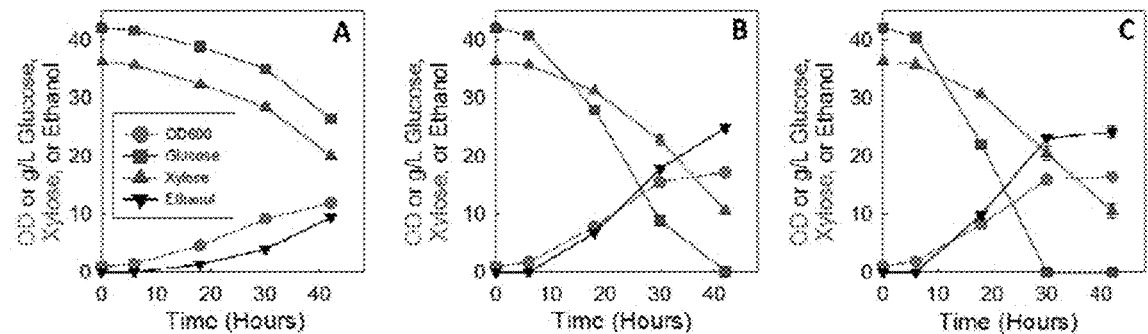
FIG. 7 panels A-C. Fermentation profiles of SR8#22 different mGLK1 expression levels. Fermentation profile of (A) #22-CYC1p-mGLK1, (B) #22-TEF1p-mGLK1, and (C) #22-CCW12p-mGLK1 in complex medium containing 40 g/L xylose and 40 g/L glucose under oxygen-limited conditions with initial OD 1. Data points are: OD (yellow circle), glucose (blue square), xylose (red triangle), and ethanol (black downward triangle).

To investigate whether the simultaneous co-fermentation phenotype of the SR8#22 strain was the result of the three specific mutations or instead a decreased overall hexokinase activity, we individually deleted mHXK1, mHXK2 and mGLK1 in SR8#22 by the Cre-Loxp system. Interestingly, the deletion of mHXK1 or mHXK2 barely influenced the simultaneous co-fermentation phenotype while the deletion of mGLK1 resulted in a significantly reduced glucose consumption rate (FIGS. 2D and 7). Thus, we reasoned that the mutant glucokinase contributed most to the overall hexokinase activity of the SR8#22 strain.

As the specific mutations on HXK1 and HXK2 were not necessary, we speculated that the reduced glucose consumption rate of the SR8#22 strain elicited the simultaneous co-fermentation. Therefore, we aimed to investigate how changing glucose consumption rates would affect the simultaneous co-fermentation phenotype. We manipulated hexokinase activity in the SR8#22 strain by using strong (CCW12p), medium (TEF1p) and weak (CYC1p) promoters to control the expression of mGLK1. The three promoters with different strengths were introduced directly upstream of the start codon of the mGLK1 gene by CRISPR/Cas9 genome editing to create mutant strains expressing mGLK1 differentially (#22-CYC1p-mGLK1, #22-TEF1p-mGLK1 and #22-CCW12p-mGLK1). Despite altered mGLK1 expression levels, which led to varied glucose consumption rates of the three strains, the xylose consumption rates remained similar (FIG. 2E and FIG. 7). This result indicated that reducing the rate of glucose consumption was sufficient to allow simultaneous co-utilization of glucose and xylose.

TABLE 1

Plasmids

| Plasmid | Description | Reference |
|---|---|---|
| pRS41N-Cas9 | A single-copy plasmid containing Cas9 and a nourseothricin marker | (51) |
| pRS42K-gRNA-GLK1$_p$ | A multi-copy plasmid containing a guide RNA for promoter substitution of mGLK1 and a geneticin marker | This study |
| pRS42K -gRNA-GLK1 | A multi-copy plasmid containing a guide RNA for GLK1 and a geneticin marker | This study |
| pRS42H -gRNA-HXK2 | A multi-copy plasmid containing a guide RNA for HXK2 and a hygromycin B marker | This study |
| pRS42K -gRNA-HXK1 | A multi-copy plasmid containing a guide RNA for HXK1 and a geneticin marker | This study |
| pRS42H -gRNA-HXT2 | A multi-copy plasmid containing a guide RNA for HXT2 and a hygromycin B marker | This study |
| pRS406-rtTA | Integrative plasmid pRS406 with pMYO2-rtTA(S2)-tCYC1 expression cassette | This study |
| pRS403 -TetO7p | Integrative plasmid pRS403 with a multicloning site between the TetO7 promoter and ADH1 terminator | This study |
| pRS403 -TetO7p-HXK1 | Integrative plasmid pRS403 with TetO7p-HXK1-ADH1t expression cassette | This study |
| pRS403 -TetO7p-HXK2 | Integrative plasmid pRS403 with TetO7p-HXK2-ADH1t expression cassette | This study |

Figure 8:
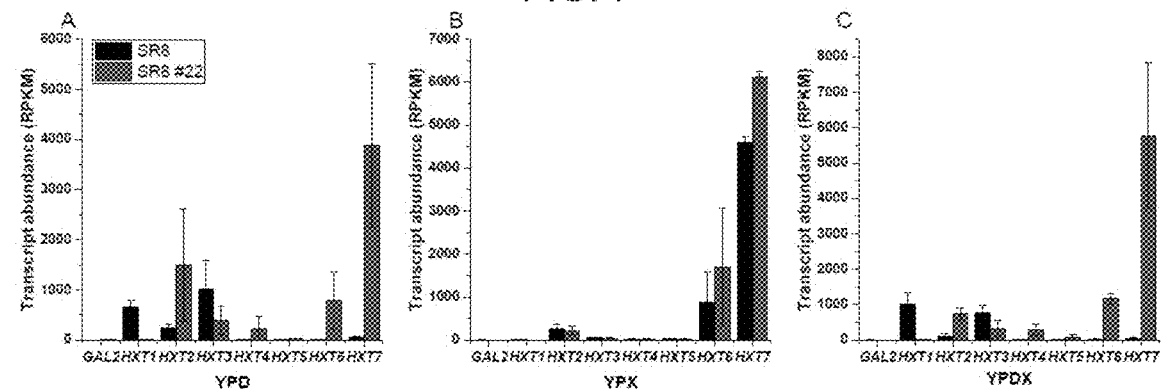
FIG. 8 panels A-C. Comparison of expressions of sugar transporters in different sugar conditions. SR8 and SR8#22 were cultured in YPD (A), YPX (B), and YPDX (C) at an initial OD of 1. Cells were grown to mid-exponential phase and RNA was extracted and quantified as described in materials and methods.
Figure 9:
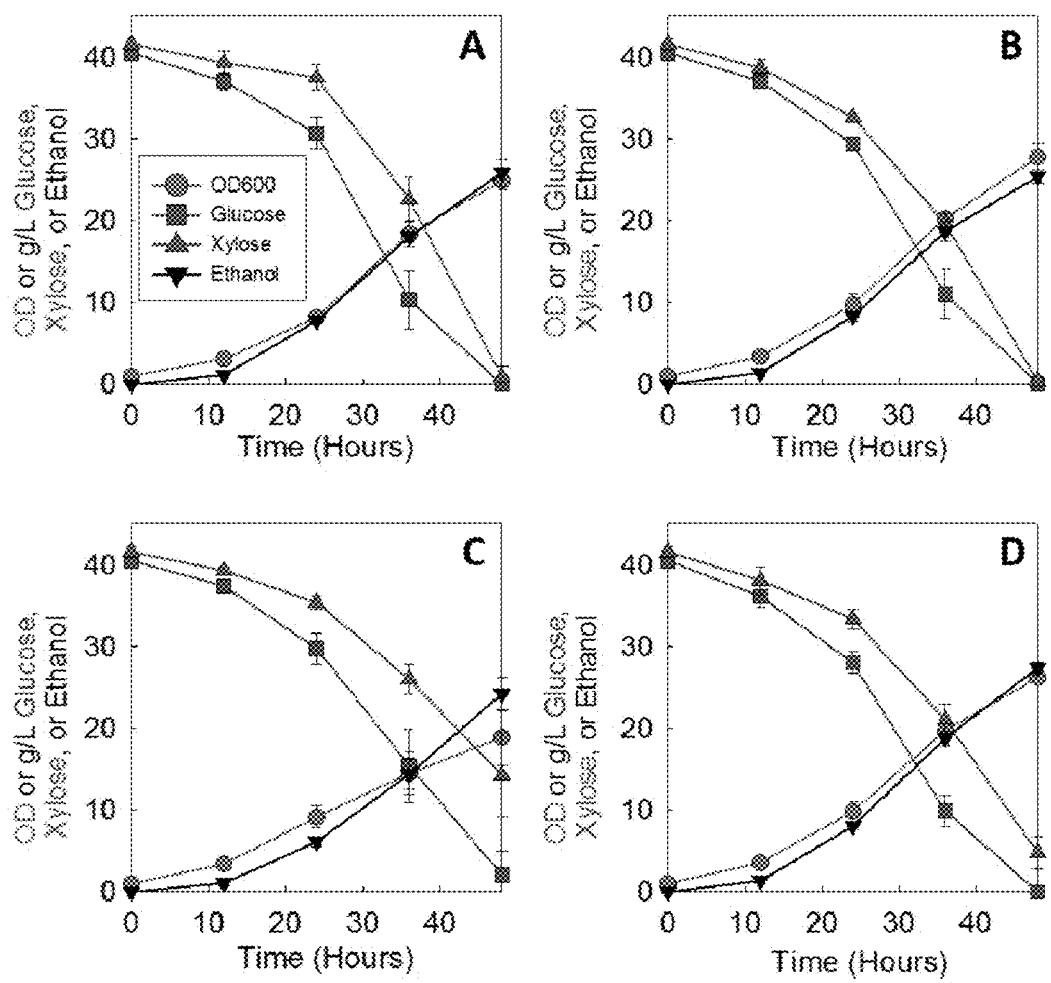
FIG. 9 panels A-D. Fermentation profiles of SR8#22 with different single transporter deletions. Fermentation profiles of (A) SR8#22Δhxt2, (B) SR8#22hxtΔ3, (C) SR8#22Δhxt4, and (D) SR8#22hxtΔ6hxtΔ7 in complex medium containing 40 g/L xylose and 40 g/L glucose under oxygen-limited conditions with initial OD 1. Results are the mean of duplicate experiments with standard deviations indicated by error bars. Data points are: OD (yellow circle), glucose (blue square), xylose (red triangle), and ethanol (black downward triangle).
Figure 10A:
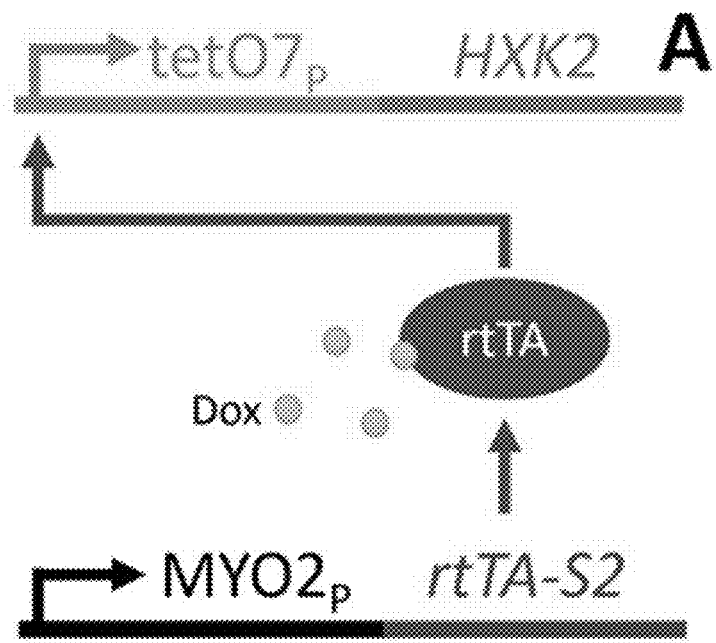
FIG. 10A-H. Controlling glucose consumption rate through the external inducer doxycycline.
Figure 10B:
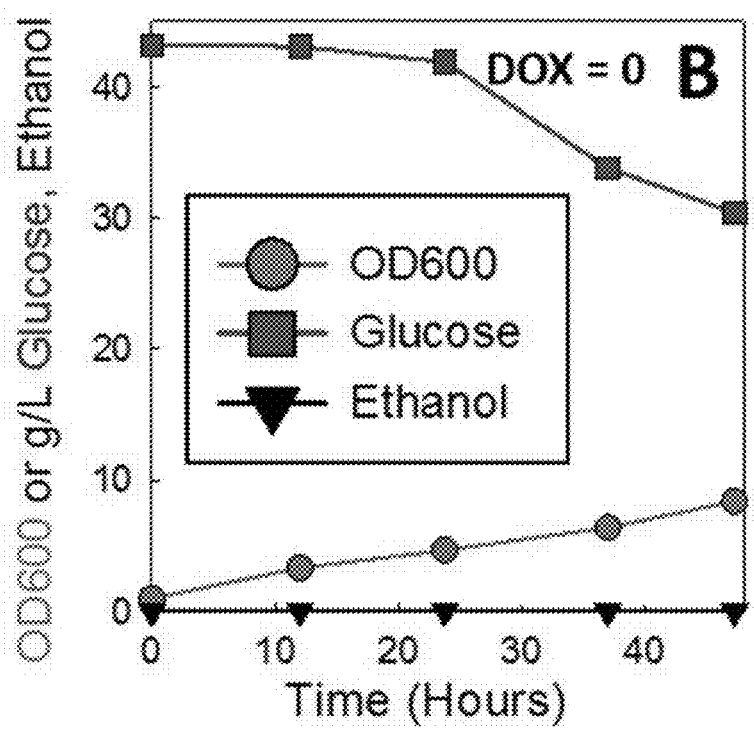
Figure 10C:
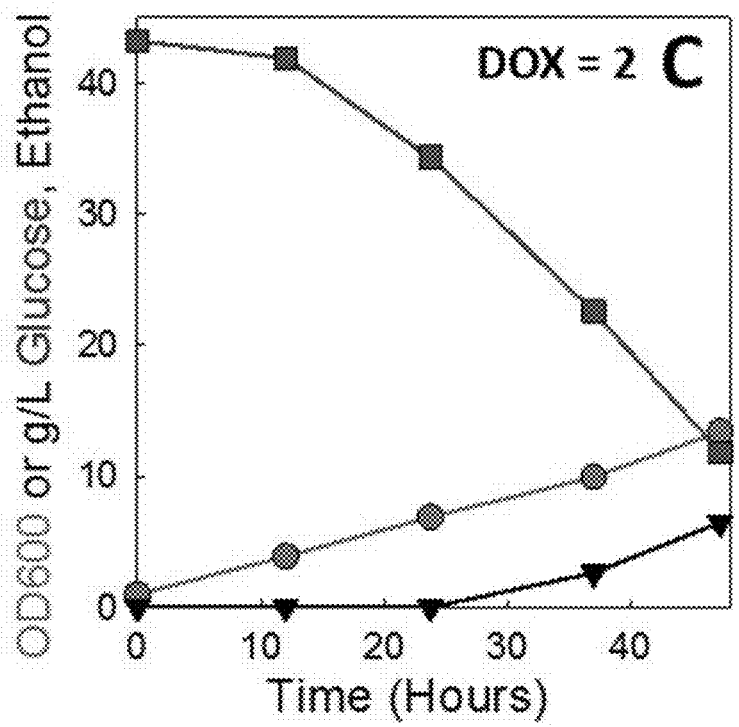
Figure 10D:
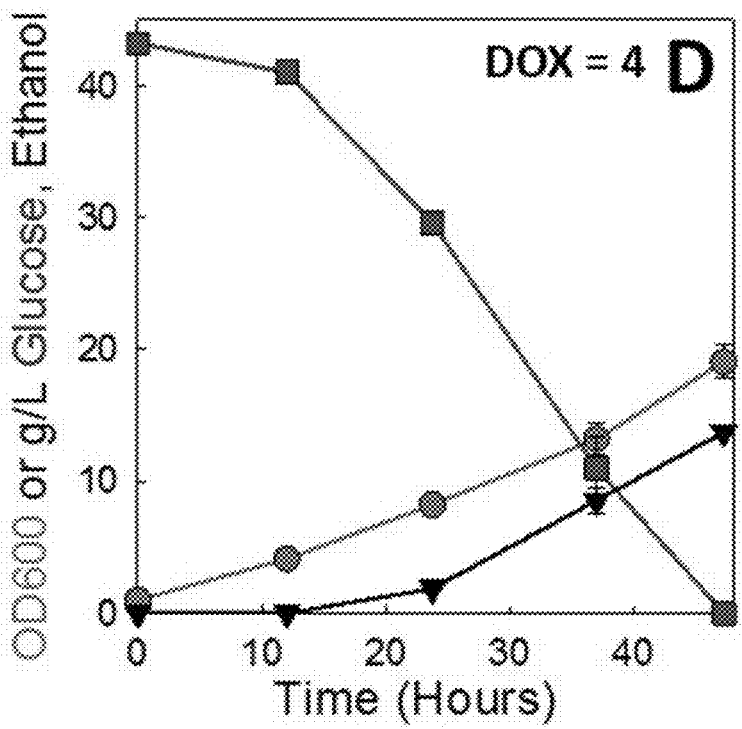
Figure 10E:
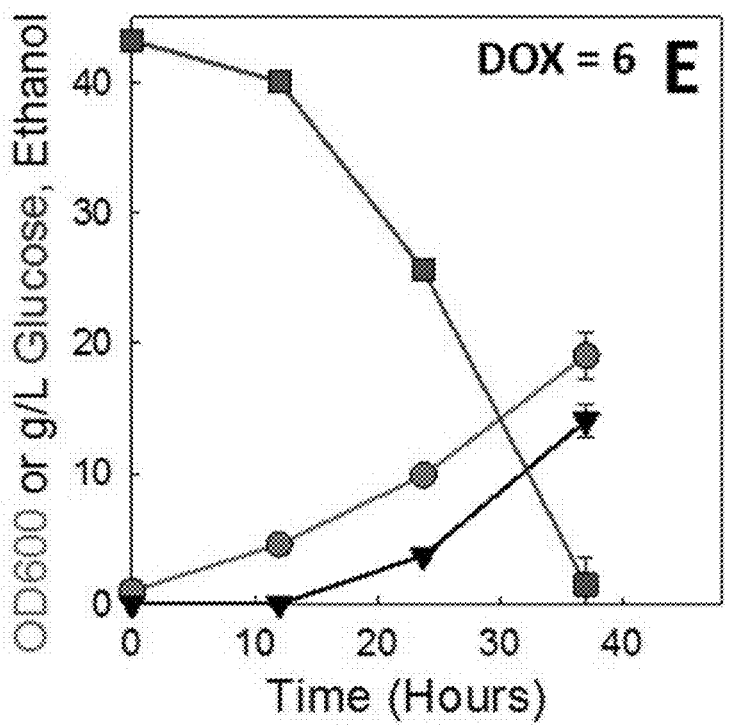
Figure 10F:
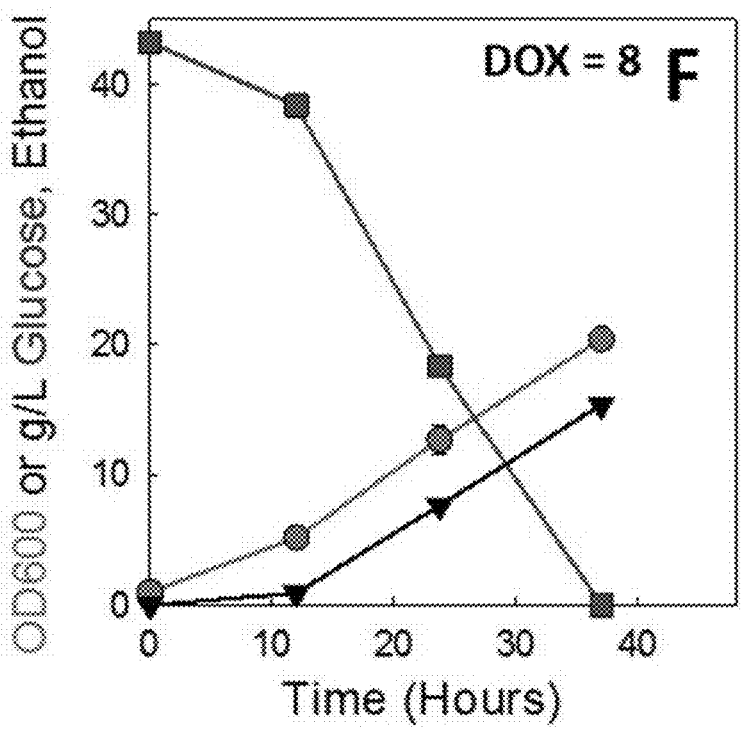
Figure 10G:
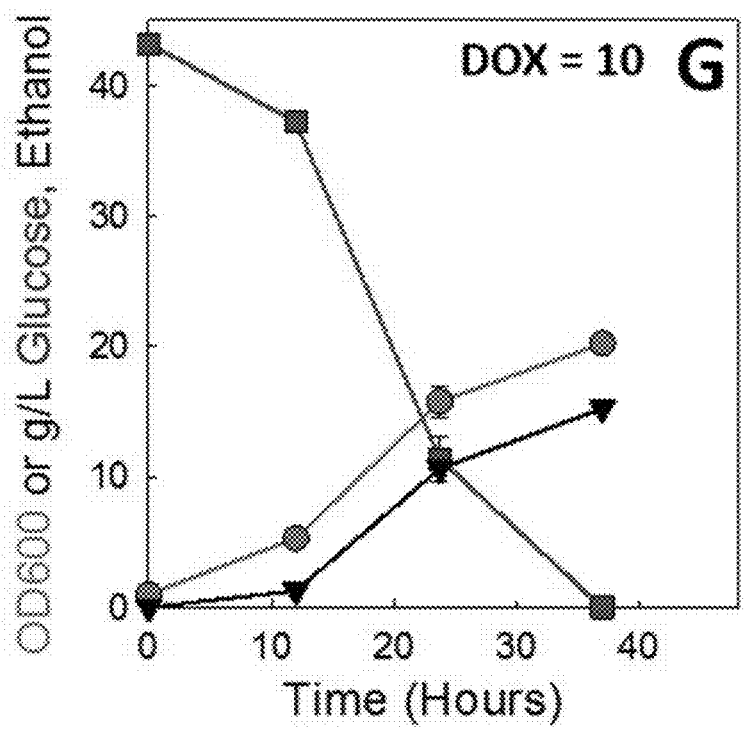
Figure 10H:
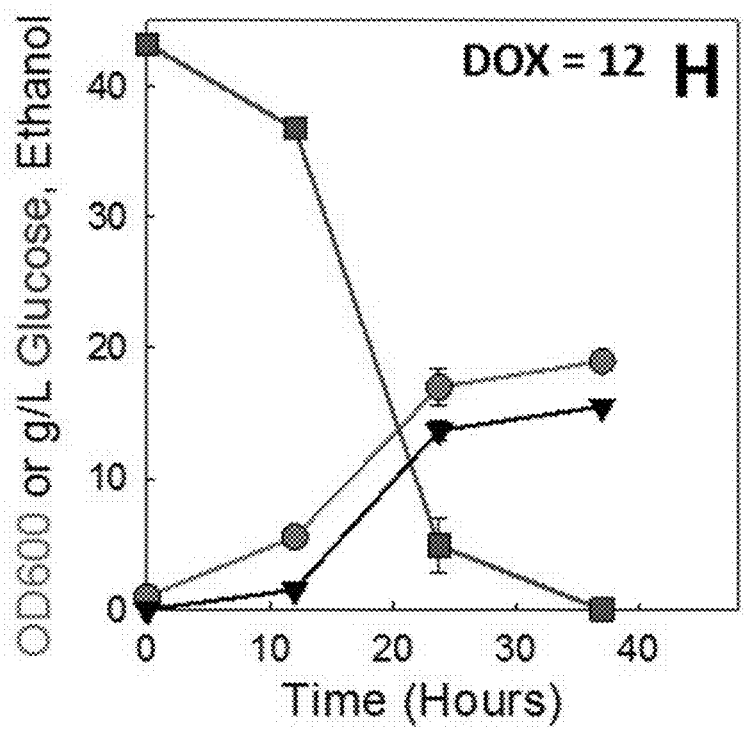
Figure 11A:
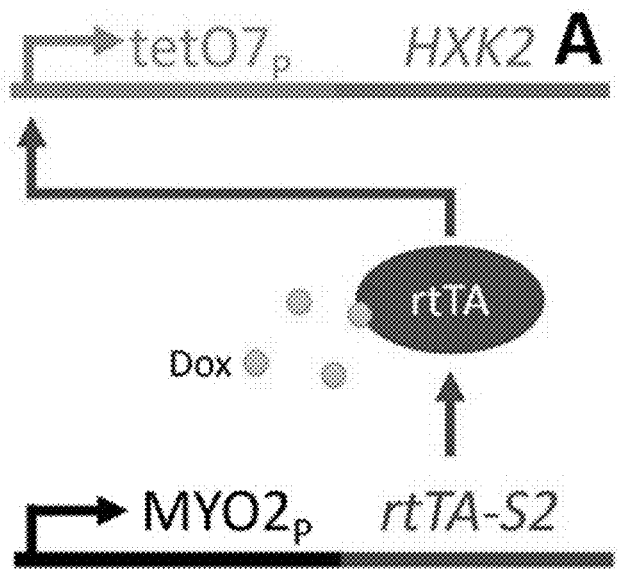
FIG. 11A-H. Co-fermentation of glucose and xylose by controlling glucose consumption rate.
Figure 11B:
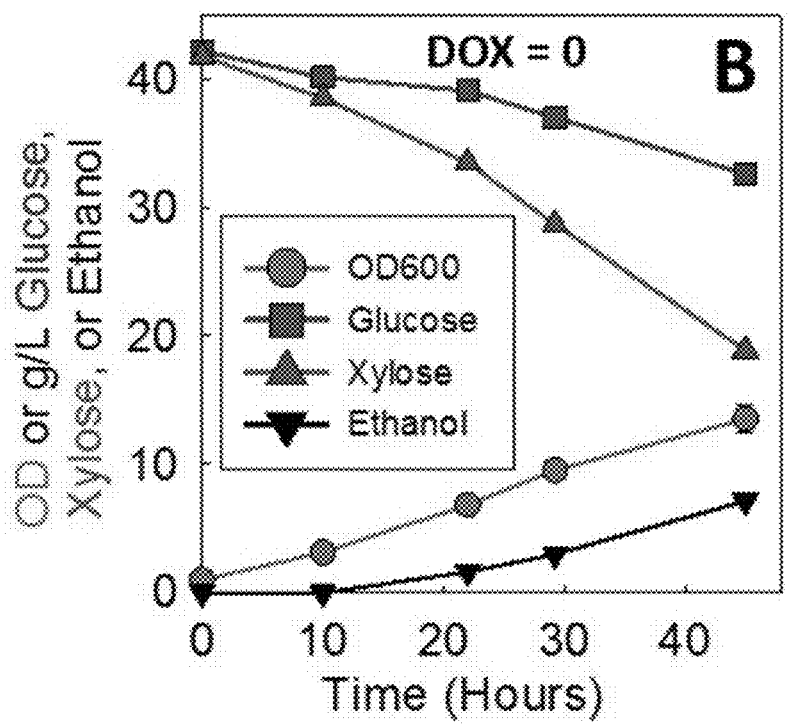
Figure 11C:
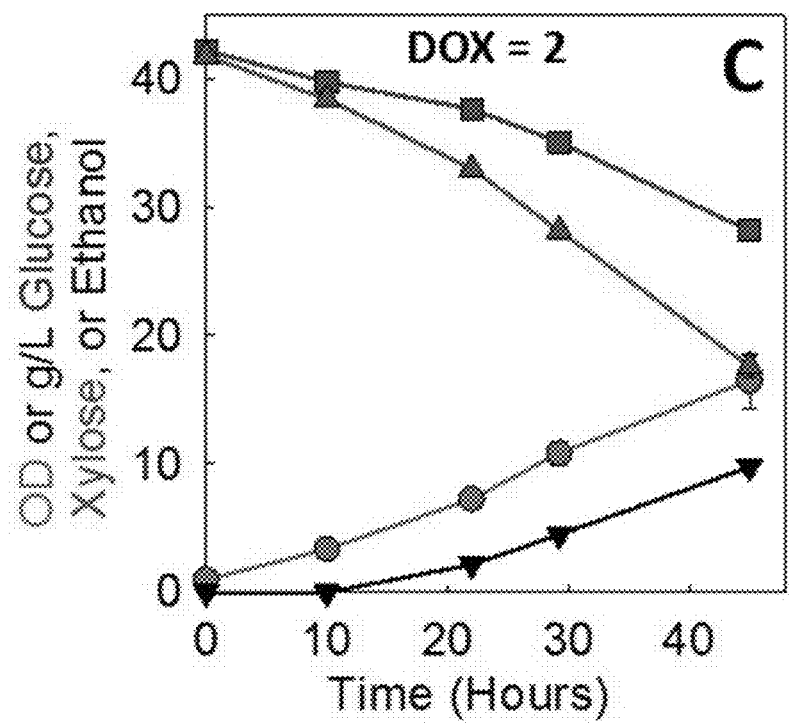
Figure 11D:
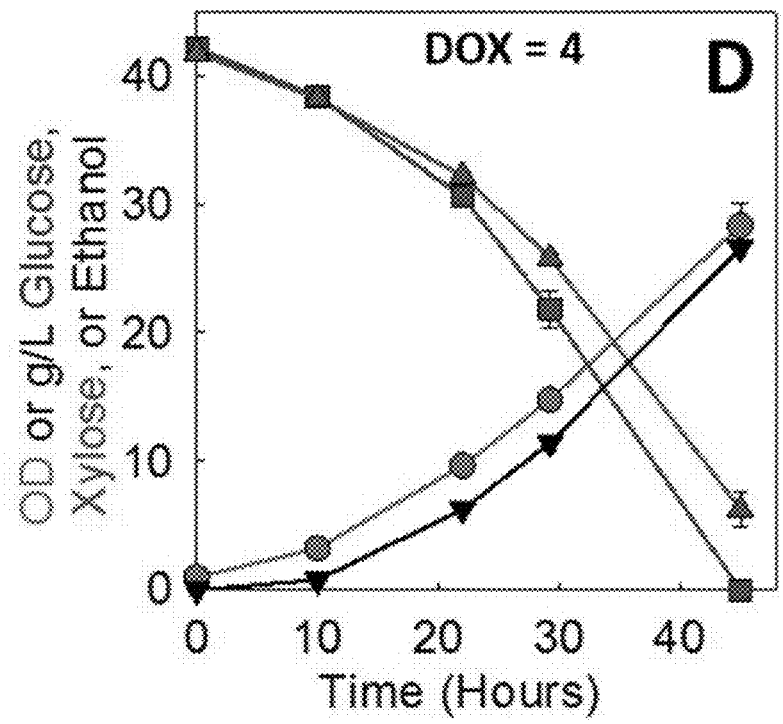
Figure 11E:
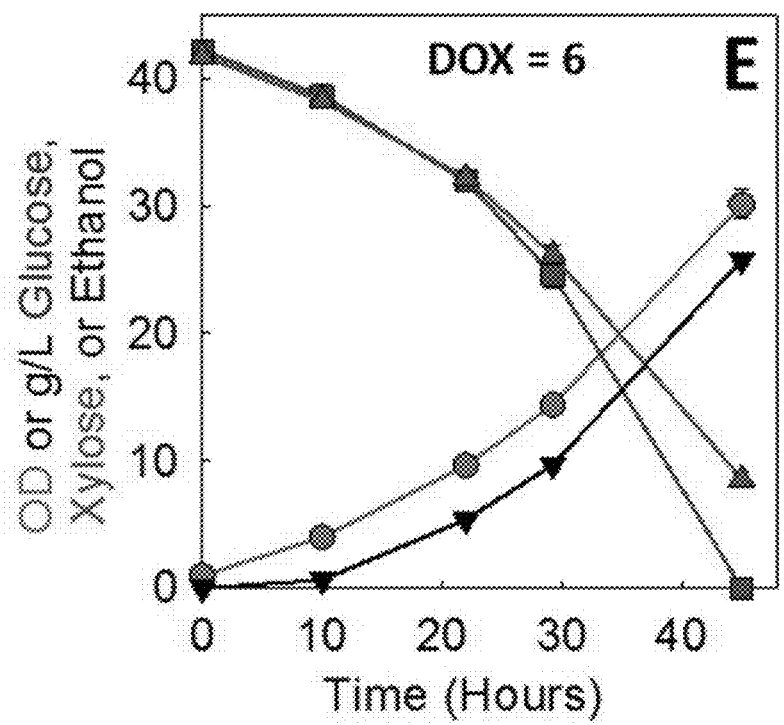
Figure 11F:
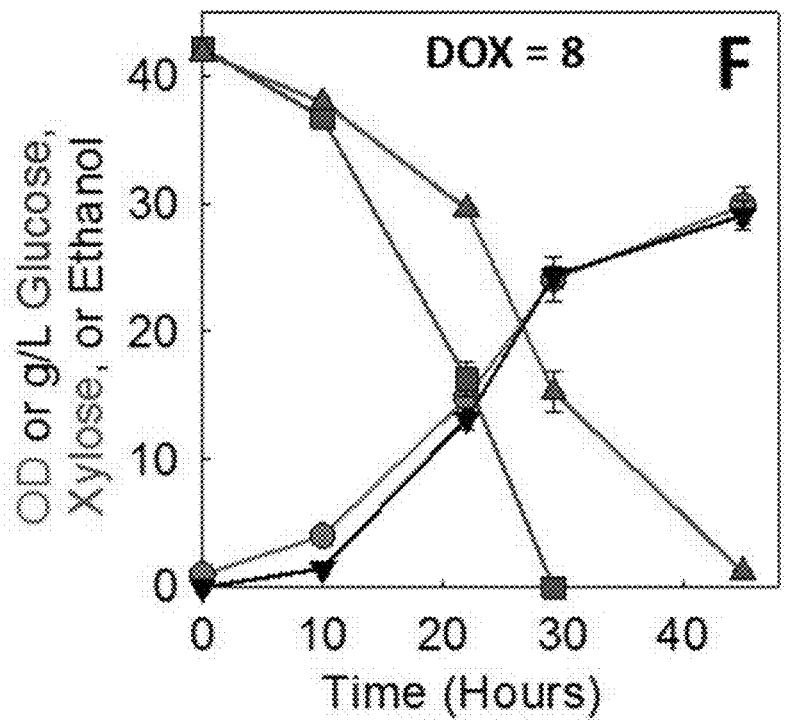
Figure 11G:
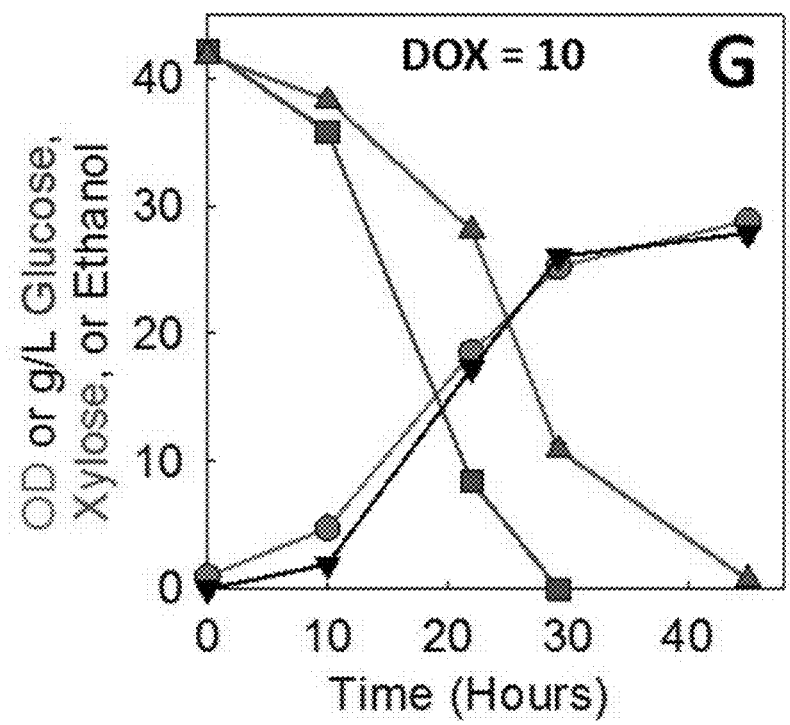
Figure 11H:
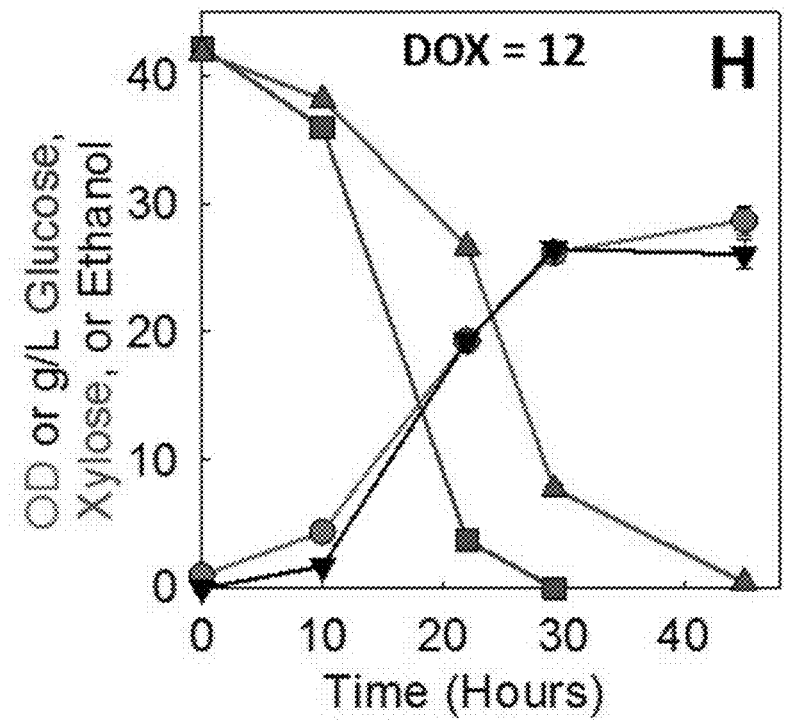
Figure 12A:
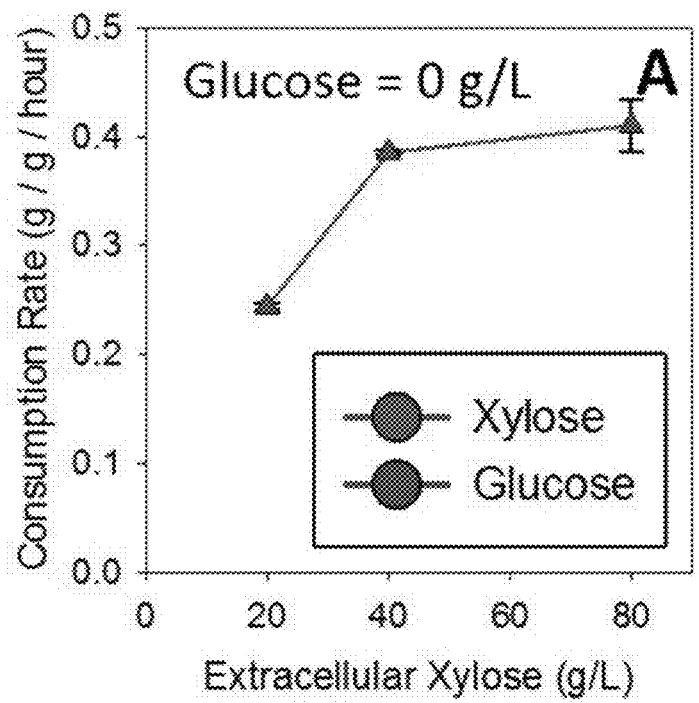
FIG. 12A-H. Sugar ratios affect simultaneous utilization capabilities at constant hexokinase induction.
Figure 12B:
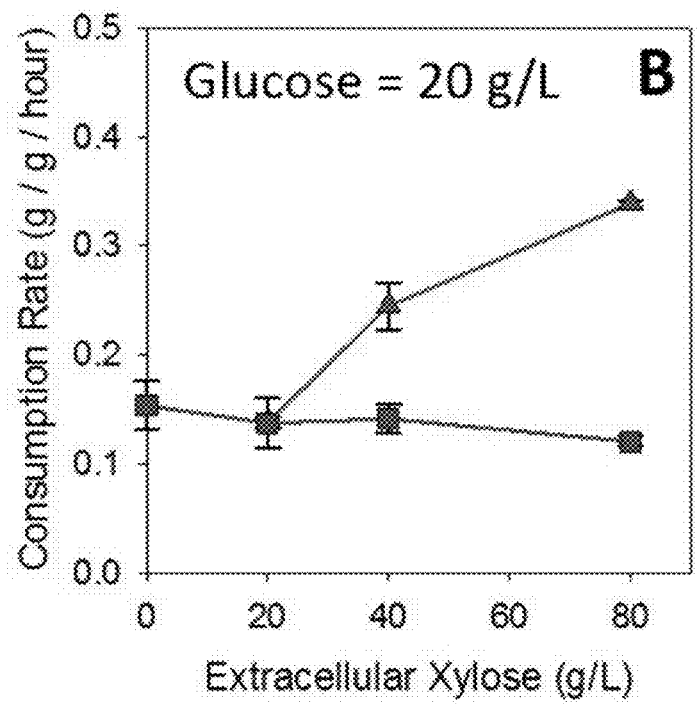
Figure 12C:
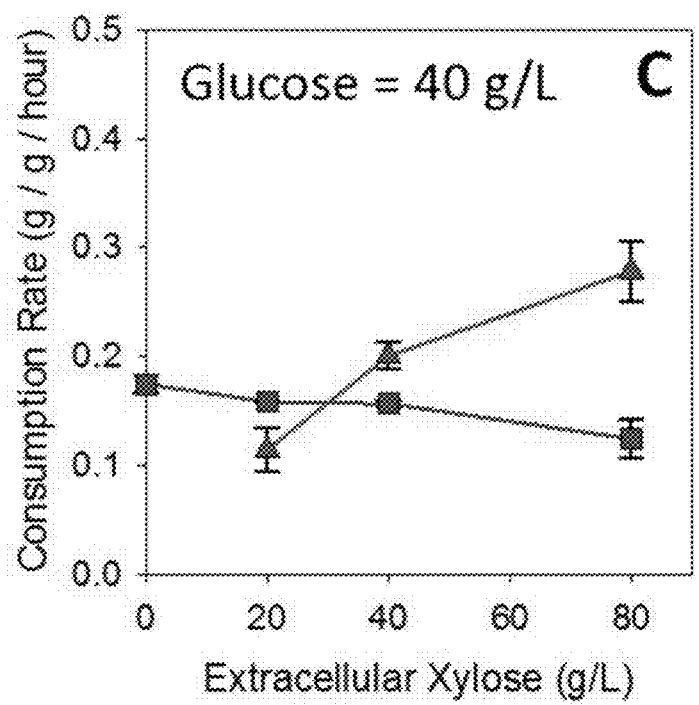
Figure 12D:
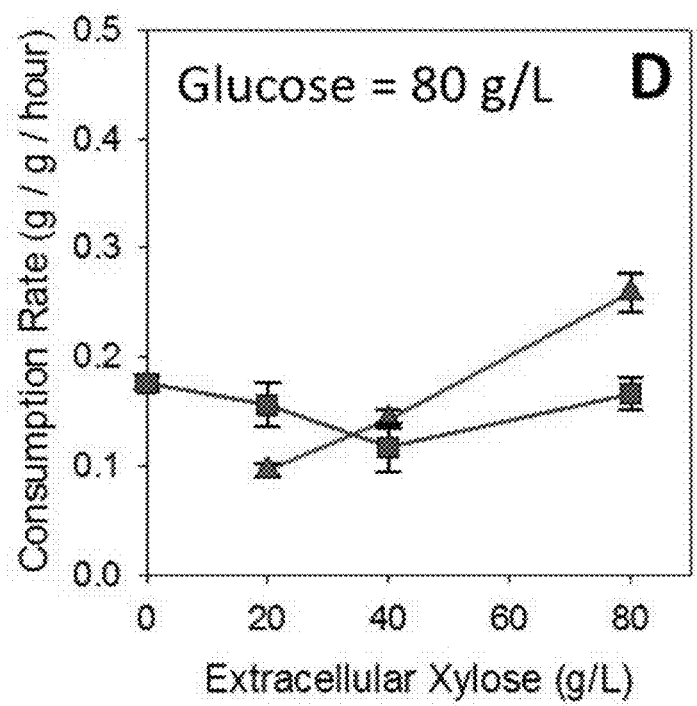
Figure 12E:
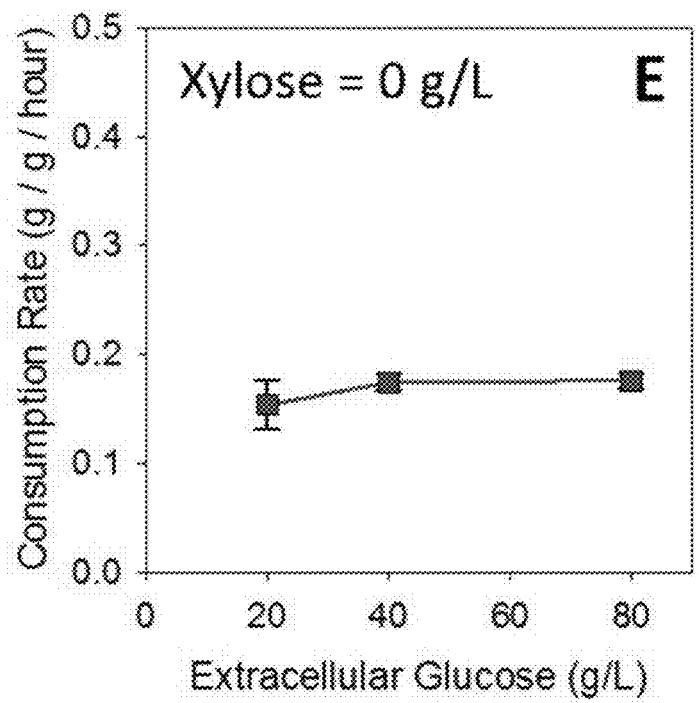
Figure 12F:
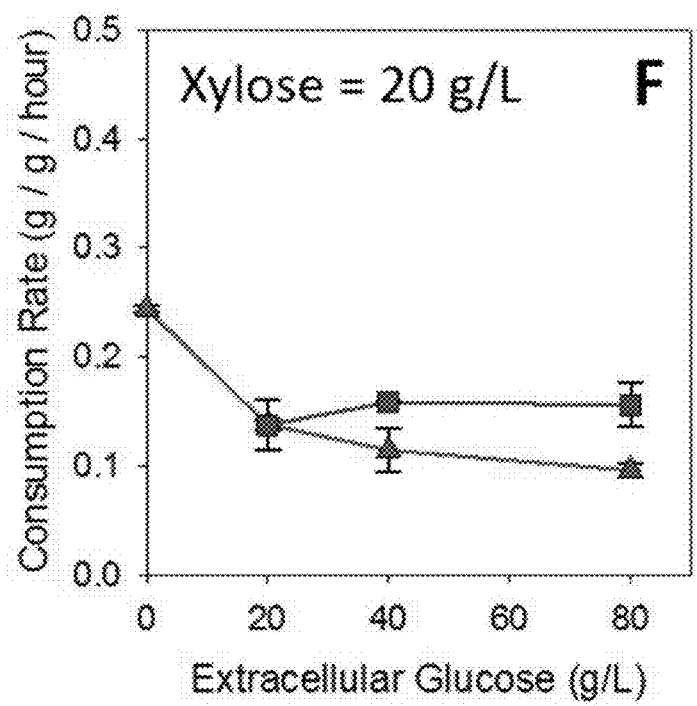
Figure 12G:
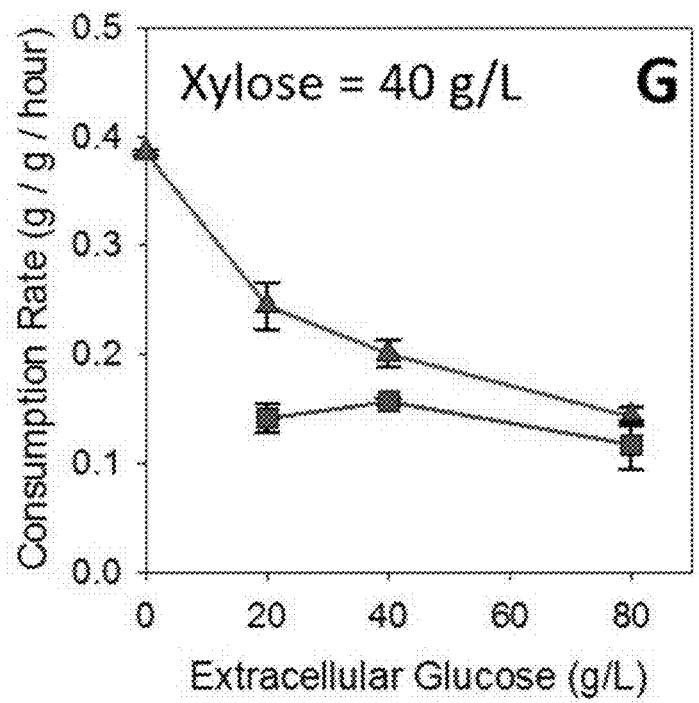
Figure 12H:
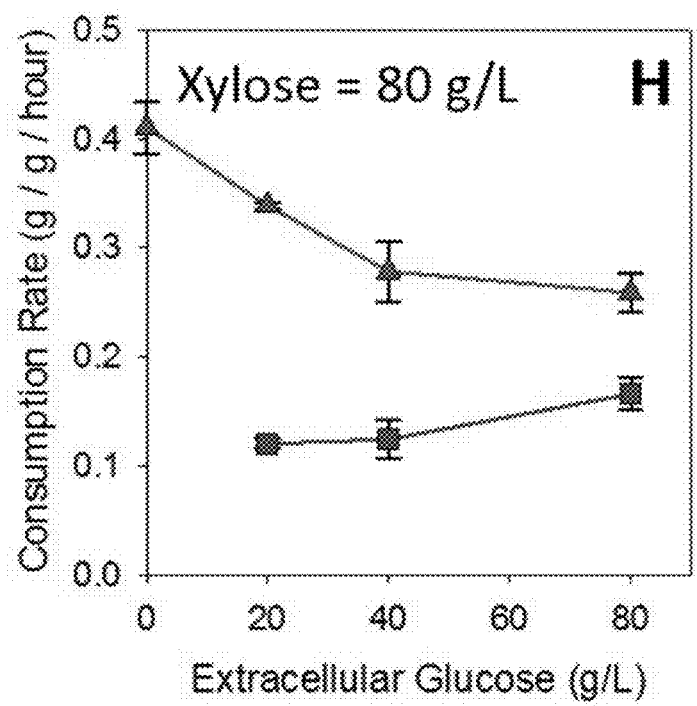
Figure 13A:
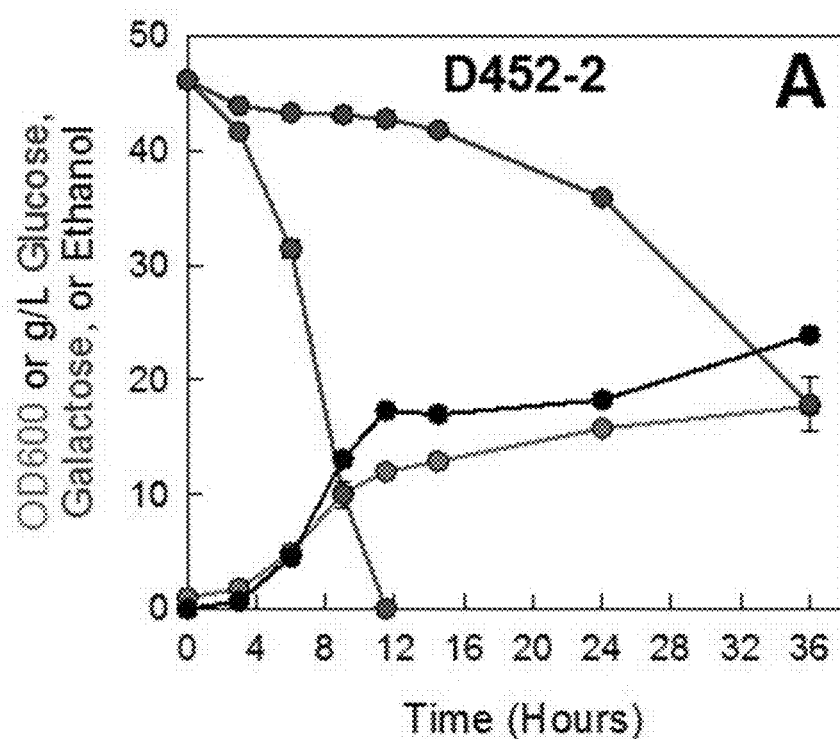
FIG. 13A-H. Modulating HXK1 expression enables simultaneous utilization of glucose and galactose. Fermentation profiles of (FIG. 13A) parent D452-2 pRS403 and (FIG. 13B-H) D452-2Δhxk$^0$ with inducible HXK1 cultured in a mixture of glucose and galactose. The inducible HXK1 strain (FIG. 13B-H) was cultured with various levels of doxycycline at (FIG. 13B) 0, (FIG. 13C) 2, (FIG. 13D) 4, (FIG. 13E) 6, (FIG. 13F) 8, (FIG. 13G) 10, and (FIG. 13H) 12 μg/mL. Fermentations were performed with 25 mL YP media in 125 mL flasks at an initial OD of 1. Data points are the result of duplicate experiments with standard deviations indicated by error bars. Data points are: OD (yellow circle), glucose (blue square), galactose (purple triangle), and ethanol (black downward triangle).
Figure 13B:
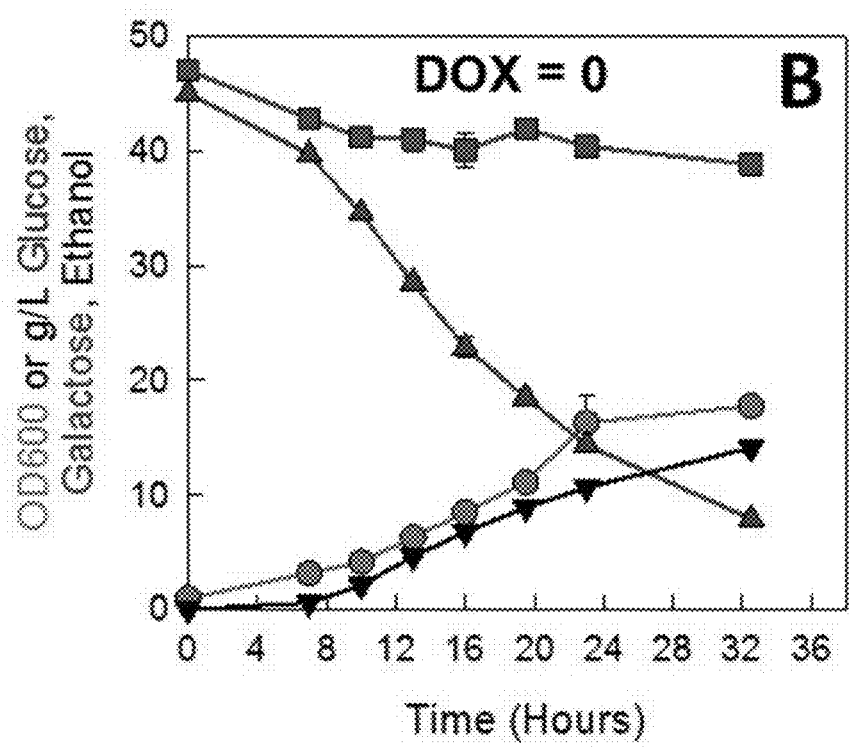
Figure 13C:
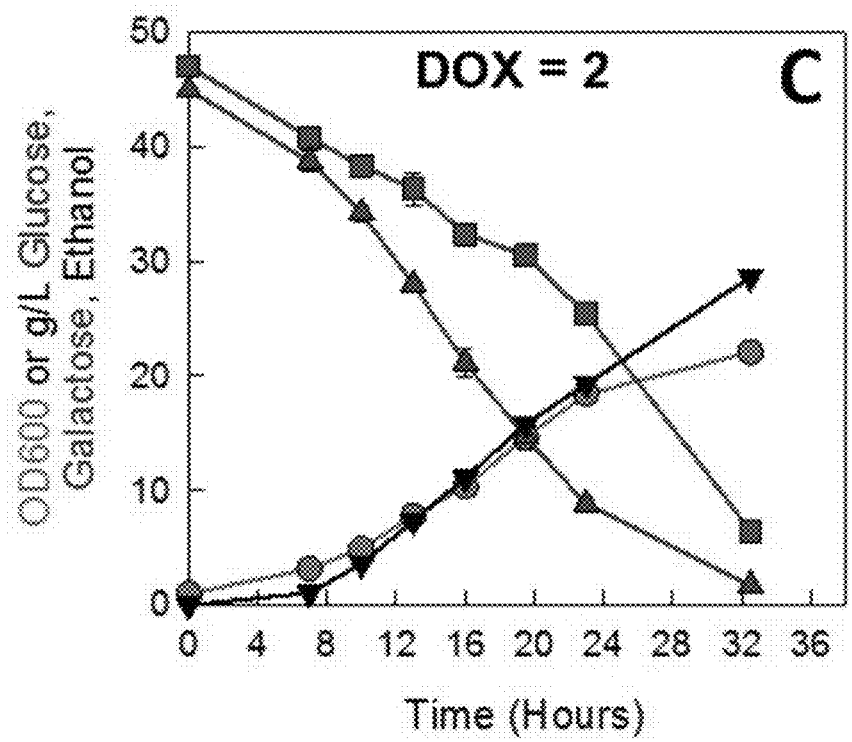
Figure 13D:
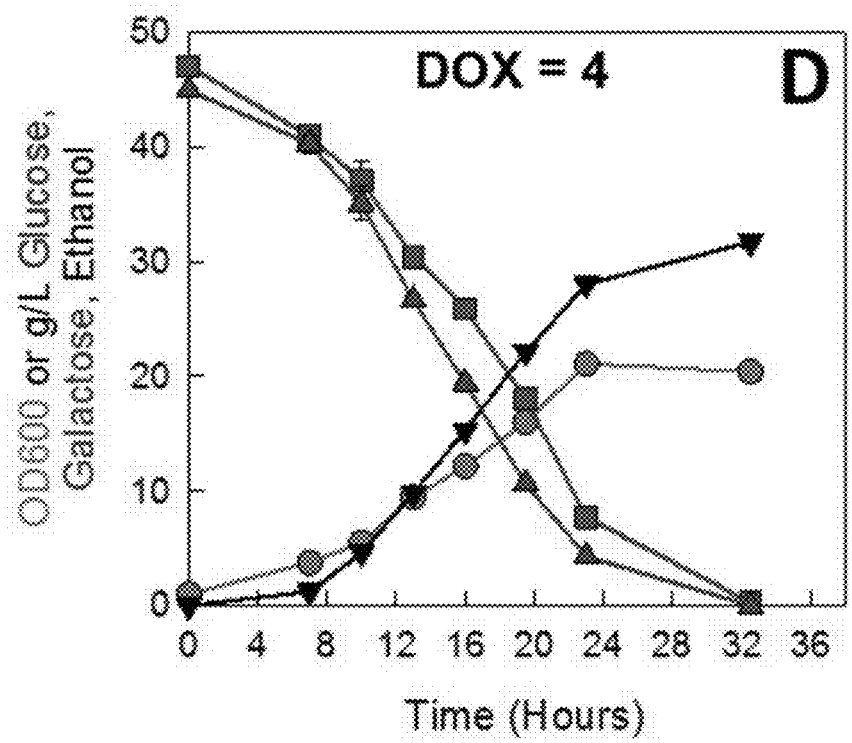
Figure 13E:
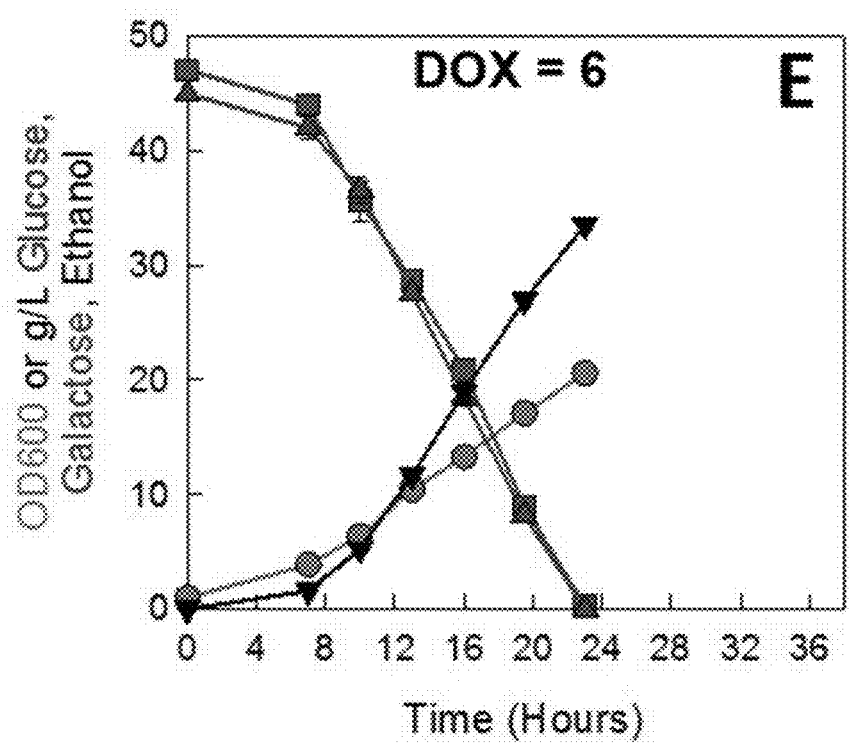
Figure 13F:
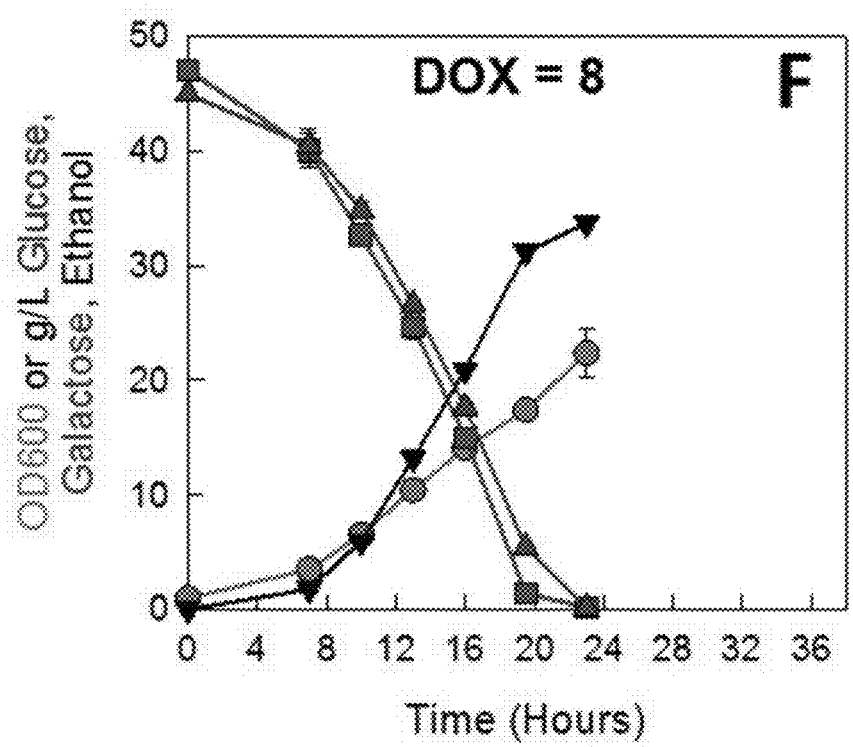
Figure 13G:
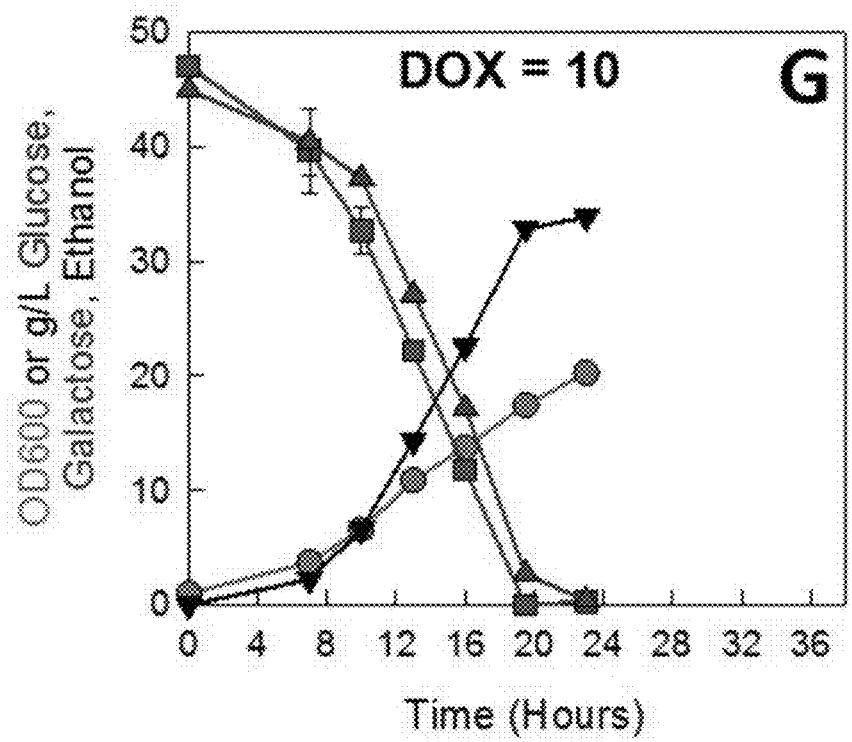
Figure 13H:
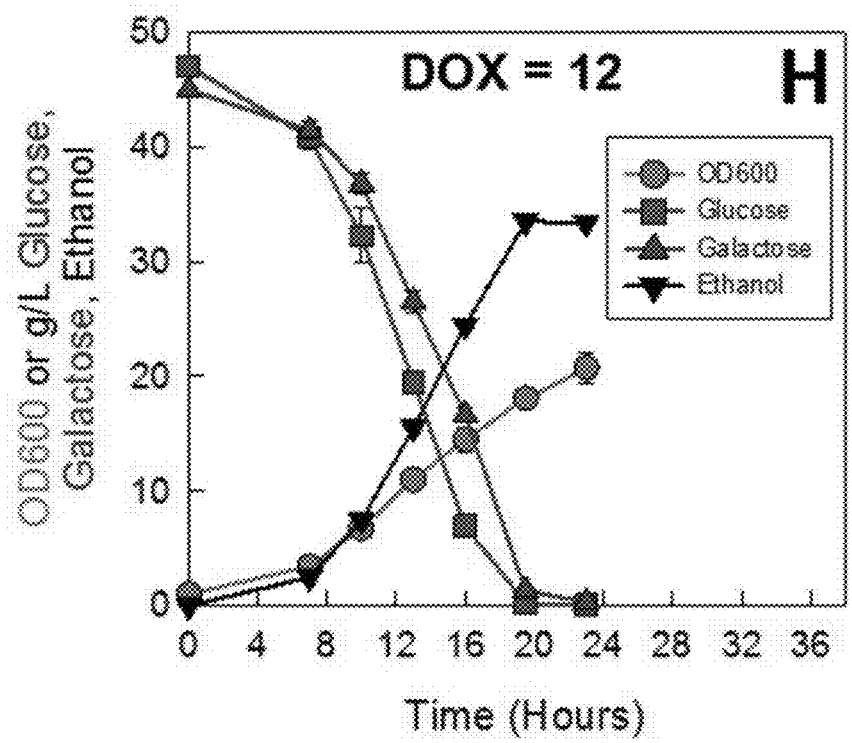
Figure 14A:
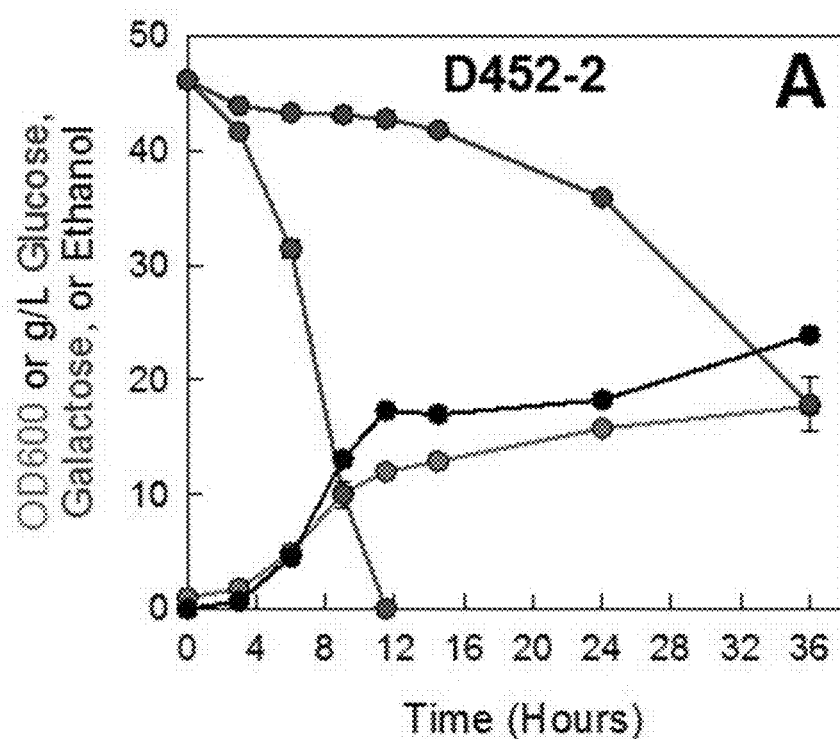
FIG. 14A-H. Modulating HXK2 expression enables simultaneous utilization of glucose and galactose. Fermentation profiles of (FIG. 14A) parent D452-2 pRS403 and (FIG. 14B-H) D452-2Δhx$^0$ with inducible HXK2 cultured in a mixture of glucose and galactose. The inducible HXK2 strain (FIG. 14B-H) was cultured with various levels of doxycycline at (FIG. 14B) 0, (FIG. 14C) 2, (FIG. 14D) 4, (FIG. 14E) 6, (FIG. 14F) 8, (FIG. 14G) 10, and (FIG. 14H) 12 μg/mL. Fermentations were performed with 25 mL YP media in 125 mL flasks at an initial OD of 1. Data points are the result of duplicate experiments with standard deviations indicated by error bars. Data points are: OD (yellow circle), glucose (blue square), galactose (purple triangle), and ethanol (black downward triangle).
Figure 14B:
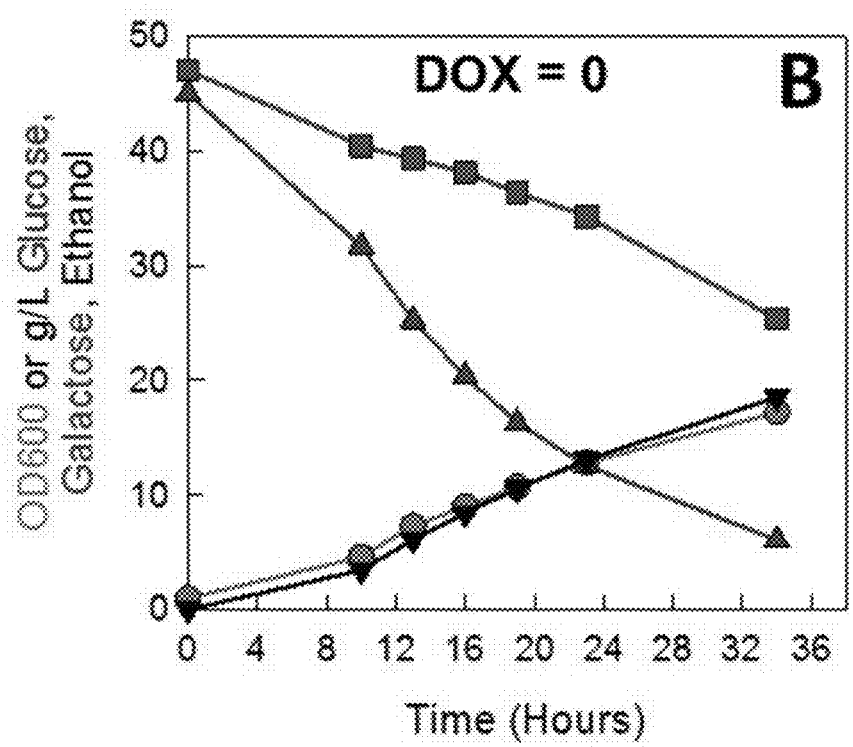
Figure 14C:
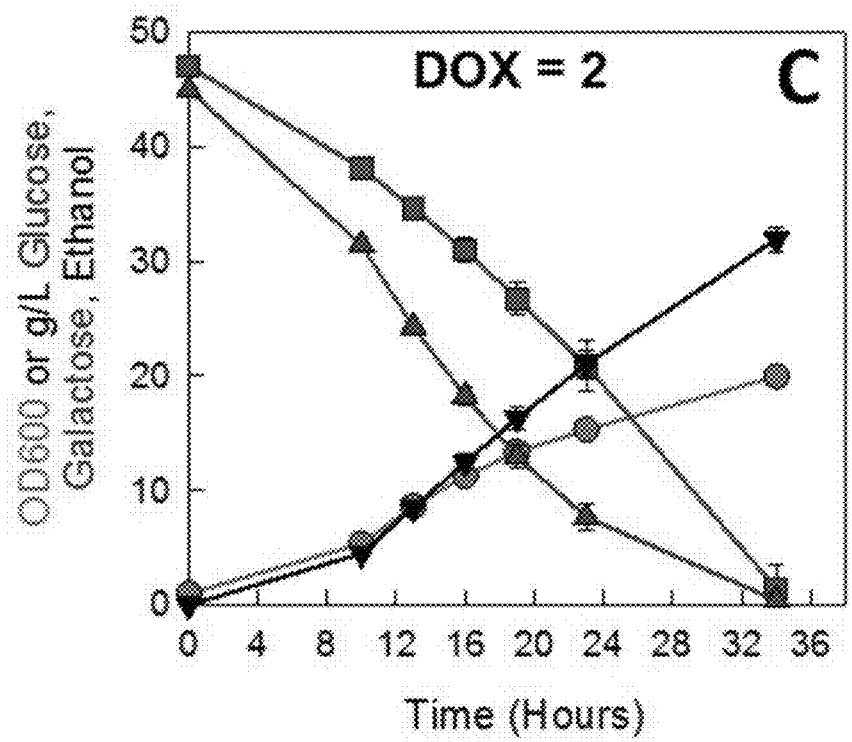
Figure 14D:
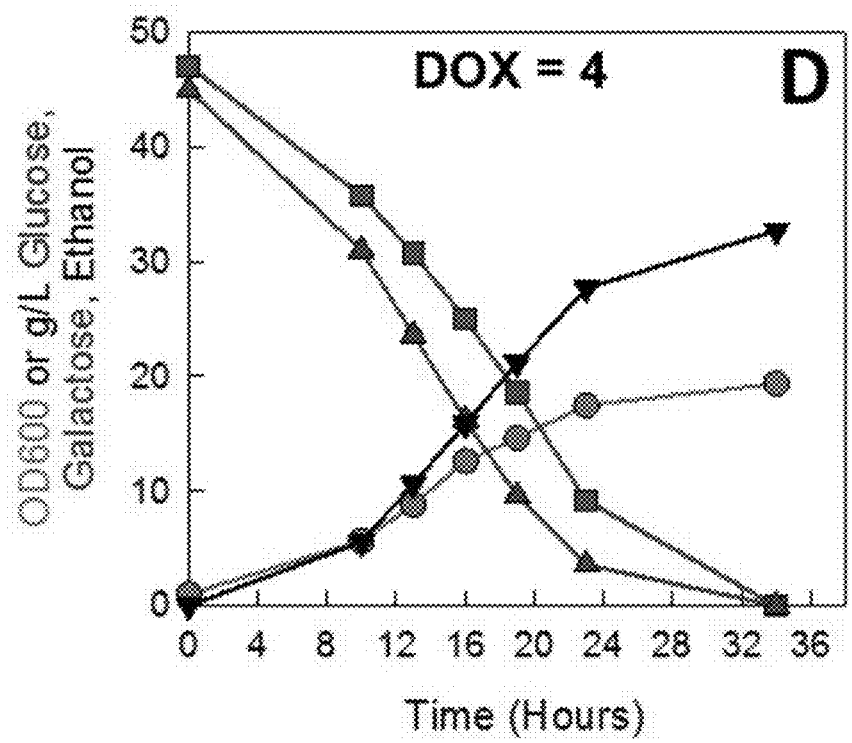
Figure 14E:
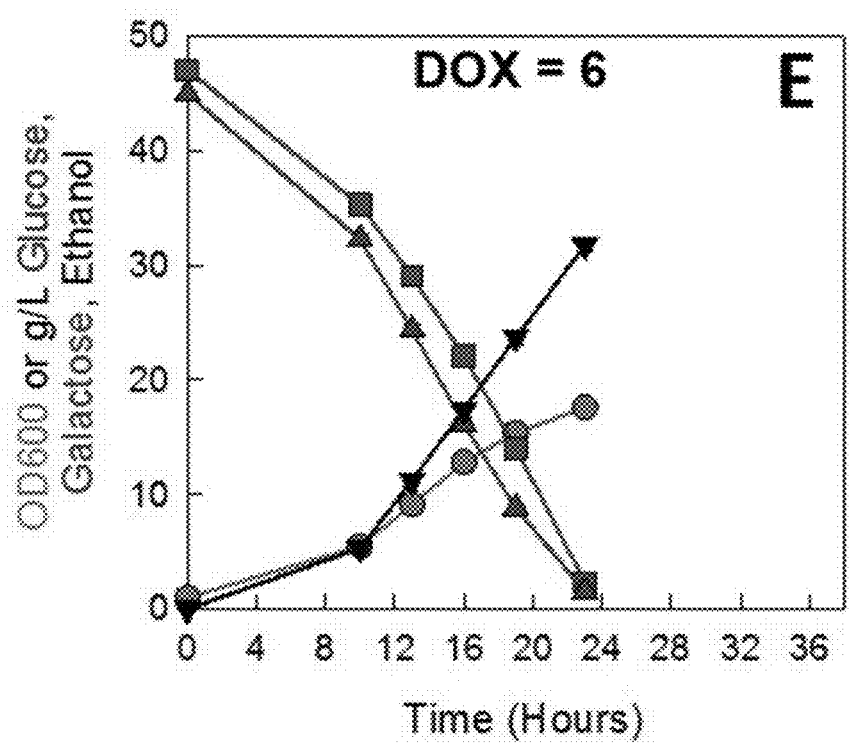
Figure 14F:
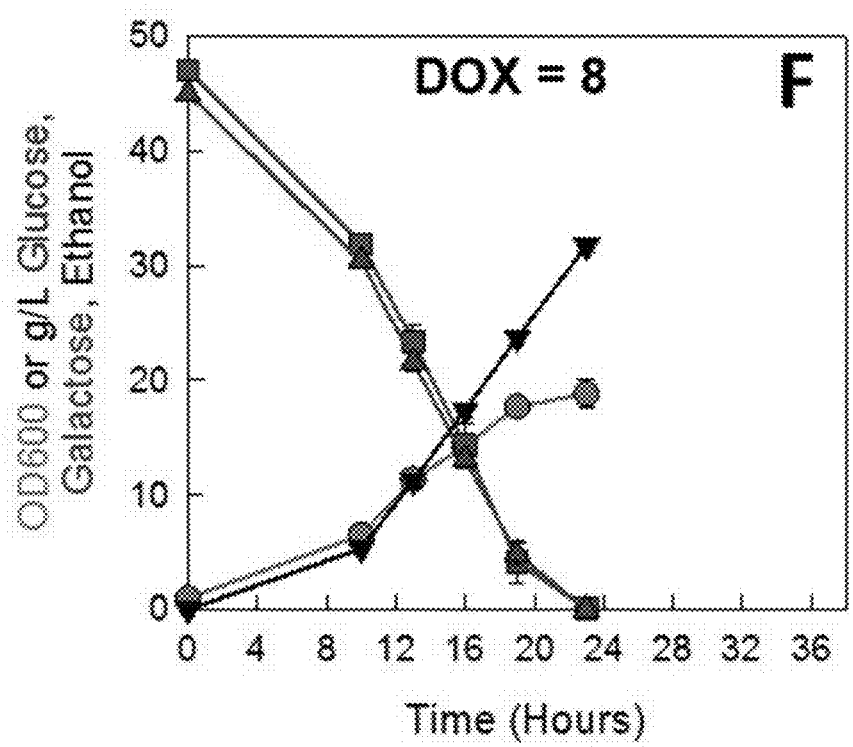
Figure 14G:
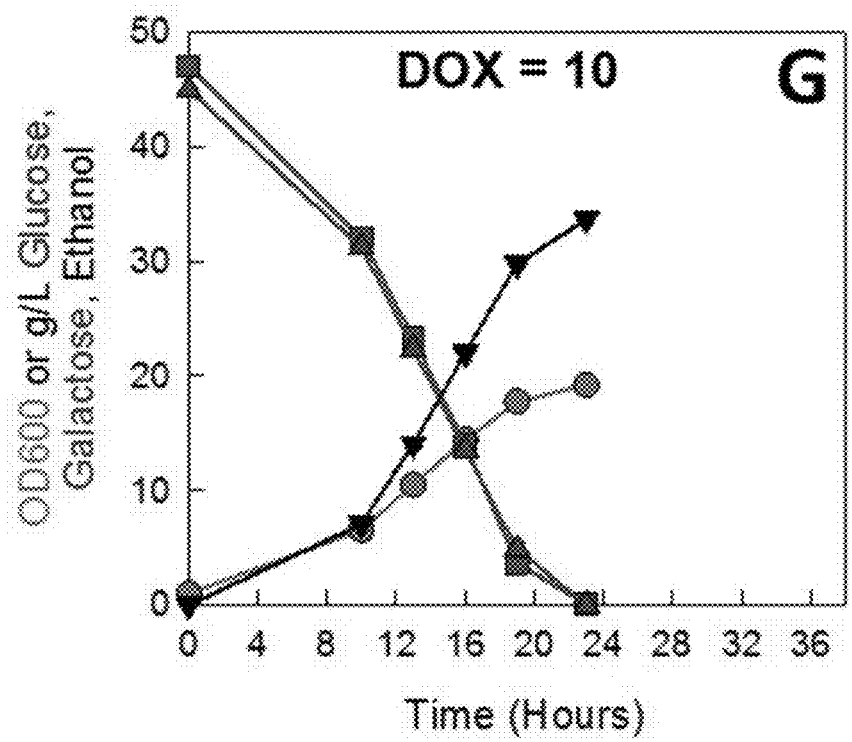
Figure 14H:
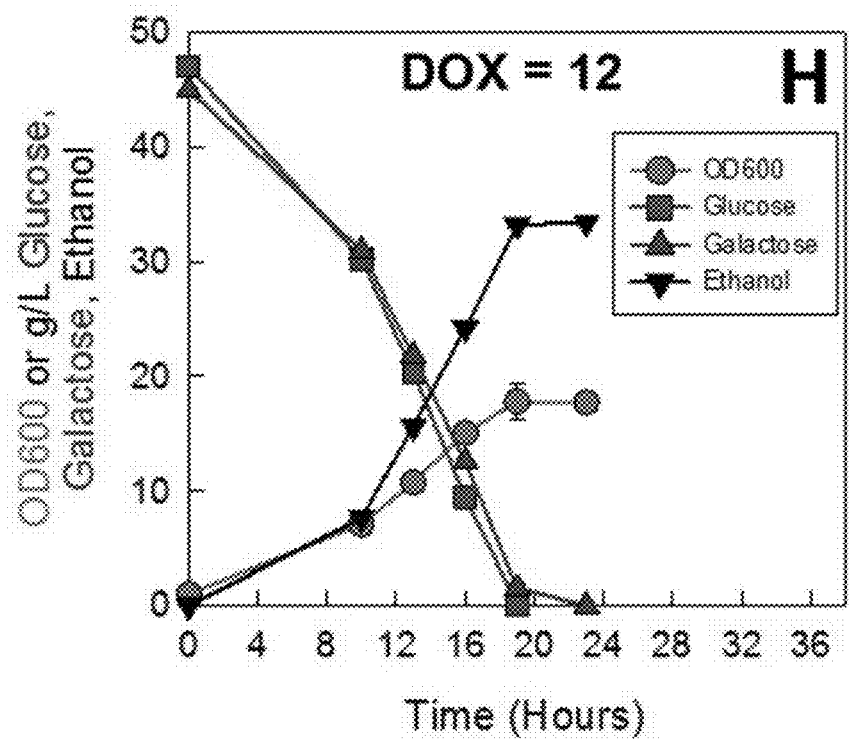

Through RNA sequencing of SR8#22, we identified transporters that were expressed in mixtures of glucose and xylose (HXT2, HXT3, HXT4 and HXT6/HXT7) (FIG. 8) and then generated four deletion mutants: SR8#22Δhxt2, SR8#22Δhxt3, SR8#22Δhxt4 and SR8#22Δhxt6Δhxt7. In order to rule out the possibility that any single sugar transporter was responsible for the phenotype of the SR8#22 strain, we examined the co-fermentation capabilities of four transporter deletion mutants of SR8#22. With some marginal changes in the rate of mixed sugar fermentation, the four deletion mutants maintained the simultaneous co-fermentation phenotype (FIG. 9). This result suggested that individual transporters were not directly associated with the co-fermentation phenotype of SR8#22.

These investigations led us to the conclusion that the simultaneous co-fermentation phenotype was not due to the altered expression of individual transporters (FIG. 9), nor mutations in hexokinases (FIG. 2D). Instead, the simultaneous co-consumption of glucose and xylose appeared to be caused by the reduced glucose consumption rate in the evolved and recreated strains (FIG. 2E).

TABLE 2

Strains

| Strain | Description | Reference |
|---|---|---|
| SR8 | Xylose-fermenting Saccharomyces cerevisiae strain | (53) |
| SR8 pRS41N-Cas9 | SR8 with Cas9 protein expressing plasmid | This study |
| SR8mGLK1 | SR8 with mutated GLK1 | This study |
| SR8mGLKmHXK2 | SR8mGLK1 with mutated HXK2 | This study |
| SR8mGLKmHXK2mHXK1 | SR8mGLK1mHXK2 with mutated HXK1 | This study |
| SR8#22 | Evolved SR8 strain with simultaneous co-fermentation phenotype | This study |
| Re#22 | Reverse-engineered SR8#22 strain by CRISPR/Cas9 system | This study |
| SR8#22 CYC1$_p$-mGLK1 | SR8#22 with insertion of a CYC1 promoter upstream of mGLK1 gene | This study |
| SR8#22 TEF1$_p$-mGLK1 | SR8#22 with insertion of a TEF1 promoter upstream of mGLK1 gene | This study |
| SR8#22 CCW12$_p$-mGLK1 | SR8#22 with insertion of a CCW12 promoter upstream of mGLK1 gene | This study |
| SR8#22Δhxt2 | SR8#22 with HXT2 deletion | This study |
| SR8#22Δhxt3 | SR8#22 with HXT3 deletion | This study |
| SR8#22Δhxt4 | SR8#22 with HXT4 deletion | This study |
| SR8#22Δhxt6Δhxt7 | SR8#22 with HXT6&HXT7 deletion | This study |
| SR8#22Δmglk1 | SR8#22 with mGLK1 deletion | This study |
| SR8#22Δmhxk1 | SR8#22 with mHXK1 deletion | This study |
| SR8#22Δmhxk22 | SR8#22 with mHXK2 deletion | This study |
| SR8-4xAuxotroph | SR8 leu2 his3 ura3 trp1 | This study |
| SR8Δ3 | SR8-4xAuxotroph with deletions in HXK1 HXK2 and GLK1 | This study |
| SR8Δ3iH2 | SR8Δ3 with pRS406-rtTA and pRS403-TetO7p-HXK2 | This study |
| D452-2 | MATα leu2 his3 ura3 | (37) |
| D452-2+403 | D452-2 with pRS403 | This study |
| D452-2Δ3i | D452-2 with deletions in HXK1, HXK2, and glk1Δ::MYO2p-rtTA(S2)-CYC1t | This study |
| D452-2Δ3iH1 | D452-2Δ3i with pRS403-TetO7p-HXK1 | This study |
| D452-2Δ3iH2 | D452-2Δ3i with pRS403-TetO7p-HXK2 | This study |
| SR8Δxyl2 | Xylitol-producing SR8 with a deletion in the XYL2 gene | This study |
| Re#22Δxyl2 | Xylitol-producing Re#22 through a deletion in the XYL2 gene | This study |

Example 3. Modulation of Wild-Type Hexokinase Expression

Figure 3:
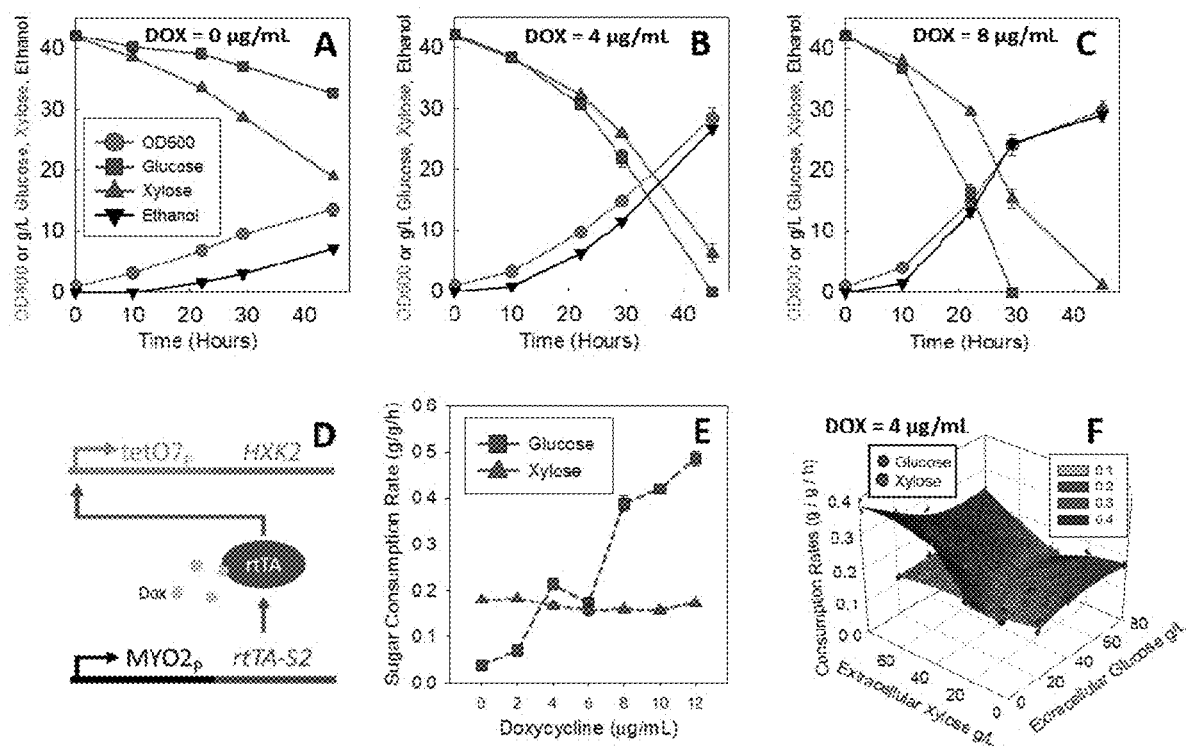
FIG. 3 panels A-F. Modulating glucose consumption rate allows simultaneous glucose and xylose utilization. (A-C) Fermentation profiles of SR8Δ3i with doxycycline concentrations of 0 (A), 4 (B), and 8 (C) μg/mL. Data points indicate OD600 (yellow circles) and glucose (blue squares), xylose (red upward triangles), and ethanol (black downward triangles) concentrations. (D) Scheme for controlling hexokinase production. The doxycycline-controlled transactivator rtTA-52 was placed under the control of the constitutive MYO2 promoter in a hexokinase-null strain background. An HXK2 expression cassette is then reintroduced with the rtTA-regulated tetO7 promoter. (E) Comparison of glucose (blue squares) and xylose (red triangles) consumption rates during mixed-sugar fermentations with varying amounts of doxycycline. (F) Effects of changing extracellular sugar concentration on sugar co-fermentation ability at a constant doxycycline concentration of 4 μg/mL. The red line indicates the intersection between the planes representing glucose and xylose consumption rates, i.e. where they are estimated to be nearly equivalent. Two-dimensional slices of each extracellular sugar concentration are displayed in FIG. 12.

Because we hypothesized that the simultaneous co-fermentation occurred as a result of the reduced glucose consumption rate, the mutant hexokinases identified through the evolution of the SR8#22 strain may not be necessary to enable simultaneous co-fermentation. To delve into this, we used a wild-type HXK2 gene under the control of a titratable expression system (doxycycline gene regulation) (8). Specifically, we constitutively expressed the rtTA transactivator and conditionally expressed the HXK2 gene under the control of the tetO7 promoter in a hexokinase null mutant of the SR8 strain (SR8Δ3iH2; see Materials and Methods). In this strain, hexokinase is expressed in the presence of doxycycline in a concentration-dependent manner, as illustrated in FIG. 3D. As confirmed in FIG. 10 and FIG. 3E, the SR8Δ3iH2 strain exhibited a glucose consumption rate dependent upon extracellular doxycycline. However, in mixed sugar fermentations the xylose consumption rate stayed largely constant across the entire range of doxycycline induction we tested (FIG. 3E). In other words, balanced co-utilization of glucose and xylose is achieved with a glucose consumption rate of about 25% of the wild-type strain, in this case when hexokinase is induced with 4-6 μg/mL of doxycycline (FIG. 3B). Inducing hexokinases with either more (FIG. 3C) or less (FIG. 3A) than 4-6 μg/mL of doxycycline resulted in an unbalanced consumption of sugars (FIG. 11). These results demonstrate that regulation of hexokinase activity alone can facilitate simultaneous co-utilization of glucose and xylose.

TABLE 3

| Mutation on hexokinase/glucokinase | | | |
|---|---|---|---|
| | GLK1 | HXK2 | HXK1 |
| SR8#22 | 265A>G Thr89Ala | 1364ΔC Pro455fs | 916T>C Ser306Pro |
| SR8mGLK1 | 265A>G Thr89Ala | Wild-type | Wild-type |
| SR8mGLK1mHXK2 | 265A>G Thr89Ala | 1364ΔC Pro455fs | Wild-type |
| Re#22 (SR8mGLK1mHXK2mHXK1) | 265A>G Thr89Ala | 1364ΔC Pro455fs | 916T>C Ser306Pro |

However, it has to be noted that the rate of xylose consumption was greatly affected by both the absolute and relative concentrations of xylose and glucose under the same concentration of 4 μg/mL doxycycline (FIG. 3F, 12). Thus, for a balanced consumption of glucose and xylose, the optimal hexokinase activity will depend on the extracellular ratio of mixed sugars, which can be obtained by one of ordinary skill in the art.

Figure 4:
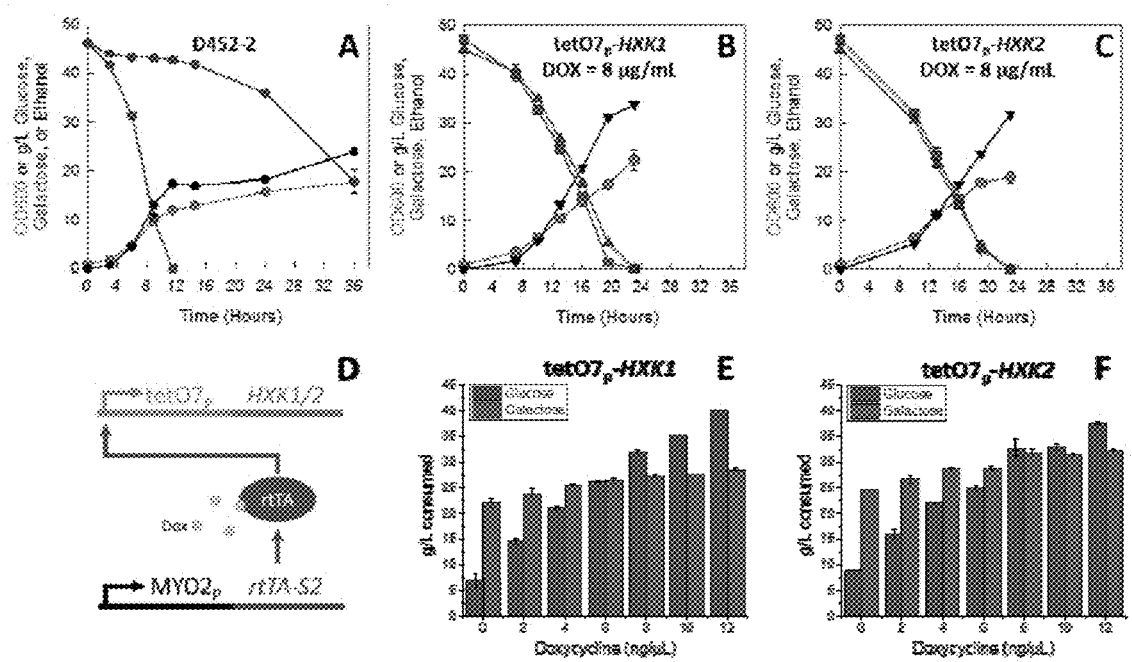
FIG. 4 panels A-F. Modulating glucose consumption rate allows simultaneous glucose and galactose utilization. (A-C) Fermentation profiles of control strain D452-2+pRS403 (A), inducible HXK1 D452-2 (B), and inducible HXK2 D452-2 (C) in mixtures of glucose and galactose. (D) Scheme for controlling hexokinase production. The doxycycline-activated transcription factor rtTA-52 was placed under the control of the constitutive MYO2 promoter in a hexokinase-null strain background. Expression of a single hexokinase is controlled by the rtTA-regulated tetO7 promoter. (E-F) Total consumed sugars after 16 hours when cultured with varied amounts of doxycycline in inducible HXK1 (E) and HXK2 (F) strains.

Example 4. Simultaneous Co-Fermentation of Glucose and Galactose by Modulating Hexokinase Activity We investigated whether a hexokinase activity-dependent mechanism of simultaneous utilization of glucose and xylose could be generalized to other sugar mixtures, such as glucose and galactose. Galactose metabolism is strongly repressed by the presence of glucose, leading to a sequential utilization of the two sugars (FIG. 4A). To avoid any interference of the xylose pathway with galactose metabolism and exclude the potential impacts of additional genetic perturbations in the SR8 strain intended to enhance xylose metabolism (36), we employed the wild-type background of the SR8 strain (D452-2 (37)) for this portion of the study. The three endogenous hexokinases were deleted in strain D452-2 and then engineered with the doxycycline-regulated expression systems of HXK1 and HXK2, resulting in the D452Δ3iH1 and D452-2Δ3iH2 strains, respectively (FIG. 4D, see Materials and Methods).

In strains D452Δ3iH1 and D452Δ3iH2, the glucose consumption rates were tightly regulated by the expression levels of either HXK1 or HXK2, while the galactose consumption rates were not majorly affected (FIG. 4E, F). When hexokinase expression was induced with 8 μg/mL doxycycline, a balanced consumption of glucose and galactose was observed with either HXK1 (FIG. 4B, 13) or HXK2 (FIG. 4C, 14). Similar to the observations with mixtures of glucose and xylose, the simultaneous consumption could be tilted in favor of either glucose or galactose by increasing or decreasing doxycycline concentration, respectively (FIG. 13, 14).

In this work we show that multiple carbon sources can be consumed simultaneously by controlling the rate of glucose consumption. Specifically, we demonstrate that mixtures of glucose/xylose and glucose/galactose can be co-consumed by reducing the consumption rate of glucose. Considering that xylose is metabolized by the pentose phosphate pathway while galactose utilization occurs through the Leloir pathway (38), this is to our knowledge the first report of a robust co-fermentation design effective throughout a range of metabolic pathways. This broad result indicates that this strategy could be generalized to include co-consumption of glucose and other industrially-relevant carbon sources such as arabinose (39, 40) and 4-deoxy-L-erythro-5-hexoseulose uronate (12).

On one hand, the expressions of GAL genes will be repressed when intracellular glucose binds to the Hxk2 protein (41). On the other hand, the expression of GAL genes will be induced by intracellular galactose. As such, the ratio of intracellular galactose and glucose would determine the status of GAL gene expression. Previous studies have shown that yeast galactose metabolic genes are repressed in response to a certain extracellular ratio of glucose and galactose (29). Beyond this, we have shown here that mixtures of both glucose/xylose and glucose/galactose can be simultaneously consumed without regard to competitive transport inhibition by reducing glucose flux. This shows that changing metabolic fluxes will alter the effects of competitive transport inhibition on intracellular accumulation of sugars. Thus, the intracellular ratio of sugar mixtures will be determined by mainly three factors: the preference of sugar transporters, the ratio of extracellular sugars, and the metabolic flux of the sugars. These results indicate that the combined effects of transport preference and metabolic flux constitute the outermost layer of glucose repression.

It was found that limiting expression of either the HXK2 or HXK1 genes enabled simultaneous utilization of glucose and galactose. We have to note that, even with maximal induction of the HXK2 gene in our system, glucose consumption was slower than wild-type and glucose repression of galactose was not observed. This indicates that HXK2 expression was still below natural levels and may have been insufficient to exert the repressive effects on GAL gene expression previously reported (30, 42).

Previous work to enable simultaneous glucose and xylose utilization has primarily focused on engineering xylose-specific transporters (23, 25, 26, 43). Although the expression of optimally engineered xylose-specific transporters enhanced xylose consumption in the presence of glucose, in most cases glucose was consumed much faster than xylose. In the case of the evolved SR8#22 strain, we found that sugar transporters were expressed differently as compared to the control strain SR8 in the mixture of glucose and xylose or in pure glucose. However, the specific xylose consumption rate didn't change between the mutant and the control in the mixture of glucose and xylose. This result lends support to previous results suggesting a link between glycolysis and the membrane composition of sugar transporters (44). Most importantly, our report demonstrates that transporter engineering is not an essential prerequisite for simultaneous glucose and xylose consumption. Rather, we found that the endogenous transport machinery has a remarkable capacity for sustaining simultaneous glucose and xylose utilization. As such, reducing the great disparity in glucose and xylose consumption rates is an additional and complementary design for enabling simultaneous co-fermentation of the two sugars.

However, although we found that the endogenous transport machinery was capable of sustaining simultaneous glucose/xylose consumption, the more rapid consumption of mixtures of glucose and galactose is likely due to a combination of factors. First, galactose is consumed faster than xylose in our strain SR8, indicating a stronger metabolic potential. Second, similar kinetic properties of Gal2p for transporting glucose and galactose (45) leads to a more balanced impact of competitive transport inhibition as compared to glucose and xylose. As such, expressing high-affinity xylose transporters and further improvement of the xylose metabolic rate should allow faster simultaneous glucose and xylose utilization while still maintaining comparable consumption rates during the fermentation.

Figure 15:
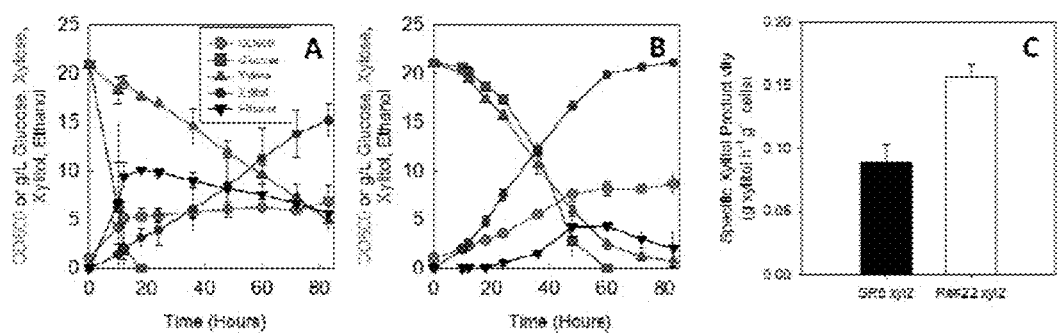
FIG. 15 panels A-C. Enhanced xylitol production through glucose/xylose co-fermentation. Fermentation profiles of (A) SR8Δxyl2 and (B) Re #22Δxyl2 cultured in a mixture of glucose and xylose. Fermentations were performed with 25 mL YP media in 125 mL flasks at an initial OD of 1. Data points are the result of duplicate experiments with standard deviations indicated by error bars. Data points are: OD (yellow circle), glucose (blue square), galactose (purple triangle), and ethanol (black downward triangle). (C) Specific xylitol productivity of SR8Δxyl2 and Re #22Δxyl2.

As this study was primarily an investigation of the effects of metabolic flux on simultaneous sugar utilization in S. cerevisiae, we aimed to produce yeast's natural by-product: ethanol. However, we also found that this strategy was particularly useful in producing xylitol from mixtures of glucose and xylose (FIG. 15). Further, recent work has demonstrated that modulating glycolytic flux can enhance the production of non-ethanol compounds (46) such as isobutanol and glucosamine. As the industry focusing on creating high-value compounds using engineered microbes continues to expand (47), this design will be particularly useful in the conversion of mixed-sugar hydrolysates to a variety of non-ethanol products.

From these examples a common thread emerges: glucose repression on consumption of alternative carbon sources can be bypassed, but glucose consumption is consistently faster. In this study, we tackle this problem with an approach which can be broadly applicable for fermenting multiple carbon sources simultaneously. Through isolation of a glucose repression-resistant mutant, determination of the underlying mechanism, and recreation of the phenotype in parent strains, we report here a general design principle allowing simultaneous sugar utilization by yeast. This study also reveals the substantial role of metabolic flux in glucose repression of alternative carbon sources.

TABLE 4

Guide RNA sequence

| Parts | Sequence | Length (bp) |
|---|---|---|
| guide RNA SNR52 promoter | TCTTTGAAAAGATAATGTATGATTATGCT TTCACTCATATTTATACAGAAACTTGATG TTTTCTTTCGAGTATATACAAGGTGATTA CATGTACGTTTGAAGTACAACTCTAGATT TTGTAGTGCCCTCTTGGGCTAGCGGTAAA GGTGCGCATTTTTTCACACCCTACAATGT TCTGTTCAAAAGATTTTGGTCAAACGCTG TAGAAGTGAAAGTTGGTGCGCATGTTTCG GCGTTCGAAACTTCTCCGCAGTGAAAGAT AAATGATC (SEQ ID NO: 4) | 269 |
| HXK1-R target | TTCACCCAAGTAGTAACCGG (SEQ ID NO: 5) | 20 |
| GLK1-R target | AACAGAACATATACGGAAAT (SEQ ID NO: 6) | 20 |
| HXK2-R target | GTTCCTGCTGAAGATGGTTC (SEQ ID NO: 7) | 20 |
| HXT2 target | CAAAGCCAATCGCCGCATAT (SEQ ID NO: 8) | 20 |
| GLK1$_P$ target | TGATAGAGTTGTATTAGTGG (SEQ ID NO: 9) | 20 |
| HXK1 target | TAGTTTATACTTGGATTGAG (SEQ ID NO: 10) | 20 |
| Structural crRNA | GTTTTAGAGCTAGAAATAGCAAGTTAAAA TAAGGCTAGTCCGTTATCAACTTGAAAAA GTGGCACCGAGTCGGTGGTGC (SEQ ID NO: 11) | 79 |
| SUP4 terminator | TTTTTTTGTTTTTTATGTCT (SEQ ID NO: 12) | 20 |

TABLE 5

Primers

| Name | Sequence | Description |
|---|---|---|
| CST518 | CAAAGCCAATCGCCGCATATGTTTTAGAGCTAG AAATAGCAAGTTAAA (SEQ ID NO: 13) | forward primer for HXT2 gRNA construction |
| C5T519 | ACATATGCGGCGATTGGCTTTGGATCATTTATCT TTCACTGCGGA (SEQ ID NO: 14) | reverse primer for HXT2 gRNA construction |
| C5T520 | CAAAGCCAATCGCCGCATAT (SEQ ID NO: 15) | forward primer for HXT2 gRNA construction confirmation |
| S00459 | GGAGCGCGGTGTTTTACTAGCCGCCGACCTGGG TGGTGCTAATTTCCGTATATGTTCTGT (SEQ ID NO: 16) | forward primer for mGLK1 recreation donor |
| S00460 | CATTTGCTCCATGGAGAAAGTATGATCTCCATG CAAGTTAACAGAACATATACGGAAATT (SEQ ID NO: 17) | reverse primer for mGLK1 recreation donor |

TABLE 5-continued

Primers

| Name | Sequence | Description |
|---|---|---|
| S008 | GGCGGATCCATGTCATTCGACGACTTACACAA (SEQ ID NO: 18) | forward primer for mGLK1 construction confirmation |
| S009 | GGCGTCGACTCATGCTACAAGCGCACACA (SEQ ID NO: 62) | reverse primer for mGLK1 construction confirmation |
| SO0510 | GACGACTACCCAATCAAGATTGTTCTGCTGAAG ATGGTTCCAGTGCTGGTGCCGCTGTTA (SEQ ID NO: 80) | forward primer for mHXK2 recreation donor |
| SO0511 | GACTTACCTTCAGCAATTCTTTTTTGGGCCAAAG CAGCAATAACAGCGGCACCAGCACTG (SEQ ID NO: 19) | reverse primer for mHXK2 recreation donor |
| SO0170 | GGCGGATCCTTAGCACTACTGGGACAAGC (SEQ ID NO: 20) | forward primer for mHXK2 construction confirmation |
| SO0171 | GGCGCGGCCGCGAGGAAGTGTAGAGAGGGTT (SEQ ID NO: 21) | reverse primer for mHXK2 construction confirmation |
| SO0546 | ATCTCCAAGACCTGGTCAACAAGCTTTTGAAAA GATGACTCCAGGTTACTACTTGGGTGA (SEQ ID NO: 22) | forward primer for mHXK1 recreation donor |
| SO0547 | GCCCTTCTCGTTTAATTCAAGTAACACTAGACGC AACAATTCACCCAAGTAGTAACCTGG (SEQ ID NO: 23) | reverse primer for mHXK1 recreation donor |
| S004 | GCCGGATCCCACCTGGTCTTACCTCGAAC (SEQ ID NO: 24) | forward primer for mHXK1 construction confirmation |
| S005 | GCCGCGGCCGCCGACTTTCTCCCTCTCTCCA (SEQ ID NO: 25) | reverse primer for mHXK1 construction confirmation |
| SO0632 | GTTGACAGGTCAGTTAAGGCACAG (SEQ ID NO: 26) | forward primer for ΔHXT2 confirmation |
| SO0633 | GTTGATCATCGAGTCGCTCG (SEQ ID NO: 27) | reverse primer for ΔHXT2 confirmation |
| Jin3266 | TCTCAATTCCTCTTATATTAGATTATAAGAACAA CAAATTAAATTACAAAAGACTTATAAAGCAAC ATACGAGCGACTCGATGATCAAC (SEQ ID NO: 28) | forward primer for ΔHXT2 donor |
| Jin3267 | GAAGATCATCTATTAAAGTATTAGTAGCCATTA GCCTTAAAAAAATCAGTGCTAGTTTAAGTATAA TCTCGTTGATCATCGAGTCGCTCG (SEQ ID NO: 29) | reverse primer for ΔHXT2 donor |
| Jin2335 | AATAGAATCACAAACAAAATTTACATCTGAGTT AAACAATCCAGCTGAAGCTTCGTACGC (SEQ ID NO: 30) | forward primer for ΔHXT3 (Cre-Loxp) |
| Jin2336 | AAATACACTATTATTCAGCACTACGGTTTAGCGT GAAAGCATAGGCCACTAGTGGATCTG (SEQ ID NO: 31) | reverse primer for ΔHXT3 (Cre-Loxp) |
| Jin2337 | GGTTTGGTTTTGAAACACTTTTACAATAAAATCT GCCAAAACAGCTGAAGCTTCGTACGC (SEQ ID NO: 32) | forward primer for ΔHXT4 (Cre-Loxp) |
| Jin2338 | ATTCCTTGAAGGAAGTCTATATTATTTAATTAAC TGACGCATAGGCCACTAGTGGATCTG (SEQ ID NO: 33) | reverse primer for ΔHXT4 (Cre-Loxp) |
| SO0401 | AACATATAAAAGAGCTCGAGAAAAGACATAT GGTTTGTAACTATCTTCTTCTTTTTTCCAATTTTT CTGTCAGCTGAAGCTTCGTACGC (SEQ ID NO: 34) | forward primer for ΔHXT6&7 (Cre-Loxp) |
| SO0406 | TTCTGAGAACAAATGATCAAAAACTTGAAAATT AAACTGTATTATTTTGTATATATTAAAAACGTAT T GCATAGGCCACTAGTGGATCTG (SEQ ID NO: 35) | reverse primer for ΔHXT6&7 (Cre-Loxp) |

TABLE 5-continued

Primers

| Name | Sequence | Description |
|---|---|---|
| SO0148 | GGATGTATGGGCTAAATG (SEQ ID NO: 36) | reverse primer for confirmation of Cre-Loxp deletion |
| Jin2343 | ATTCGGTTAAACTCTCGG (SEQ ID NO: 37) | forward primer for ΔHXT3 confirmation |
| Jin2344 | TTCATGAAAAAITCCACIAGT (SEQ ID NO: 38) | forward primer for ΔHXT4 confirmation |
| SO0407 | GCGCCAAGACAAATGTTTC (SEQ ID NO: 39) | forward primer for ΔHXT6&7 confirmation |
| SO0668 | CCCCCCCATCAGTGCCCAACTCAGCTTCCGTAA ACCACAACAAAAGCGCCAGTTCATTTG (SEQ ID NO: 40) | forward primer of donor for using CYC1 promoter to control mGLK1 |
| SO0643 | TCTCTCAGTGGCTTTGTGTAAGTCGTCGAATGAC ATGTGTGTATTTGTGTTTGTGTG (SEQ ID NO: 41) | reverse primer of donor for using CYC1 promoter to control mGLK1 |
| SO0669 | CCCATCAGTGCCCAACTCAGCTTCCGTAAACCA CAACAAATGTTTCTACTCCTTTTTTAC (SEQ ID NO: 42) | forward primer of donor for using TEF1 promoter to control mGLK1 |
| SO0670 | CTCAGTGGCTTTGTGTAAGTCGTCGAATGACATT TTGTAATTAAAACTTAGATTAGATTG (SEQ ID NO: 43) | reverse primer of donor for using TEF1 promoter to control mGLK1 |
| SO0639 | GCGTAACAAAATATATATATATATATATATA TATGTATGTCACGCAAAAGAAAACCTT (SEQ ID NO: 44) | forward primer of donor for using CCW12 promoter to control mGLK1 |
| SO0637 | TCTCTCAGTGGCTTTGTGTAAGTCGTCGAATGAC ATTATTGATATAGTGTTTAAGCGAAT (SEQ ID NO: 45) | reverse primer of donor for using CCW12 promoter to control mGLK1 |
| SO0225 | TATAAGTGGTGTGCCGACG (SEQ ID NO: 46) | forward primer for mGLK1 promoter substitution confirmation |
| SO0641 | GATGACCGCTCTCTCAGTGG (SEQ ID NO: 47) | reverse primer for mGLK1 promoter substitution confirmation |
| SO0142 | CAATTAGAATTCTTTTCTTTTAATCAAACTCACC CAAACAACTCAATTAGAATACTGAAAAAATAAG ATG CGTACGCTGCAGGTCGAC (SEQ ID NO: 48) | forward primer for ΔHXK1 (Cre-Loxp) |
| SO0143 | ATCACTCATAAGAATAATAATATTAAGGGAGGG AAAAACACATTTATATTTCATTACATTTTTTTCA TTA ATCGATGAATTCGAGCTCG (SEQ ID NO: 49) | reverse primer for ΔHXK1 (Cre-Loxp) |
| SO0179 | GCTTTTTCTTTGAAAAGGTTGTAGGAATATAATT CTCCACACATAATAAGTACGCTAATTAAATAAA ATG CGTACGCTGCAGGTCGAC (SEQ ID NO: 50) | forward primer for ΔHXK2 (Cre-Loxp) |
| SO0180 | AAAACATGTTCACATAAGTAGAAAAAGGGCACC TTCTTGTTGTTCAAACTTAATTTACAAATTAAGT TTA ATCGATGAATTCGAGCTCG (SEQ ID NO: 51) | reverse primer for ΔHXK2 (Cre-Loxp) |
| SO0252 | CCCCATCAGTGCCCAACTCAGCTTCCGTAAACC ACAACACCACCACTAATCAACTCTATCATACA CAAG CAGCTGAAGCTTCGTACGC (SEQ ID NO: 52) | forward primer for ΔGLK1 (Cre-Loxp) |
| SO0253 | TATATATAAAGGAGAGAAGATGGTAAGTACGGT GGGATACGTACACAAACCAAAAAAATGTAAAA AGA GCATAGGCCACTAGTGGATCTG (SEQ ID NO: 53) | reverse primer for ΔGLK1 (Cre-Loxp) |
| JIN3707 | Cccccatcagtgcccaactcagcttccgtaaaccacaa caccaccactaatacaactctatcatacacaagTAAG GCGAGCTCATACCGTC (SEQ ID NO: 54) | ΔGLK1_Cas9_F |

TABLE 5-continued

Primers

| Name | Sequence | Description |
|---|---|---|
| JIN3708 | Tatatatataaaggagagaagatggtaagtacggtgg gatacgtacacaaaccaaaaaaatgtaaaaagaGACG GTATGAGCTCGCCTTA (SEQ ID NO: 55) | ΔGLK1_Cas9_R |
| JIN3709 | Taccaattagacatgctgcttgc (SEQ ID NO: 56) | ΔGLK1_Confirm_F |
| JIN3710 | GACGGTATGAGCTCGCCTTA (SEQ ID NO: 57) | ΔGLK1_Confirm_R |
| JIN3762 | Actcaattagaattcttttcttttaatcaaact- caccc aaacaactcaattagaatactgaaaaaataagGTGTAA CTCAGATGAGCTAC (SEQ ID NO: 58) | ΔHXK1_Cas9_F |
| JIN3763 | Ggcatcactcataagaataataatat- taagggagggaa aaacacatttatatttcattacatttttttcaGTAGCT CATCTGAGTTACAC (SEQ ID NO: 59) | ΔHXK1_Cas9_R |
| JIN3764 | GCCAGATCTCAGTATAGCAG (SEQ ID NO: 60) | ΔHXK1_Confirm_F |
| JIN3765 | GTAGCTCATCTGAGTTACAC (SEQ ID NO: 61) | ΔHXK1_Confirm_R |
| JIN3767 | Ttcgcttttctttgaaaaggttgtaggaatataat- tct ccacacataataagtacgctaattaaataaaACGAC- CGA CGTACGATTCAA (SEQ ID NO: 63) | ΔHXK2_Cas9_F |
| JIN3768 | Tagaaaacatgttcacataagtagaaaaagggcac- cttc ttgttgttcaaacttaatttacaaattaagtTT- GAATCG TACGTCGGTCGT (SEQ ID NO: 64) | ΔHXK2_Cas9_R |
| JIN3769 | GCTCCAGAGCTCCACATTG (SEQ ID NO: 65) | ΔHXK2_Confirm_F |
| JIN3770 | TTGAATCGTACGTCGGTCGT (SEQ ID NO: 66) | ΔHXK2_Confirm_R |
| JIN5143 | AAATTTTAGACGCGGCGCTTGCACCCCGCATTA TAAGTGGTGctcaagcaaggttttcag (SEQ ID NO: 67) | ΔGLK1::rtTA_F |
| JIN5144 | TACCGGTACCGAAAATACATCCGATGACCGGCT CCGAGgaattccacttaatgtatcaac (SEQ ID NO: 68) | ΔGLK1::rtTA_R |
| JIN5145 | GTGTCACTAGGTGCAATTGCC (SEQ ID NO: 69) | ΔGLK1::rtTA_Confirm_F |
| JIN5146 | CGACAGCACTTCGGATGA (SEQ ID NO: 70) | ΔGLK1::rtTA_Confirm_R |

REFERENCES

1. Chu S & Majumdar A (2012) Opportunities and challenges for a sustainable energy future. *nature* 488(7411): 294-303.
2. Duina A A, Miller M E, & Keeney J B (2014) Budding yeast for budding geneticists: a primer on the *Saccharomyces cerevisiae* model system. *Genetics* 197(1):33-48.
3. Sauer B (1987) Functional expression of the cre-lox site-specific recombination system in the yeast *Saccharomyces cerevisiae*. *Molecular and cellular biology* 7(6): 2087-2096.
4. DiCarlo J E, et al. (2013) Genome engineering in *Saccharomyces cerevisiae* using CRISPR-Cas systems. *Nucleic acids research*:gkt135.
5. Sikorski R S & Hieter P (1989) A system of shuttle vectors and yeast host strains designed for efficient manipulation of DNA in *Saccharomyces cerevisiae*. *Genetics* 122(1): 19-27.
6. Redden H, Morse N, & Alper H S (2015) The synthetic biology toolbox for tuning gene expression in yeast. *FEMS yeast research* 15(1):1-10.
7. Lam F H, Ghaderi A, Fink G R, & Stephanopoulos G (2014) Engineering alcohol tolerance in yeast. *Science* 346(6205):71-75.
8. Jeffries T W & Jin Y-S (2000) Ethanol and thermotolerance in the bioconversion of xylose by yeasts.
9. Phitsuwan P, Sakka K, & Ratanakhanokchai K (2013) Improvement of lignocellulosic biomass in planta: a review of feedstocks, biomass recalcitrance, and strategic manipulation of ideal plants designed for ethanol production and processability. *Biomass and Bioenergy* 58:390-405.
10. Wei N, Quarterman J, & Jin Y-S(2013) Marine macroalgae: an untapped resource for producing fuels and chemicals. *Trends in biotechnology* 31(2):70-77.
11. Kim S R, Ha S J, Wei N, Oh E J, & Jin Y S (2012) Simultaneous co-fermentation of mixed sugars: a promising strategy for producing cellulosic ethanol. *Trends Biotechnol* 30(5):274-282.

12. Enquist-Newman M, et al. (2014) Efficient ethanol production from brown macroalgae sugars by a synthetic yeast platform. *Nature* 505(7482):239-243.
13. Ha S-J, et al. (2013) Continuous co-fermentation of cellobiose and xylose by engineered *Saccharomyces cerevisiae*. *Bioresource technology* 149:525-531.
14. Lebeau T, Jouenne T, & Junter G-A (1997) Simultaneous fermentation of glucose and xylose by pure and mixed cultures of *Saccharomyces cerevisiae* and *Candida shehatae* immobilized in a two-chambered bioreactor. *Enzyme and microbial technology* 21(4):265-272.
15. Lebeau T, Jouenne T, & Junter G-A (1998) Continuous alcoholic fermentation of glucose/xylose mixtures by co-immobilized *Saccharomyces cerevisiae* and *Candida shehatae*. *Applied microbiology and biotechnology* 50(3): 309-313.
16. Grootjen D, Meijlink L, Van der Lans R, & Luyben K C A (1990) Cofermentation of glucose and xylose with immobilized *Pichia stipitis* and *Saccharomyces cerevisiae*. *Enzyme and microbial technology* 12(11):860-864.
17. Laplace J M, Delgenes J P, Moletta R, & Navarro J M (1993) Cofermentation of glucose and xylose to ethanol by a respiratory-deficient mutant of *Saccharomyces cerevisiae* co-cultivated with a xylose-fermenting yeast. *Journal of fermentation and bioengineering* 75(3):207-212.
18. Galazka J M, et al. (2010) Cellodextrin transport in yeast for improved biofuel production. *Science* 330(6000):84-86.
19. Ha S J, et al. (2011) Engineered *Saccharomyces cerevisiae* capable of simultaneous cellobiose and xylose fermentation. *Proc Natl Acad Sci USA* 108(2):504-509.
20. Li S, et al. (2010) Overcoming glucose repression in mixed sugar fermentation by co-expressing a cellobiose transporter and a β-glucosidase in *Saccharomyces cerevisiae*. *Molecular BioSystems* 6(11):2129-2132.
21. Bertilsson M, Andersson J, & Lidén G (2008) Modeling simultaneous glucose and xylose uptake in *Saccharomyces cerevisiae* from kinetics and gene expression of sugar transporters. *Bioprocess and biosystems engineering* 31(4):369-377.
22. Subtil T & Boles E (2012) Competition between pentoses and glucose during uptake and catabolism in recombinant *Saccharomyces cerevisiae*. *Biotechnol biofuels* 5(1):14.
23. Farwick A, Bruder S, Schadeweg V, Oreb M, & Boles E (2014) Engineering of yeast hexose transporters to transport D-xylose without inhibition by D-glucose. *Proceedings of the National Academy of Sciences* 111(14):5159-5164.
24. Young E M, Tong A, Bui H, Spofford C, & Alper H S (2014) Rewiring yeast sugar transporter preference through modifying a conserved protein motif. *Proceedings of the National Academy of Sciences* 111(1):131-136.
25. Shin H Y, et al. (2015) An engineered cryptic Hxt11 sugar transporter facilitates glucose-xylose co-consumption in *Saccharomyces cerevisiae*. *Biotechnology for biofuels* 8(1):1.
26. Wang M, Yu C, & Zhao H (2015) Directed evolution of xylose specific transporters to facilitate glucose-xylose co-utilization. *Biotechnology and bioengineering*.
27. Wang C, et al. (2015) Cloning and characterization of heterologous transporters in *Saccharomyces cerevisiae* and identification of important amino acids for xylose utilization. *Metabolic engineering*.
28. Apel A R, Ouellet M, Szmidt-Middleton H, Keasling J D, & Mukhopadhyay A (2016) Evolved hexose transporter enhances xylose uptake and glucose/xylose co-utilization in *Saccharomyces cerevisiae*. *Scientific Reports* 6:19512.
29. Escalante-Chong R, et al. (2015) Galactose metabolic genes in yeast respond to a ratio of galactose and glucose. *Proceedings of the National Academy of Sciences* 112 (5): 1636-1641.
30. Raamsdonk L M, et al. (2001) Co-consumption of sugars or ethanol and glucose in a *Saccharomyces cerevisiae* strain deleted in the HXK2 gene. *Yeast* 18(11):1023-1033.
31. Ostergaard S, Walløe K O, Gomes C S, Olsson L, & Nielsen J (2001) The impact of GAL6, GAL80, and MIG1 on glucose control of the GAL system in *Saccharomyces cerevisiae*. *FEMS yeast research* 1(1):47-55.
32. Katahira S, Mizuike A, Fukuda H, & Kondo A (2006) Ethanol fermentation from lignocellulosic hydrolysate by a recombinant xylose- and cellooligosaccharide-assimilating yeast strain. *Appl Microbiol Biotechnol* 72(6):1136-1143.
33. Ho N W, Chen Z, & Brainard A P (1998) Genetically engineered *Saccharomyces* yeast capable of effective cofermentation of glucose and xylose. *Appl Environ Microbiol* 64(5): 1852-1859.
34. Farwick A, Bruder S, Schadeweg V, Oreb M, & Boles E (2014) Engineering of yeast hexose transporters to transport D-xylose without inhibition by D-glucose. *Proc Natl Acad Sci USA* 111(14):5159-5164.
35. Li X, et al. (2016) Comparison of xylose fermentation by two high-performance engineered strains of *Saccharomyces cerevisiae*. *Biotechnology Reports*.
36. Kim S R, et al. (2013) Rational and evolutionary engineering approaches uncover a small set of genetic changes efficient for rapid xylose fermentation in *Saccharomyces cerevisiae*. *PloS one* 8(2):e57048.
37. Hosaka K, Nikawa J-i, Kodaki T, & Yamashita S (1992) A dominant mutation that alters the regulation of INO1 expression in *Saccharomyces cerevisiae*. *Journal of biochemistry* 111(3):352-358.
38. Sellick C A, Campbell R N, & Reece R J (2008) Galactose metabolism in yeast—structure and regulation of the Leloir pathway enzymes and the genes encoding them. *International review of cell and molecular biology* 269:111-150.
39. Saha B C (2003) Hemicellulose bioconversion. *Journal of Industrial Microbiology and Biotechnology* 30(5):279-291.
40. Hahn-Hägerdal B, Karhumaa K, Fonseca C, Spencer-Martins I, & Gorwa-Grauslund M F (2007) Towards industrial pentose-fermenting yeast strains. *Applied microbiology and biotechnology* 74(5):937-953.
41. Ahuatzi D, Riera A, Peláez R, Herrero P, & Moreno F (2007) Hxk2 regulates the phosphorylation state of Mig1 and therefore its nucleocytoplasmic distribution. *Journal of Biological Chemistry* 282(7):4485-4493.
42. Bae Y-H, Kweon D-H, Park Y-C, & Seo J-H (2014) Deletion of the HXK2 gene in *Saccharomyces cerevisiae* enables mixed sugar fermentation of glucose and galactose in oxygen-limited conditions. *Process Biochemistry* 49(4):547-553.
43. Nijland J G, et al. (2014) Engineering of an endogenous hexose transporter into a specific D-xylose transporter facilitates glucose-xylose co-consumption in *Saccharomyces cerevisiae*. *Biotechnology for biofuels* 7(1):168.
44. Cairey-Remonnay A, Deffaud J, Wésolowski-Louvel M, Lemaire M, & Soulard A (2015) Glycolysis Controls Plasma Membrane Glucose Sensors To Promote Glucose Signaling in Yeasts. *Molecular and cellular biology* 35(4):747-757.

45. Kasahara T & Kasahara M (2000) Three aromatic amino acid residues critical for galactose transport in yeast Gal2 transporter. *Journal of Biological Chemistry* 275(6):4422-4428.
46. Tan S Z, Manchester S, & Prather K L (2015) Controlling Central Carbon Metabolism for Improved Pathway Yields in *Saccharomyces cerevisiae*. *ACS synthetic biology*.
47. Hayden E C (2014) Synthetic-biology firms shift focus. *Nature* 505(7485):598-598.
48. Kim S R, et al. (2015) Deletion of PHO13, encoding haloacid dehalogenase type IIA phosphatase, results in upregulation of the pentose phosphate pathway in *Saccharomyces cerevisiae*. *Applied and environmental microbiology* 81(5):1601-1609.
49. Xu H, et al. (2016) PHO13 deletion-induced transcriptional activation prevents sedoheptulose accumulation during xylose metabolism in engineered *Saccharomyces cerevisiae*. *Metabolic engineering* 34:88-96.
50. Li C K, et al. (2011) FastCloning: a highly simplified, purification-free, sequence- and ligation-independent PCR cloning method. *BMC Biotechnol* 11.
51. Zhang G-C, et al. (2014) Construction of a quadruple auxotrophic mutant of an industrial polyploid *Saccharomyces cerevisiae* strain by using RNA-guided Cas9 nuclease. *Applied and environmental microbiology* 80(24):7694-7701.
52. Zilio N, Wehrkamp-Richter S, & Boddy M N (2012) A new versatile system for rapid control of gene expression in the fission yeast *Schizosaccharomyces pombe*. *Yeast* 29(10):425-434.
53. Kim S R, et al. (2013) Rational and evolutionary engineering approaches uncover a small set of genetic changes efficient for rapid xylose fermentation in *Saccharomyces cerevisiae*. *PLoS One* 8(2):e57048.

What is claimed is:

1. A genetically engineered yeast having attenuated expression, as compared to a wild-type or control yeast, of a polynucleotide encoding: a hexokinase isoenzyme 1 ("Hxk1") polypeptide; a hexokinase isoenzyme 2 ("Hxk2") polypeptide and a glucokinase-1 ("Glk1") polypeptide; a Glk1 polypeptide; a Hxk1 polypeptide and a Hxk2 polypeptide; a Glk1 polypeptide and a Hxk1 polypeptide; or a Hxk1 polypeptide, a Hxk2 polypeptide, and a Glk1 polypeptide.

2. The genetically engineered yeast of claim 1, wherein the Hxk1 polypeptide has at least 90% identity to SEQ ID NO:74, the Hxk2 polypeptide has at least 90% identity to SEQ ID NO:76, and the Glk1 polypeptide has at least 90% identity to SEQ ID NO:78.

3. A genetically engineered yeast having an ability to co-utilize sugars, wherein the biological activity of an endogenous protein having at least 90% sequence identity to an amino acid sequence set forth in: SEQ ID NO:74; SEQ ID NO:74 and 76; SEQ ID NO:74, 76, and 78; SEQ ID NO:78; SEQ ID NO:76 and 78; or SEQ ID NO:74 and 78 is reduced as compared to a control yeast.

4. The genetically engineered yeast of claim 1, wherein the attenuated expression is caused by at least one gene disruption of a Hxk1 gene, a Hxk2 gene, a Glk1 gene, or combinations thereof which results in attenuated expression of the Hxk1 gene, the Hxk2 gene, the Glk1 gene or combinations thereof.

5. The genetically engineered yeast of claim 1, wherein the microorganism expresses a Hxk1 polypeptide, a Hxk2 polypeptide, a Glk1 polypeptide or combinations thereof at a level of 10% or less than a control yeast.

6. The genetically engineered yeast of claim 1, wherein the yeast has improved sugar co-utilization of two or more sugars as compared to a control yeast.

7. The genetically engineered yeast of claim 1, wherein the yeast is selected from *Saccharomyces cerevisiae, Saccharomyces fermentati, Saccharomyces paradoxus, Saccharomyces uvarum, Saccharomyces bay anus, Schizosaccharomyces pombe, Schizosaccharomyces japonicus, Schizosaccharomyces octosporus, Schizosaccharomyces cryophilus, Torulaspora delbrueckii, Kluyveromyces marxianus, Pichia stipitis, Pichia pastoris, Pichia angusta, Zygosaccharomyces bailii, Brettanomyces inter medius, Brettanomyces bruxellensis, Brettanomyces anomalus, Brettanomyces custersianus, Brettanomyces naardenensis, Brettanomyces nanus, Dekkera bruxellensis, Dekkera anomala, Issatchenkia orientalis, Kloeckera apiculata*; and *Aureobasidium pullulans*.

8. The genetically engineered yeast of claim 1, wherein the yeast is *Saccharomyces cerevisiae*.

9. The genetically engineered yeast of claim 1, wherein the yeast additionally comprises a recombinant polynucleotide encoding a xylose reductase ("XYL1") polypeptide, a xylitol dehydrogenase ("XYL2") polypeptide, a xylulokinase ("XYL3") polypeptide, or a combination thereof.

10. The genetically engineered yeast of claim 1, wherein the yeast further has attenuated expression of a polynucleotide encoding a cytosolic aldehyde dehydrogenase ("Ald6") polypeptide, attenuated expression of a polynucleotide encoding a orotidine-5'-phosphate decarboxylase ("Ura3") polypeptide, or combinations thereof.

11. The genetically engineered yeast claim 1, wherein the polynucleotides encoding a Hxk1 polypeptide, a Hxk2 polypeptide, or a Glk1 polypeptide are mutated using a genetic manipulation technique selected from transcription activator-like effector nuclease ("TALEN") editing, Zinc Finger Nucleases, and clustered regularly interspaced short palindromic repeats editing ("CRISPR-Cas9").

12. The genetically engineered yeast of claim 1, wherein one or more regulatory elements controlling expression of the polynucleotides encoding a Hxk1 polypeptide, a Hxk2 polypeptide, a Glk1 polypeptide, or combinations thereof are mutated to attenuate expression of the Hxk1 polypeptide, the Hxk2 polypeptide, the Glk1 polypeptide, or combinations thereof as compared to a control yeast.

13. The genetically engineered yeast of claim 1, wherein the regulatory elements controlling expression of the polynucleotides encoding Hxk1, Hxk2, and Glk1 polypeptides are replaced with recombinant regulatory elements that attenuate the expression of the Hxk1 polypeptide, the Hxk2 polypeptide, the Glk1 polypeptide, or combinations thereof as compared to wild-type yeast or a control yeast.

14. The genetically engineered yeast of claim 1, wherein the Hxk1 polypeptide has a T89A mutation, the Hxk2 polypeptide has a P455F mutation, the Glk1 polypeptide has a S306P mutation, or combinations thereof.

15. A genetically engineered yeast comprising a polynucleotide encoding at least one mutant polypeptide selected from Hxk1 T89A, Hxk2 P455F, and Glk1 S306P.

16. The genetically engineered yeast of claim 1, wherein the yeast has a reduced glucose consumption rate as compared to a control yeast.

17. The genetically engineered yeast of claim 16, wherein the glucose consumption rate is about 25% or less of a control yeast.

18. The genetically engineered yeast of claim 6, wherein the two or more sugars are selected from glucose, galactose, lactose, arabinose, mannose, sucrose, fructose, xylobiose, cellobiose, xylose, rhamnose, 4-deoxy-L-erythro-5-hexoseulose urinate, maltose, and cellodextrins.

19. A method of making a genetically engineered yeast of claim 1, wherein the yeast has improved co-utilization of glucose and a second sugar, the method comprising mutating a polynucleotide encoding a Hxk1 polypeptide; a Hxk2 polypeptide and a Glk1 polypeptide; a Glk1 polypeptide; a Hxk1 polypeptide and a Hxk2 polypeptide; a Glk1 polypeptide and a Hxk1 polypeptide; or a Hxk1 polypeptide, a Hxk2 polypeptide, and a Glk1 polypeptide, such that the Hxk1 polypeptide, the Hxk2 polypeptide, the Glk1 polypeptide or combinations thereof are expressed at an attenuated rate as compared to a control yeast.

20. The method of claim 19, wherein the second sugar is galactose, xylose, sucrose, arabinose, maltose, or cellodextrins.

21. A method for co-utilization of two or more sugars in a fermentation reaction comprising contacting the yeast of claim 1 with the two or more sugars under fermentation conditions such that the two of more sugars are co-utilized at an improved rate as compared to a control yeast.

22. The method of claim 21, wherein the two or more sugars are selected from glucose, lactose, galactose, arabinose, mannose, sucrose, fructose, xylobiose, cellobiose, xylose, rhamnose, 4-deoxy-L-erythro-5-hexoseulose urinate, maltose, and cellodextrins.

23. The method of claim 21, wherein a first sugar is glucose and a second sugar is selected from galactose, lactose, arabinose, mannose, sucrose, fructose, xylobiose, cellobiose, xylose, rhamnose, 4-deoxy-L-erythro-5-hexoseulose urinate, maltose, and cellodextrins.

24. The method of claim 21, wherein the consumption of glucose is reduced as compared to a control yeast and the consumption of a second sugar is increased such that the two of more sugars are co-utilized at an improved rate as compared to a control yeast.

25. A method of fermenting mixtures of sugars comprising contacting the yeast of claim 1 with the mixture of sugars under fermentation conditions such that the mixture of sugars are co-fermented at an improved rate as compared to a control yeast.

26. A method of producing ethanol comprising contacting the yeast of claim 1 with two or more sugars under fermentation conditions such that the two of more sugars are co-utilized and ethanol is produced.

* * * * *